（12） United States Patent
Scheller et al.

(10) Patent No.: US 9,717,630 B1
(45) Date of Patent: *Aug. 1, 2017

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US); Craig Moore, O'Fallon, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/361,460

(22) Filed: Nov. 27, 2016

Related U.S. Application Data

(63) Continuation of application No. 15/187,165, filed on Jun. 20, 2016, now Pat. No. 9,554,942.

(51) Int. Cl.
*A61B 18/18* (2006.01)
*A61F 9/008* (2006.01)
*A61M 25/01* (2006.01)

(52) U.S. Cl.
CPC ..... *A61F 9/00823* (2013.01); *A61M 25/0147* (2013.01)

(58) Field of Classification Search
CPC .............. A61F 9/00823; A61M 25/0142
USPC ........................................... 606/4
See application file for complete search history.

(56) References Cited

U.S. PATENT DOCUMENTS

| 3,174,851 | A | 3/1965 | Buehler et al. |
| 4,122,853 | A | 10/1978 | Smith |
| 4,147,443 | A | 4/1979 | Skobel |
| 4,744,360 | A | 5/1988 | Bath |
| 5,190,050 | A | 3/1993 | Nitzsche |
| 5,228,852 | A | 7/1993 | Goldsmith et al. |
| 5,257,988 | A | 11/1993 | L'Esperance, Jr. |

(Continued)

FOREIGN PATENT DOCUMENTS

| EP | EP 0900547 B1 | 3/1999 |
| NL | WO 2013/133717 | 9/2013 |
| WO | WO 2006/091597 | 8/2006 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

(Continued)

*Primary Examiner* — Lynsey Crandall
*Assistant Examiner* — Sebastian X Lukjan
(74) *Attorney, Agent, or Firm* — Kevin P. Rollins

(57) ABSTRACT

A steerable laser probe may include a handle, an actuation lever, an optic fiber, and a housing tube. The housing tube may have a first housing tube portion having a first stiffness and a second housing tube portion having a second stiffness. The second stiffness may be greater than the first stiffness. The optic fiber may be disposed within the housing tube and within an inner bore of the handle. An actuation of the actuation lever about a pivot pin of the handle may gradually curve the optic fiber. An actuation of the actuation lever about the pivot pin of the handle may gradually straighten the optic fiber.

20 Claims, 40 Drawing Sheets

(56) References Cited

U.S. PATENT DOCUMENTS

| | | |
|---|---|---|
| 5,322,064 A | 6/1994 | Lundquist |
| 5,355,871 A | 10/1994 | Hurley et al. |
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 5,735,842 A | 4/1998 | Kruege et al. |
| 5,855,577 A | 1/1999 | Murphy-Chutorian et al. |
| 5,873,865 A | 2/1999 | Horzewski et al. |
| 5,951,544 A | 9/1999 | Konwitz |
| 6,123,699 A | 9/2000 | Webster, Jr. |
| 6,126,654 A | 10/2000 | Giba et al. |
| 6,178,354 B1 | 1/2001 | Gibson |
| 6,198,974 B1 | 3/2001 | Webster, Jr. |
| 6,330,837 B1 | 12/2001 | Charles et al. |
| 6,352,531 B1* | 3/2002 | O'Connor .......... A61B 1/00071 385/43 |
| 6,488,695 B1 | 12/2002 | Hickingbotham |
| 6,505,530 B2 | 1/2003 | Adler et al. |
| 6,530,913 B1 | 3/2003 | Giba et al. |
| 6,533,772 B1 | 3/2003 | Sherts et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,872,214 B2 | 3/2005 | Sonnenschein et al. |
| 6,984,230 B2 | 1/2006 | Scheller et al. |
| 7,004,957 B1 | 2/2006 | Dampney et al. |
| 7,226,444 B1 | 6/2007 | Ellman et al. |
| 7,303,533 B2 | 12/2007 | Johansen et al. |
| 7,402,158 B2 | 7/2008 | Scheller et al. |
| 7,555,327 B2 | 6/2009 | Matlock |
| 7,632,242 B2 | 12/2009 | Griffin et al. |
| 7,766,904 B2 | 8/2010 | Mc Gowan, Sr. et al. |
| 7,935,108 B2 | 5/2011 | Baxter et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,951,245 B2 | 2/2015 | Scheller et al. |
| 8,968,277 B2 | 3/2015 | Scheller et al. |
| 9,023,019 B2 | 5/2015 | Scheller et al. |
| 9,023,020 B2 | 5/2015 | Scheller et al. |
| 9,039,686 B2 | 5/2015 | Scheller et al. |
| 9,089,399 B2 | 7/2015 | Scheller et al. |
| 9,107,682 B2 | 8/2015 | Scheller et al. |
| 9,113,995 B2 | 8/2015 | Scheller et al. |
| 9,119,702 B2 | 9/2015 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0154379 A1 | 7/2005 | McGowen, Sr. et al. |
| 2005/0157985 A1 | 7/2005 | McGowan, Sr. et al. |
| 2005/0234437 A1 | 10/2005 | Baxter et al. |
| 2005/0272975 A1 | 12/2005 | McWeeney et al. |
| 2005/0277874 A1 | 12/2005 | Selkee |
| 2006/0129175 A1 | 6/2006 | Griffin et al. |
| 2006/0178674 A1 | 8/2006 | McIntyre |
| 2006/0293270 A1 | 12/2006 | Adamis et al. |
| 2007/0185514 A1 | 8/2007 | Kirchhevel |
| 2007/0260231 A1 | 11/2007 | Rose et al. |
| 2008/0132761 A1* | 6/2008 | Sonnenschein ...... A61B 1/0055 600/142 |
| 2008/0287938 A1 | 11/2008 | Scheller et al. |
| 2009/0018993 A1 | 1/2009 | Dick et al. |
| 2009/0163943 A1 | 6/2009 | Cavanaugh et al. |
| 2009/0187170 A1 | 7/2009 | Auld et al. |
| 2009/0312750 A1 | 12/2009 | Spaide |
| 2010/0004642 A1* | 1/2010 | Lumpkin ............... A61B 18/22 606/4 |
| 2010/0191224 A1 | 7/2010 | Butcher |
| 2010/0268234 A1 | 10/2010 | Aho et al. |
| 2010/0331883 A1 | 12/2010 | Schmitz et al. |
| 2011/0028947 A1 | 2/2011 | Scheller et al. |
| 2011/0144627 A1* | 6/2011 | Smith .................... A61F 9/008 606/4 |
| 2011/0144630 A1 | 6/2011 | Loeb |
| 2012/0116361 A1 | 5/2012 | Hanlon et al. |
| 2012/0245569 A1 | 9/2012 | Papac et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0090635 A1 | 4/2013 | Mansour |
| 2013/0096541 A1 | 4/2013 | Scheller et al. |
| 2013/0116671 A1 | 5/2013 | Scheller et al. |
| 2013/0144278 A1 | 6/2013 | Papac et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |
| 2014/0107629 A1 | 4/2014 | Scheller et al. |
| 2015/0038950 A1 | 2/2015 | Scheller et al. |

OTHER PUBLICATIONS

Ferry P.W. Melchels, Jan Feijen, Dirk W. Grijpma, A review on stereolithography and its applications in biomedical engineering, Biomaterials 31 (2010) 6121-6130.

* cited by examiner

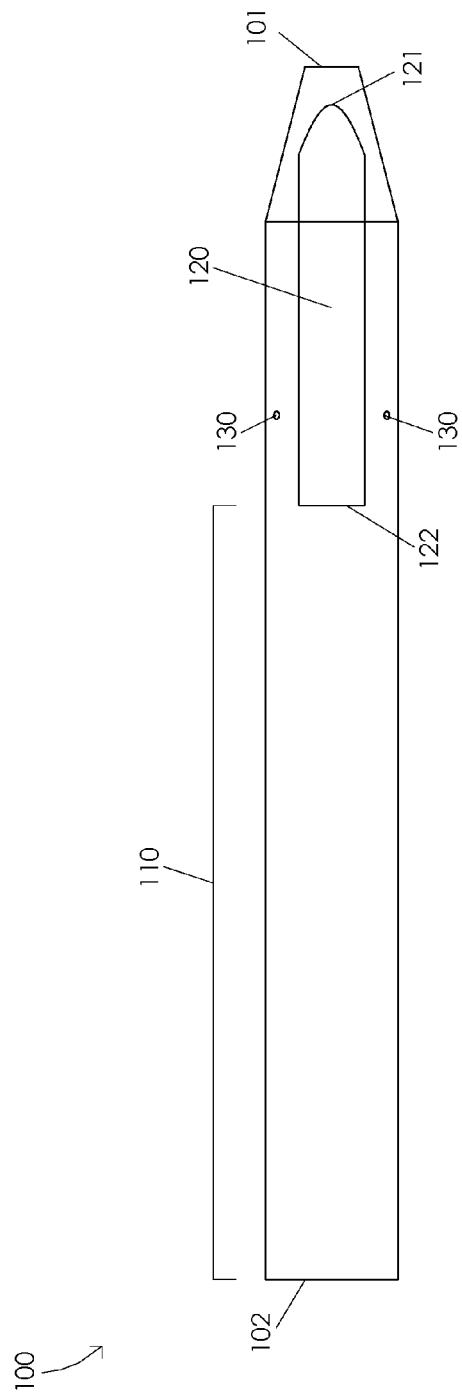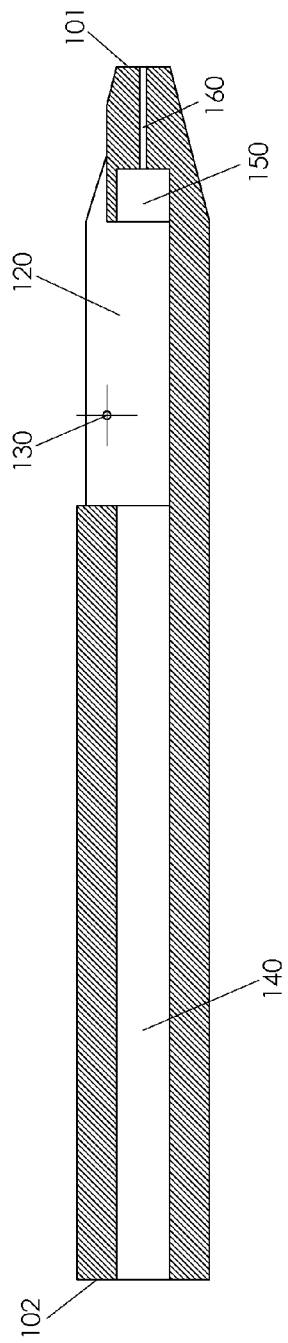
FIG. 1A
FIG. 1B

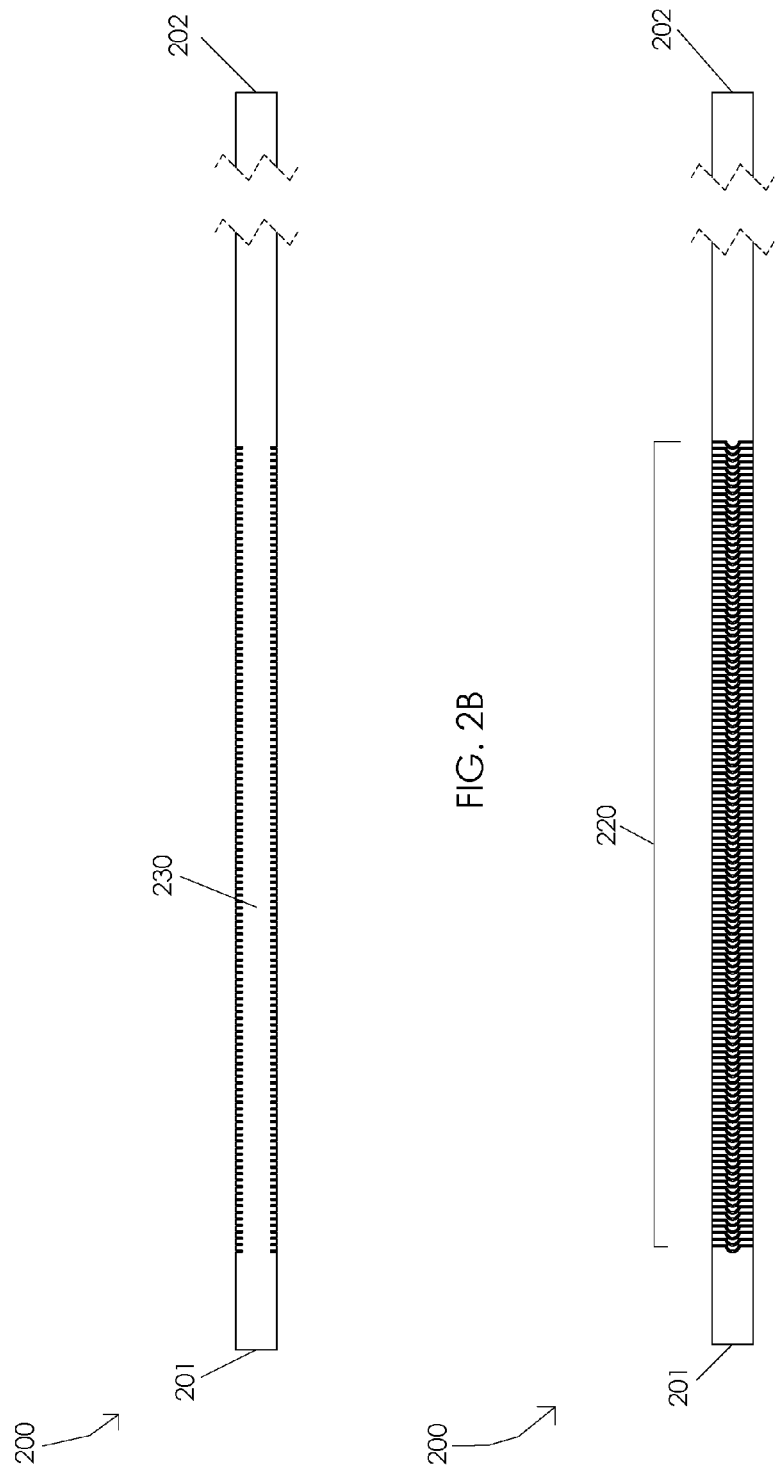

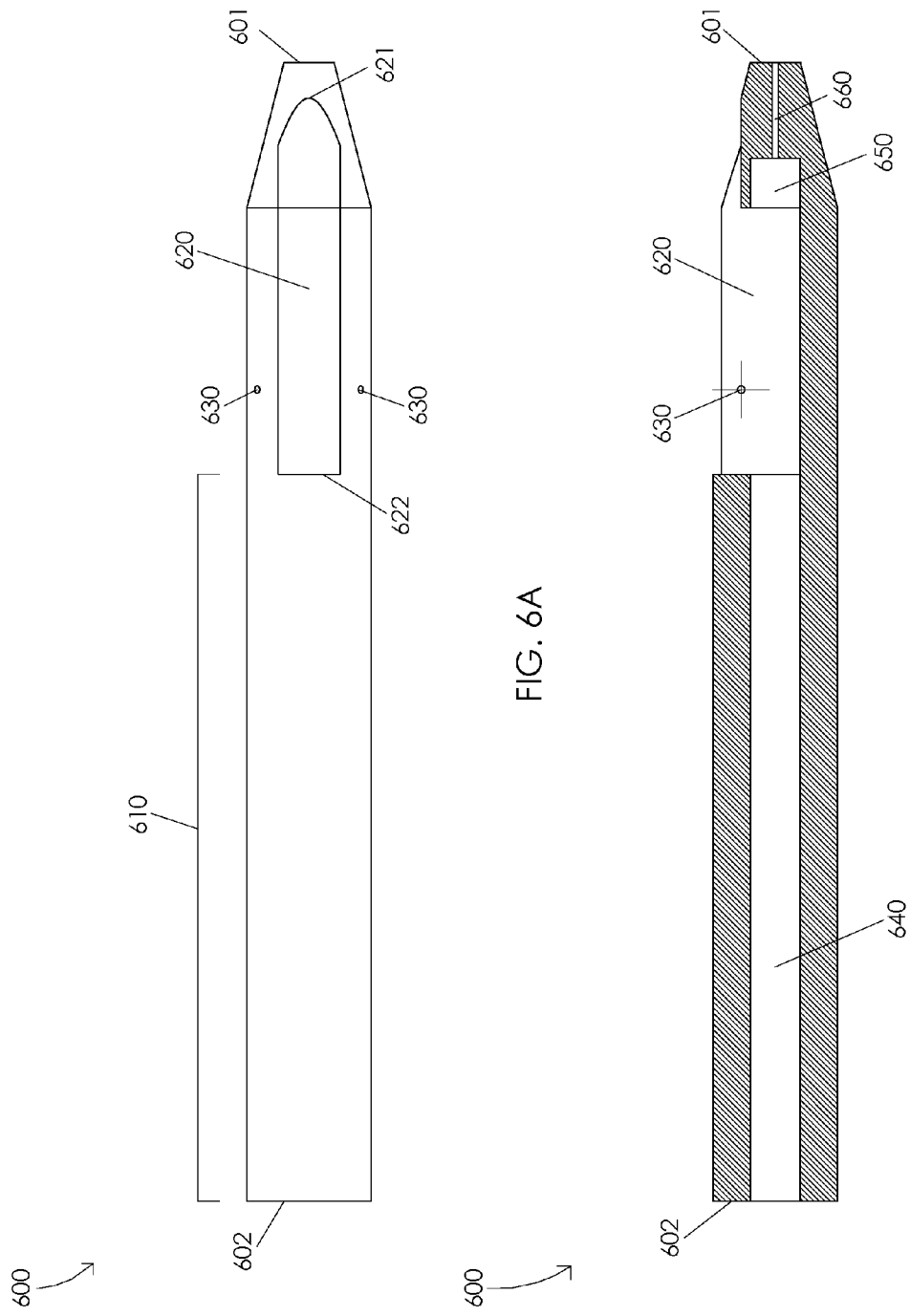

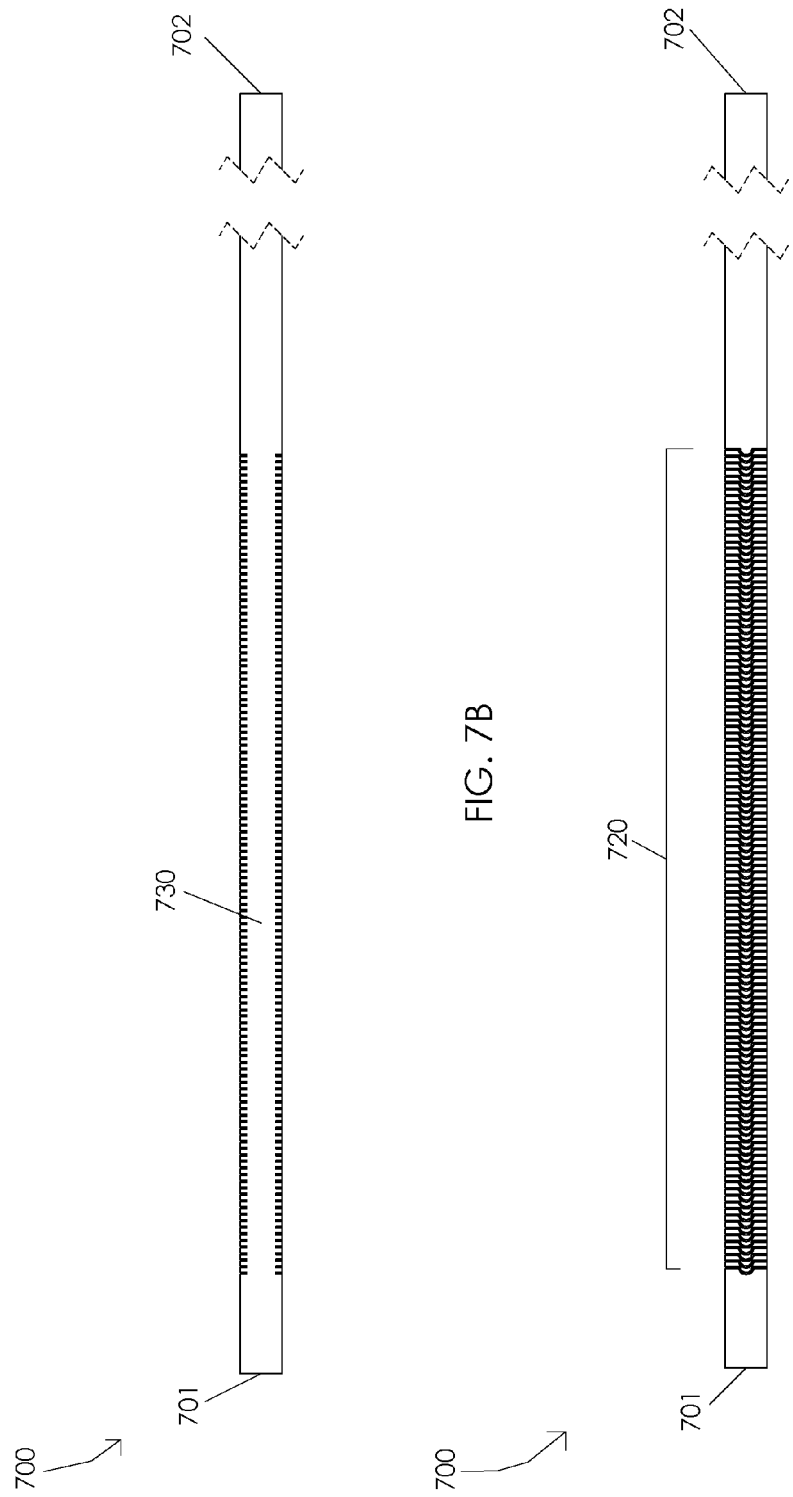

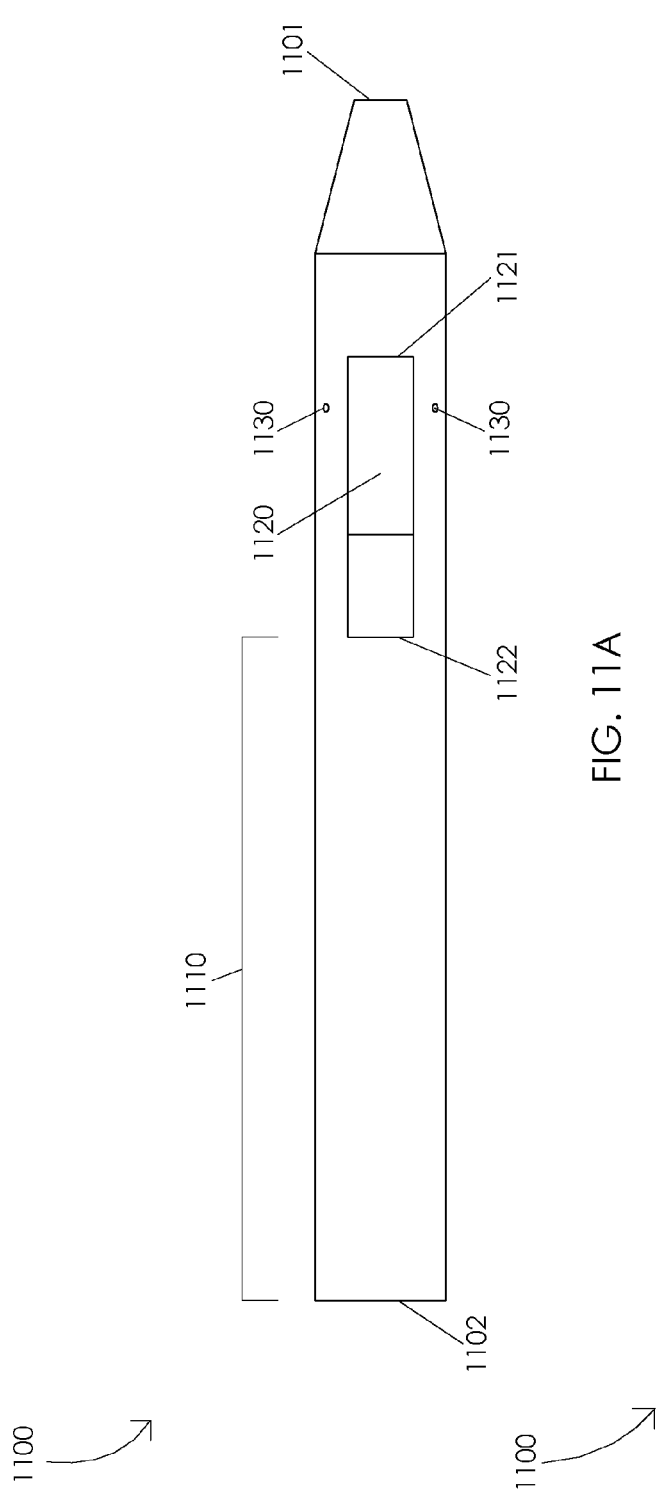
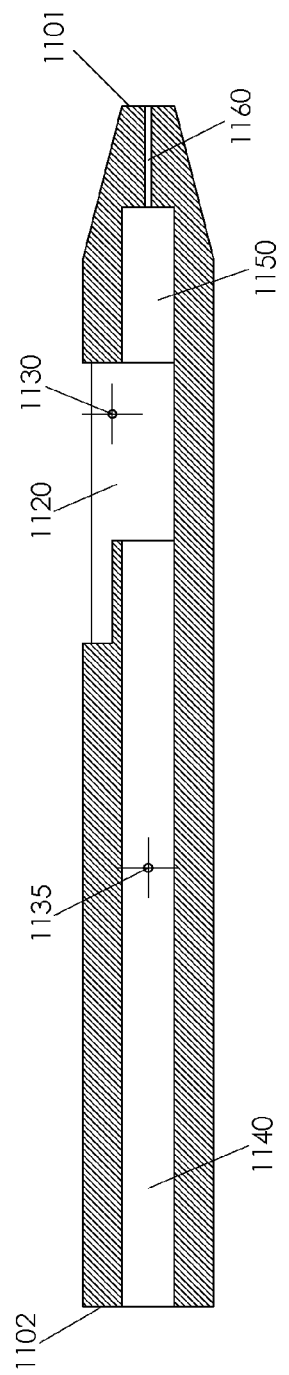
FIG. 11A
FIG. 11B

STEERABLE LASER PROBE

CROSS-REFERENCE TO RELATED APPLICATIONS

This Application is a continuation of prior application Ser. No. 15/187,165, filed Jun. 20, 2016.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle, an actuation lever, an optic fiber, and a housing tube. Illustratively, the housing tube may comprise a first housing tube portion having a first stiffness and a second housing tube portion having a second stiffness. In one or more embodiments, the second stiffness may be greater than the first stiffness. Illustratively, the optic fiber may be disposed within the housing tube and within an inner bore of the handle. In one or more embodiments, a portion of the optic fiber may be fixed to an inner portion of the housing tube, e.g., by a biocompatible adhesive or any other suitable means.

Illustratively, an actuation of the actuation lever, e.g., as a result of an application of a force to the actuation lever, may be configured to gradually compress a first housing tube portion of the housing tube. In one or more embodiments, a compression of the first housing tube portion may be configured to gradually curve the housing tube. Illustratively, a gradual curving of the housing tube may be configured to gradually curve the optic fiber.

In one or more embodiments, an actuation of the actuation lever, e.g., as a result of a reduction of a force applied to the actuation lever, may be configured to gradually decompress a first housing tube portion of the housing tube. Illustratively, a decompression of the first housing tube portion may be configured to gradually straighten the housing tube. In one or more embodiments, a gradual straightening of the housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

FIGS. 2A, 2B, and 2C are schematic diagrams illustrating a housing tube;

FIGS. 6A and 6B are schematic diagrams illustrating a handle;

FIGS. 7A, 7B, and 7C are schematic diagrams illustrating a housing tube;

FIGS. 11A and 11B are schematic diagrams illustrating a handle;

DETAILED DESCRIPTION OF AN ILLUSTRATIVE EMBODIMENT

Figure 2C:
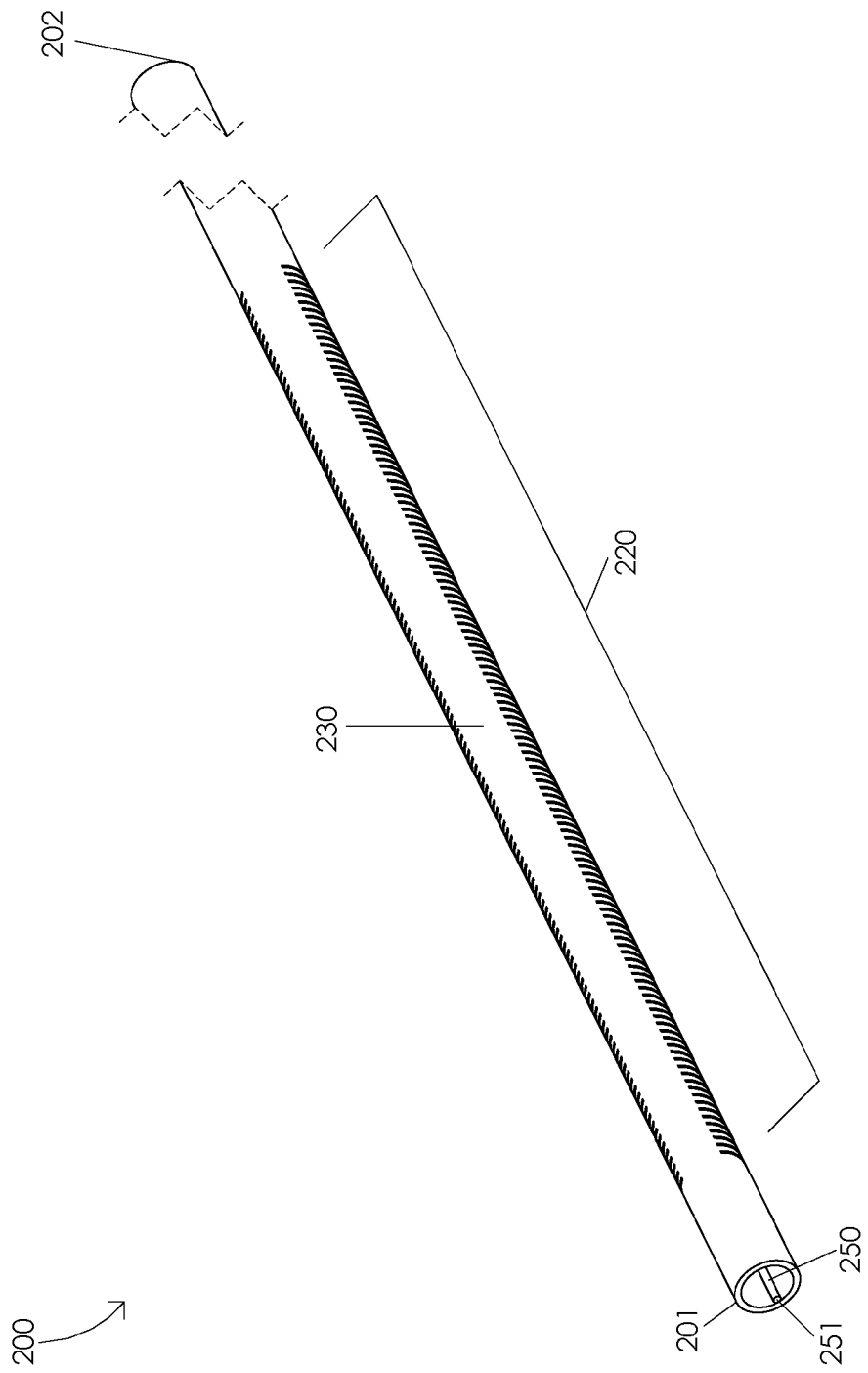

FIGS. 1A and 1B are schematic diagrams illustrating a handle 100. FIG. 1A illustrates a top view of handle 100. Illustratively, handle 100 may comprise a handle distal end 101 and a handle proximal end 102. In one or more embodiments, handle 100 may comprise a handle base 110, an actuation channel 120 having an actuation channel distal end 121 and an actuation channel proximal end 122, and a pivot pin housing 130. FIG. 1B illustrates a cross-sectional view of handle 100. Illustratively, handle 100 may comprise an inner bore 140, an inner bore distal chamber 150, and an optic fiber guide 160. Handle 100 may be manufactured from any suitable material, e.g., polymers, metals, metal alloys, etc., or from any combination of suitable materials.

FIGS. 2A, 2B, and 2C are schematic diagrams illustrating a housing tube 200. In one or more embodiments, housing tube 200 may comprise a housing tube distal end 201 and a housing tube proximal end 202. Housing tube 200 may be manufactured from any suitable material, e.g., polymers, metals, metal alloys, etc., or from any combination of suitable materials. FIG. 2A illustrates a housing tube 200 oriented to illustrate a first housing tube portion 220. Illustratively, first housing tube portion 220 may have a first stiffness. FIG. 2B illustrates a housing tube 200 oriented to illustrate a second housing tube portion 230. Illustratively, second housing tube portion 230 may have a second stiffness. In one or more embodiments, the second stiffness may be greater than the first stiffness. Illustratively, first housing tube portion 220 may comprise a first material having a first stiffness. In one or more embodiments, second housing tube portion 230 may comprise a second material having a second stiffness. Illustratively, the second stiffness may be greater than the first stiffness.

In one or more embodiments, first housing tube portion 220 may comprise one or more apertures configured to produce a first stiffness of first housing tube portion 220. Illustratively, second housing tube portion 230 may comprise a solid portion of housing tube 200 having a second stiffness. In one or more embodiments, the second stiffness may be greater than the first stiffness. Illustratively, first housing tube portion 220 may comprise one or more apertures configured to produce a first stiffness of first housing tube portion 220. In one or more embodiments, second housing tube portion 230 may comprise one or more apertures configured to produce a second stiffness of second housing tube portion 230. Illustratively, the second stiffness may be greater than the first stiffness.

In one or more embodiments, first housing tube portion 220 may comprise a plurality of slits configured to separate one or more solid portions of housing tube 200. Illustratively, a plurality of slits may be cut, e.g., laser cut, into first housing tube portion 220. In one or more embodiments, first housing tube portion 220 may comprise a plurality of slits configured to minimize a force of friction between housing tube 200 and a cannula, e.g., as housing tube 200 is inserted into the cannula or as housing tube 200 is extracted from the cannula. For example, each slit of the plurality of slits may comprise one or more arches configured to minimize a force of friction between housing tube 200 and a cannula.

FIG. 2C illustrates an angled view of housing tube 200. Illustratively, an optic fiber 250 may be disposed within housing tube 200. In one or more embodiments, optic fiber 250 may be disposed within housing tube 200 wherein an optic fiber distal end 251 may be adjacent to housing tube distal end 201. Illustratively, optic fiber 250 may be disposed within housing tube 200 wherein a portion of optic fiber 250 may be adjacent to a portion of first housing tube portion 220. In one or more embodiments, a portion of optic fiber 250 may be fixed to an inner portion of housing tube 200, e.g., by a biocompatible adhesive or any other suitable means.

Figure 3:
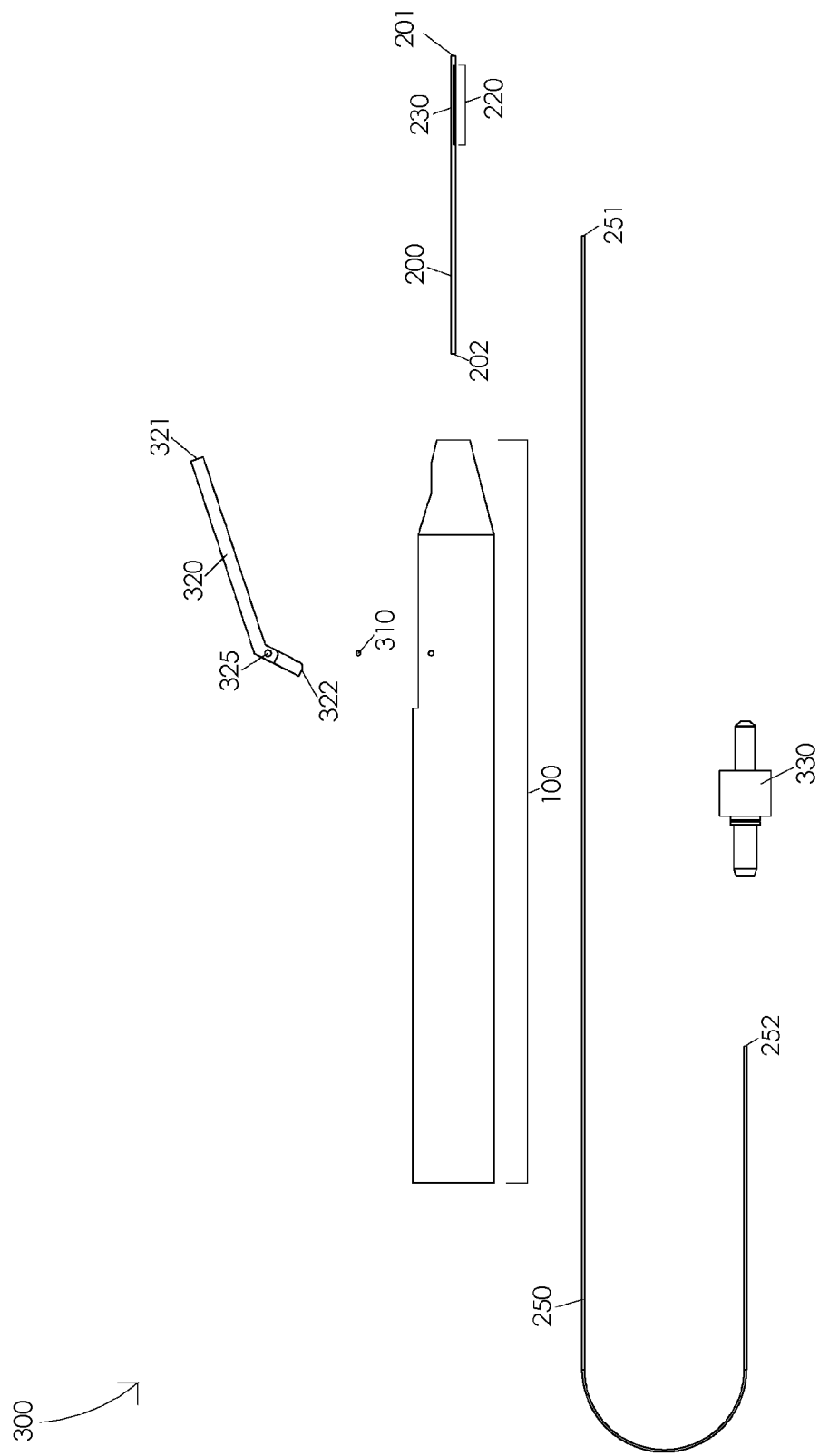
FIG. 3 is a schematic diagram illustrating an exploded view of a steerable laser probe assembly.

FIG. 3 is a schematic diagram illustrating an exploded view of a steerable laser probe assembly 300. In one or more embodiments, a steerable laser probe assembly 300 may comprise a handle 100, a housing tube 200 having a housing tube distal end 201 and a housing tube proximal end 202, an optic fiber 250 having an optic fiber distal end 251 and an optic fiber proximal end 252, a pivot pin 310, an actuation lever 320 having an actuation lever distal end 321 and an actuation lever proximal end 322, and a light source interface 330. Illustratively, light source interface 330 may be configured to interface with optic fiber proximal end 252. In one or more embodiments, light source interface 330 may comprise a standard light source connector, e.g., an SMA connector.

Illustratively, actuation lever 320 may comprise a pivot pin guide 325. In one or more embodiments, pivot pin 310 may be disposed within pivot pin housing 130 and pivot pin guide 325. Illustratively, pivot pin 310 may be configured to fix a portion of actuation lever 320 to a portion of handle 100. In one or more embodiments, pivot pin 310 may be fixed in a position within pivot pin housing 130. For example, pivot pin 310 may be fixed in a position within pivot pin housing 130, e.g., by an adhesive or any other suitable fixation means.

Illustratively, housing tube 200 may be fixed to handle 100, e.g., housing tube proximal end 202 may be fixed to handle distal end 101. In one or more embodiments, housing tube 200 may be fixed to handle 100, e.g., by an adhesive or any suitable fixation means. Illustratively, optic fiber 250 may be disposed within inner bore 140, actuation channel 120, inner bore distal chamber 150, optic fiber guide 160, and housing tube 200. In one or more embodiments, optic fiber 250 may be disposed within housing tube 200 wherein optic fiber distal end 251 may be adjacent to housing tube distal end 201. Illustratively, a portion of optic fiber 250 may be fixed to an inner portion of housing tube 200, e.g., by a biocompatible adhesive or by any other suitable fixation means.

In one or more embodiments, a portion of optic fiber 250 may be fixed to a portion of actuation lever 320, e.g., a portion of optic fiber 250 may be fixed to actuation lever proximal end 322. Illustratively, an application of a force to actuation lever 320 may be configured to actuate actuation lever 320, e.g., within actuation channel 120. In one or more embodiments, an application of a force to actuation lever 320 may be configured to rotate actuation lever 320 about pivot pin 310. Illustratively, an application of a force to actuation lever 320 may be configured to rotate actuation lever distal end 321 and actuation lever proximal end 322 about pivot pin 310, e.g., in a clockwise direction. In one or more embodiments, an application of a force to actuation lever 320 may be configured to actuate actuation lever distal end 321 away from handle proximal end 102 and configured to actuate actuation lever proximal end 322 towards handle proximal end 102. For example, an application of a force to actuation lever 320 may be configured to retract actuation lever proximal end 322 relative to handle base 110.

Illustratively, an actuation of actuation lever proximal end 322 towards handle proximal end 102, e.g., due to an application of a force to actuation lever 320, may be configured to retract optic fiber 250 relative to housing tube 200. In one or more embodiments, a retraction of optic fiber 250 relative to housing tube 200 may be configured to cause optic fiber 250 to apply a compressive force to an inner portion of housing tube 200. Illustratively, an application of a compressive force to an inner portion of housing tube 200 may be configured to gradually compress a portion of housing tube 200, e.g., a first housing tube portion 220 of housing tube 200. In one or more embodiments, a gradual compression of a portion of housing tube 200 may be configured to cause housing tube 200 to gradually curve. Illustratively, a gradual curving of housing tube 200 may be configured to gradually curve optic fiber 250.

In one or more embodiments, a reduction of a force applied to actuation lever 320 may be configured to actuate actuation lever 320, e.g., within actuation channel 120. Illustratively, a reduction of a force applied to actuation lever 320 may be configured to rotate actuation lever 320 about pivot pin 310. In one or more embodiments, a reduction of a force applied to actuation lever 320 may be configured to rotate actuation lever distal end 321 and actuation lever proximal end 322 about pivot pin 310, e.g., in a counters clockwise direction. Illustratively, a reduction of a force applied to actuation lever 320 may be configured to actuate actuation lever distal end 321 towards handle proximal end 102 and configured to actuate actuation lever proximal end 322 away from handle proximal end 102. For example, a reduction of a force applied to actuation lever 320 may be configured to extend actuation lever proximal end 322 relative to handle base 110.

In one or more embodiments, an actuation of actuation lever proximal end 322 away from handle proximal end 102, e.g., due to a reduction of a force applied to actuation lever 320, may be configured to extend optic fiber 250 relative to housing tube 200. Illustratively, an extension of optic fiber 250 relative to housing tube 200 may be configured to cause optic fiber 250 to reduce a compressive force applied to an inner portion of housing tube 200. In one or more embodiments, a reduction of a compressive force applied to an inner portion of housing tube 200 may be configured to gradually decompress a portion of housing tube 200, e.g., a first housing tube portion 220 of housing tube 200. Illustratively, a gradual decompression of a portion of housing tube 200 may be configured to cause housing tube 200 to gradually straighten. In one or more embodiments, a gradual straightening of housing tube 200 may be configured to gradually straighten optic fiber 250.

Figure 4A:
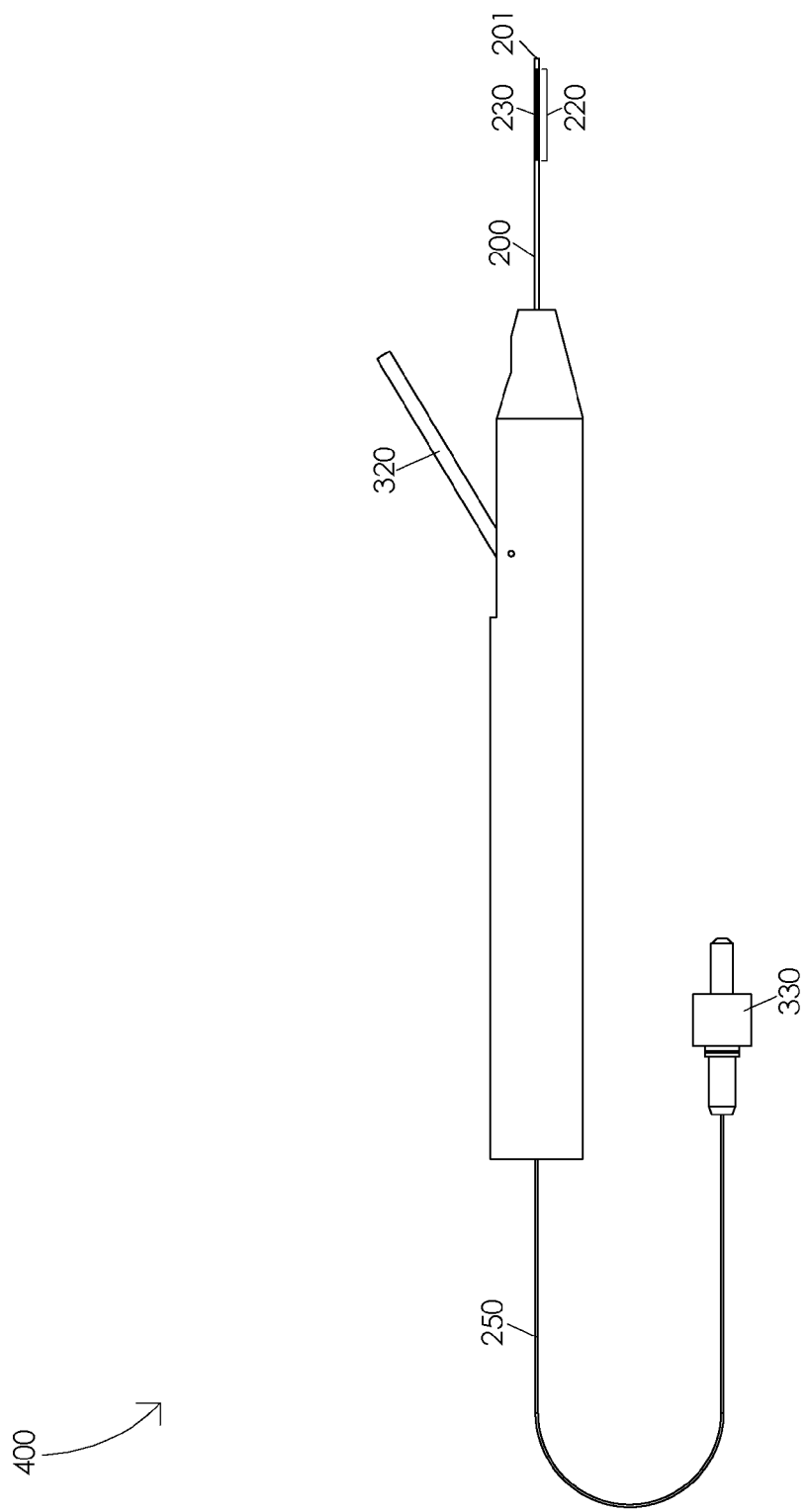
FIGS. 4A, 4B, 4C, 4D, and 4E illustrate a gradual curving of an optic fiber.

FIGS. 4A, 4B, 4C, 4D, and 4E illustrate a gradual curving of an optic fiber 250. FIG. 4A illustrates a straight optic fiber 400. In one or more embodiments, optic fiber 250 may comprise a straight optic fiber 400, e.g., when actuation lever proximal end 322 is fully extended relative to handle base 110. Illustratively, optic fiber 250 may comprise a straight optic fiber 400, e.g., when first housing tube portion 220 is fully decompressed. In one or more embodiments, a line tangent to optic fiber distal end 251 may be parallel to a line tangent to housing tube proximal end 202, e.g., when optic fiber 250 comprises a straight optic fiber 400.

Figure 4B:
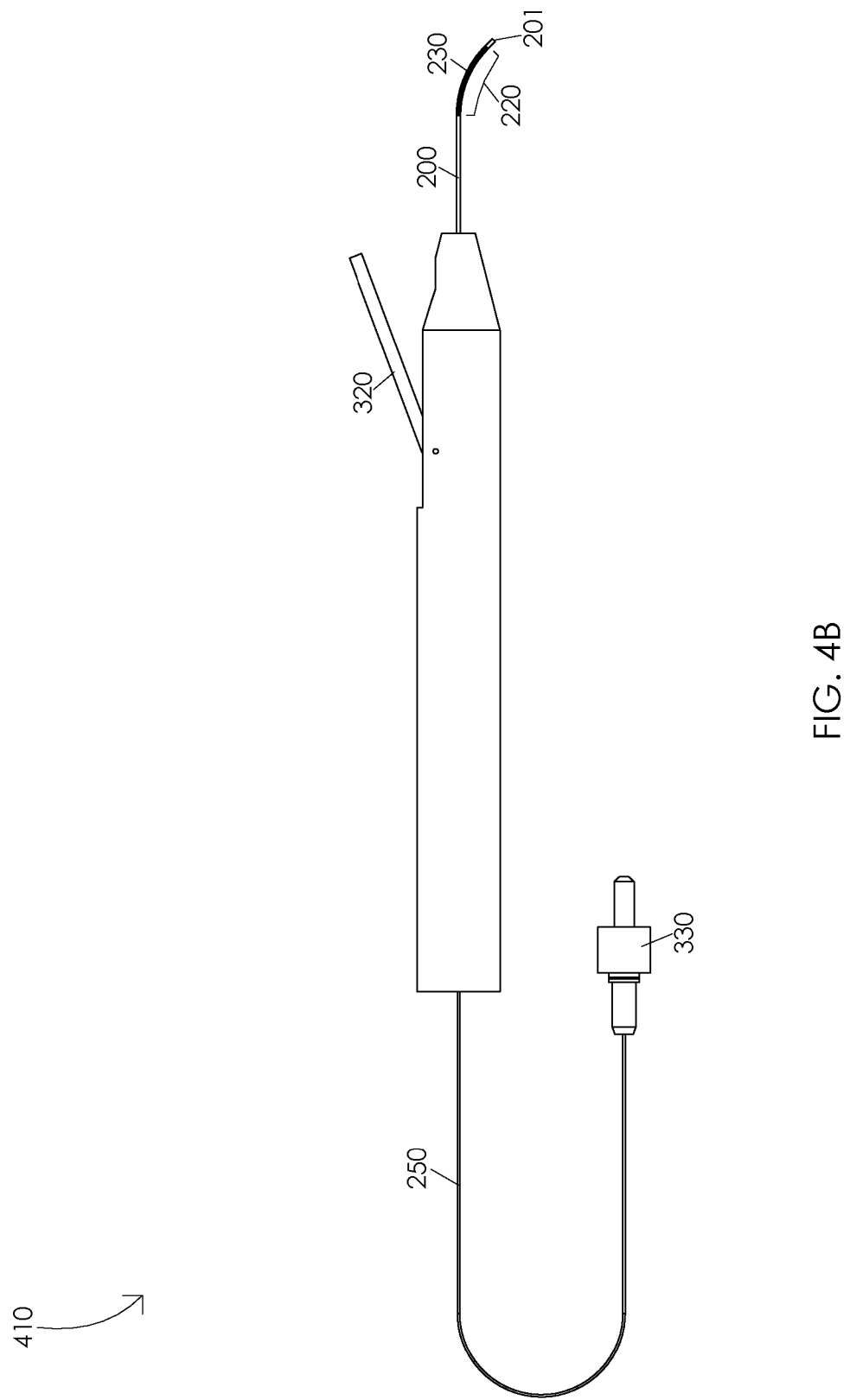

FIG. 4B illustrates an optic fiber in a first curved position 410. Illustratively, an actuation of actuation lever 320, e.g., in a clockwise direction about pivot pin 310, may be configured to gradually curve optic fiber 250. For example, an actuation of actuation lever 320, e.g., due to an application of a force to actuation lever 320, may be configured to gradually curve optic fiber 250. In one or more embodiments, an application of a force to actuation lever 320 may be configured to gradually curve optic fiber 250 from a straight optic fiber 400 to an optic fiber in a first curved position 410. Illustratively, an application of a force to actuation lever 320 may be configured to gradually retract optic fiber 250 relative to housing tube 200. In one or more embodiments, a gradual retraction of optic fiber 250 relative to housing tube 200 may be configured to cause optic fiber 250 to apply a compressive force to an inner portion of housing tube 200. Illustratively, an application of a compressive force to an inner portion of housing tube 200 may be configured to compress a first housing tube portion 220 of housing tube 200. In one or more embodiments, an application of a compressive force to an inner portion of housing tube 200 may be configured to gradually curve housing tube 200. Illustratively, a gradual curving of housing tube 200 may be configured to gradually curve optic fiber 250, e.g., from a straight optic fiber 400 to an optic fiber in a first curved position 410. In one or more embodiments, a line tangent to optic fiber distal end 251 may intersect a line tangent to housing tube proximal end 202 at a first angle, e.g., when optic fiber 250 comprises an optic fiber in a first curved position 410. Illustratively, the first angle may comprise any angle greater than zero degrees. For example, the first angle may comprise a 45 degree angle.

Figure 4C:
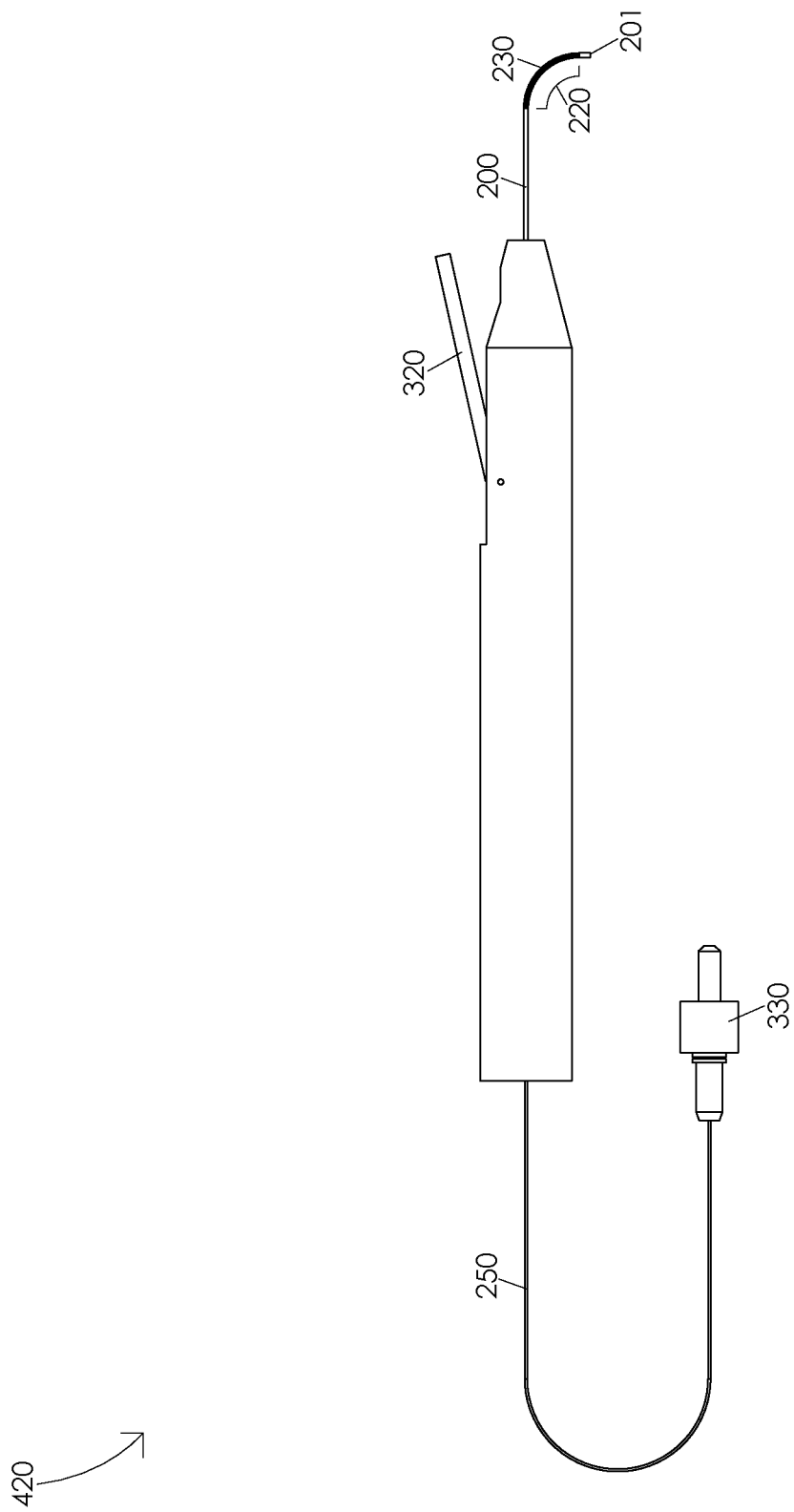

FIG. 4C illustrates an optic fiber in a second curved position 420. Illustratively, an actuation of actuation lever 320, e.g., in a clockwise direction about pivot pin 310, may be configured to gradually curve optic fiber 250. For example, an actuation of actuation lever 320, e.g., due to an application of a force to actuation lever 320, may be configured to gradually curve optic fiber 250. In one or more embodiments, an application of a force to actuation lever 320 may be configured to gradually curve optic fiber 250 from an optic fiber in a first curved position 410 to an optic fiber in a second curved position 420. Illustratively, an application of a force to actuation lever 320 may be configured to gradually retract optic fiber 250 relative to housing tube 200. In one or more embodiments, a gradual retraction of optic fiber 250 relative to housing tube 200 may be configured to cause optic fiber 250 to apply a compressive force to an inner portion of housing tube 200. Illustratively, an application of a compressive force to an inner portion of housing tube 200 may be configured to compress a first housing tube portion 220 of housing tube 200. In one or more embodiments, an application of a compressive force to an inner portion of housing tube 200 may be configured to gradually curve housing tube 200. Illustratively, a gradual curving of housing tube 200 may be configured to gradually curve optic fiber 250, e.g., from an optic fiber in a first curved position 410 to an optic fiber in a second curved position 420. In one or more embodiments, a line tangent to optic fiber distal end 251 may intersect a line tangent to housing tube proximal end 202 at a second angle, e.g., when optic fiber 250 comprises an optic fiber in a second curved position 420. Illustratively, the second angle may comprise any angle greater than the first angle. For example, the second angle may comprise a 90 degree angle.

Figure 4D:
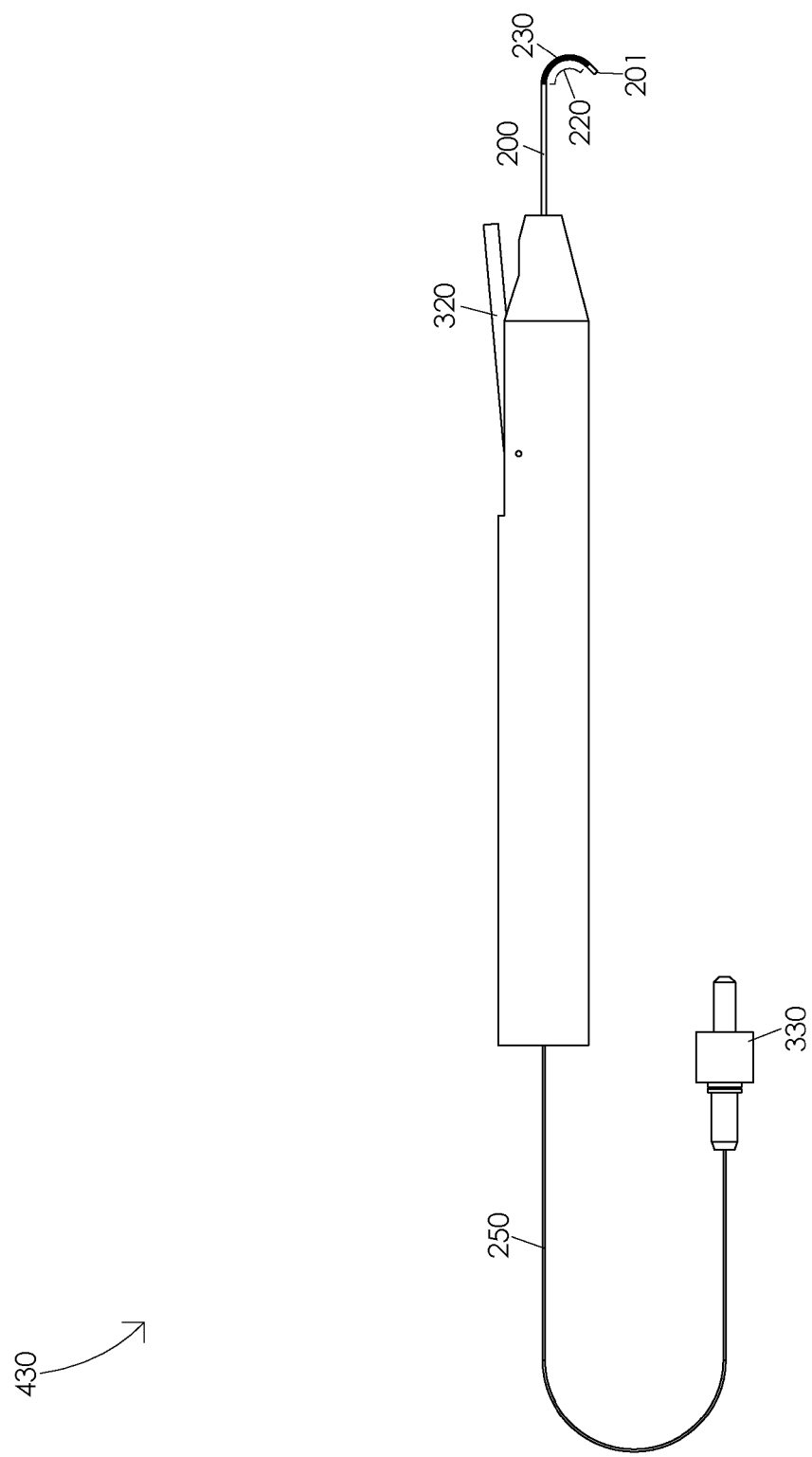

FIG. 4D illustrates an optic fiber in a third curved position 430. Illustratively, an actuation of actuation lever 320, e.g., in a clockwise direction about pivot pin 310, may be configured to gradually curve optic fiber 250. For example, an actuation of actuation lever 320, e.g., due to an application of a force to actuation lever 320, may be configured to gradually curve optic fiber 250. In one or more embodiments, an application of a force to actuation lever 320 may be configured to gradually curve optic fiber 250 from an optic fiber in a second curved position 420 to an optic fiber in a third curved position 430. Illustratively, an application of a force to actuation lever 320 may be configured to gradually retract optic fiber 250 relative to housing tube 200. In one or more embodiments, a gradual retraction of optic fiber 250 relative to housing tube 200 may be configured to cause optic fiber 250 to apply a compressive force to an inner portion of housing tube 200. Illustratively, an application of a compressive force to an inner portion of housing tube 200 may be configured to compress a first housing tube portion 220 of housing tube 200. In one or more embodiments, an application of a compressive force to an inner portion of housing tube 200 may be configured to gradually curve housing tube 200. Illustratively, a gradual curving of housing tube 200 may be configured to gradually curve optic fiber 250, e.g., from an optic fiber in a second curved position 420 to an optic fiber in a third curved position 430. In one or more embodiments, a line tangent to optic fiber distal end 251 may intersect a line tangent to housing tube proximal end 202 at a third angle, e.g., when optic fiber 250 comprises an optic fiber in a third curved position 430. Illustratively, the third angle may comprise any angle greater than the second angle. For example, the third angle may comprise a 135 degree angle.

Figure 4E:
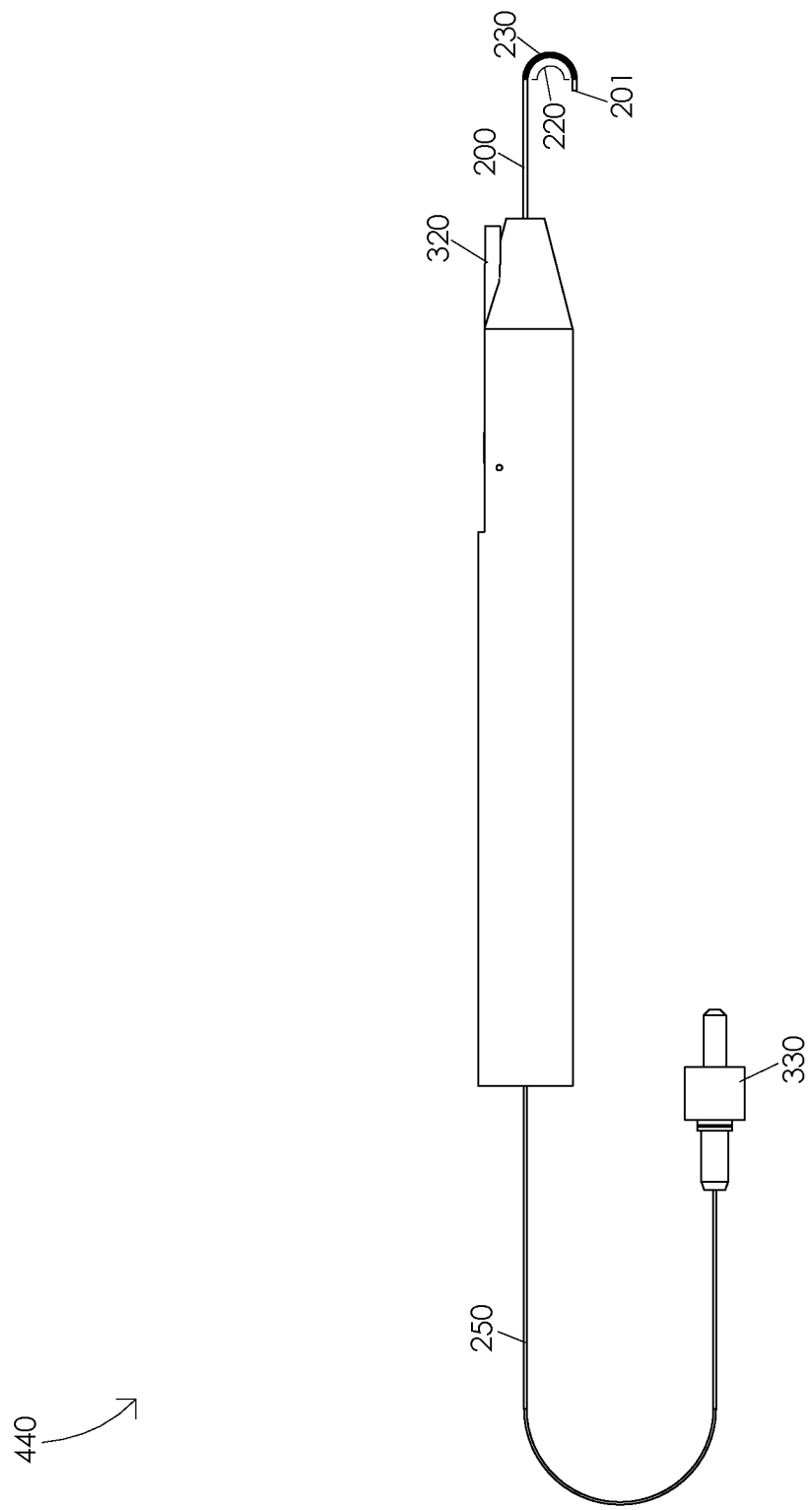

FIG. 4E illustrates an optic fiber in a fourth curved position 440. Illustratively, an actuation of actuation lever 320, e.g., in a clockwise direction about pivot pin 310, may be configured to gradually curve optic fiber 250. For example, an actuation of actuation lever 320, e.g., due to an application of a force to actuation lever 320, may be configured to gradually curve optic fiber 250. In one or more embodiments, an application of a force to actuation lever 320 may be configured to gradually curve optic fiber 250 from an optic fiber in a third curved position 430 to an optic fiber in a forth curved position 440. Illustratively, an application of a force to actuation lever 320 may be configured to gradually retract optic fiber 250 relative to housing tube 200. In one or more embodiments, a gradual retraction of optic fiber 250 relative to housing tube 200 may be configured to cause optic fiber 250 to apply a compressive force to an inner portion of housing tube 200. Illustratively, an application of a compressive force to an inner portion of housing tube 200 may be configured to compress a first housing tube portion 220 of housing tube 200. In one or more embodiments, an application of a compressive force to an inner portion of housing tube 200 may be configured to gradually curve housing tube 200. Illustratively, a gradual curving of housing tube 200 may be configured to gradually curve optic fiber 250, e.g., from an optic fiber in a third curved position 430 to an optic fiber in a fourth curved position 440. For example, a line tangent to optic fiber distal end 251 may be parallel to a line tangent to housing tube proximal end 202, e.g., when optic fiber 250 comprises an optic fiber in a fourth curved position 440.

In one or more embodiments, one or more properties of a steerable laser probe may be adjusted to attain one or more desired steerable laser probe features. For example, a stiffness of first housing tube portion 220 or a stiffness of second housing tube portion 230 may be adjusted to vary an amount of actuation of actuation lever 320 configured to curve housing tube 200 to a particular curved position. Illustratively, a material comprising first housing tube portion 220 or a material comprising second housing tube portion 230 may be adjusted to vary an amount of actuation of actuation lever 320 configured to curve housing tube 200 to a particular curved position.

In one or more embodiments, a number of apertures in housing tube 200 may be adjusted to vary an amount of actuation of actuation lever 320 configured to curve housing tube 200 to a particular curved position. Illustratively, a location of one or more apertures in housing tube 200 may be adjusted to vary an amount of actuation of actuation lever 320 configured to curve housing tube 200 to a particular curved position. In one or more embodiments, a geometry of one or more apertures in housing tube 200 may be adjusted to vary an amount of actuation of actuation lever 320 configured to curve housing tube 200 to a particular curved position. Illustratively, a geometry of one or more apertures in housing tube 200 may be uniform, e.g., each aperture of the one or more apertures may have a same geometry. In one or more embodiments, a geometry of one or more apertures in housing tube 200 may be non-uniform, e.g., a first aperture in housing tube 200 may have a first geometry and a second aperture in housing tube 200 may have a second geometry.

Illustratively, a geometry or shape of actuation lever 320 may be adjusted to vary an amount actuation of actuation lever 320 configured to curve housing tube 200 to a particular curved position. In one or more embodiments, one or more locations within housing tube 200 wherein optic fiber 250 may be fixed to an inner portion of housing tube 200 may be adjusted to vary an amount of actuation of actuation lever 320 configured to curve housing tube 200 to a particular curved position. Illustratively, at least a portion of optic fiber 250 may be enclosed in an optic fiber sleeve configured to, e.g., protect optic fiber 250, vary a stiffness of optic fiber 250, vary an optical property of optic fiber 250, etc. For example, a portion of optic fiber 250 that may be fixed to actuation lever 320, e.g., at actuation lever proximal end 322, may be enclosed in an optic fiber sleeve configured to, e.g., protect optic fiber 250, facilitate a fixation, etc. In one or more embodiments, a portion of optic fiber 250 that may be fixed to an inner portion of housing tube 200 may be enclosed in an optic fiber sleeve configured to, e.g., protect optic fiber 250, facilitate a fixation, etc. Illustratively, a portion of housing tube 200 may comprise an access window, e.g., configured to allow access to an inner portion of housing tube 200. In one or more embodiments, a portion of housing tube 200 may comprise an access window, e.g., configured to allow access to a portion of optic fiber 250.

Illustratively, a stiffness of first housing tube portion 220 or a stiffness of second housing tube portion 230 may be adjusted to vary a bend radius of housing tube 200. In one or more embodiments, a stiffness of first housing tube portion 220 or a stiffness of second housing tube portion 230 may be adjusted to vary a radius of curvature of housing tube 200, e.g., when housing tube 200 is in a particular curved position. Illustratively, a number of apertures in housing tube 200 may be adjusted to vary a bend radius of housing tube 200. In one or more embodiments, a number of apertures in housing tube 200 may be adjusted to vary a radius of curvature of housing tube 200, e.g., when housing tube 200 is in a particular curved position. Illustratively, a location or a geometry of one or more apertures in housing tube 200 may be adjusted to vary a bend radius of housing tube 200. In one or more embodiments, a location or a geometry of one or more apertures in housing tube 200 may be adjusted to vary a radius of curvature of housing tube 200, e.g., when housing tube 200 is in a particular curved position.

Figure 5A:
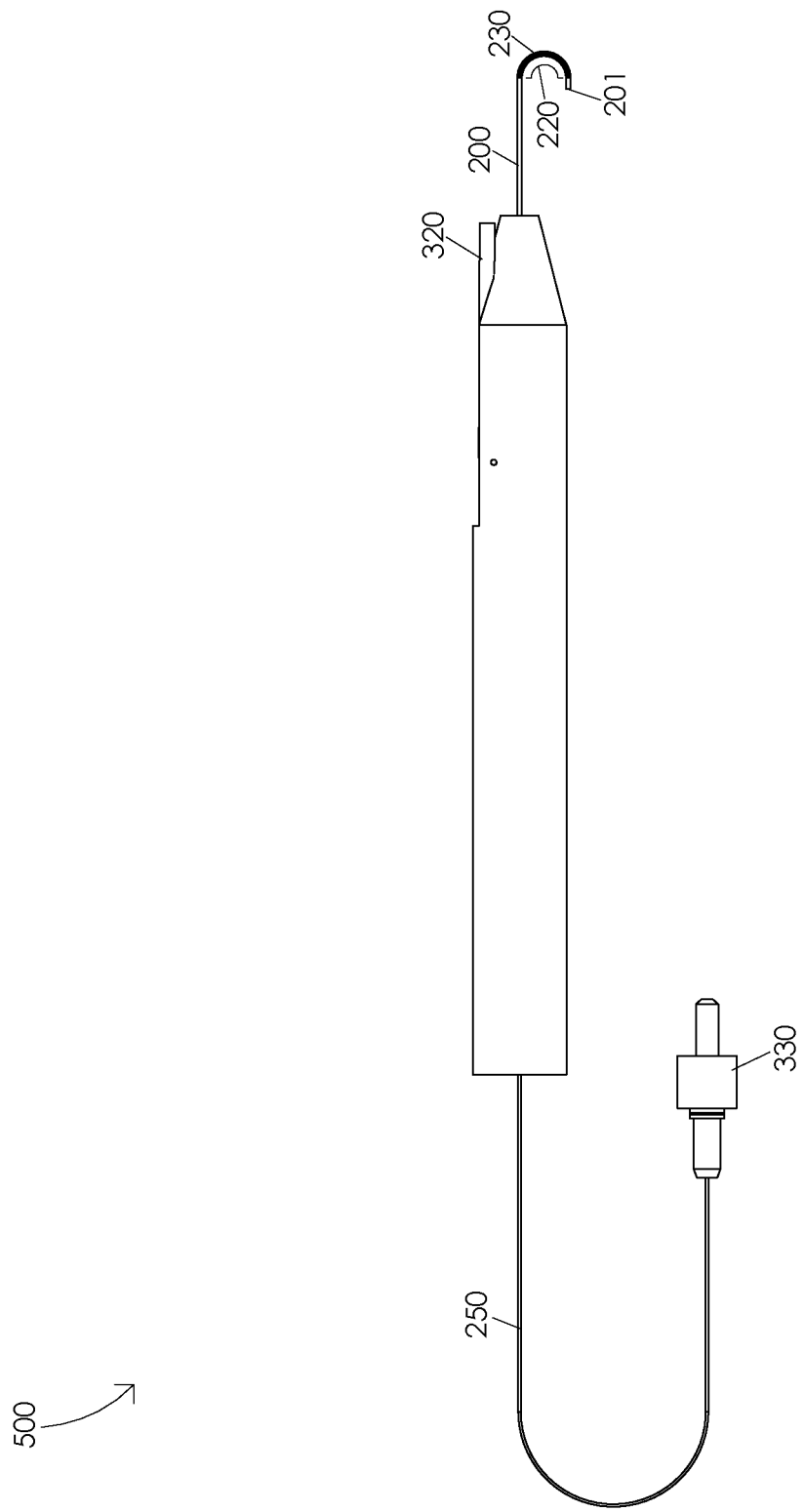
FIGS. 5A, 5B, 5C, 5D, and 5E illustrate a gradual straightening of an optic fiber.

FIGS. 5A, 5B, 5C, 5D, and 5E illustrate a gradual straightening of an optic fiber 250. FIG. 5A illustrates a fully curved optic fiber 500. In one or more embodiments, optic fiber 250 may comprise a fully curved optic fiber 500, e.g., when actuation lever proximal end 322 is fully retracted relative to handle base 110. Illustratively, optic fiber 250 may comprise a fully curved optic fiber 500, e.g., when first housing tube portion 220 is fully compressed. In one or more embodiments, a line tangent to optic fiber distal end 251 may be parallel to a line tangent to housing tube proximal end 202, e.g., when optic fiber 250 comprises a fully curved optic fiber 500.

Figure 5B:
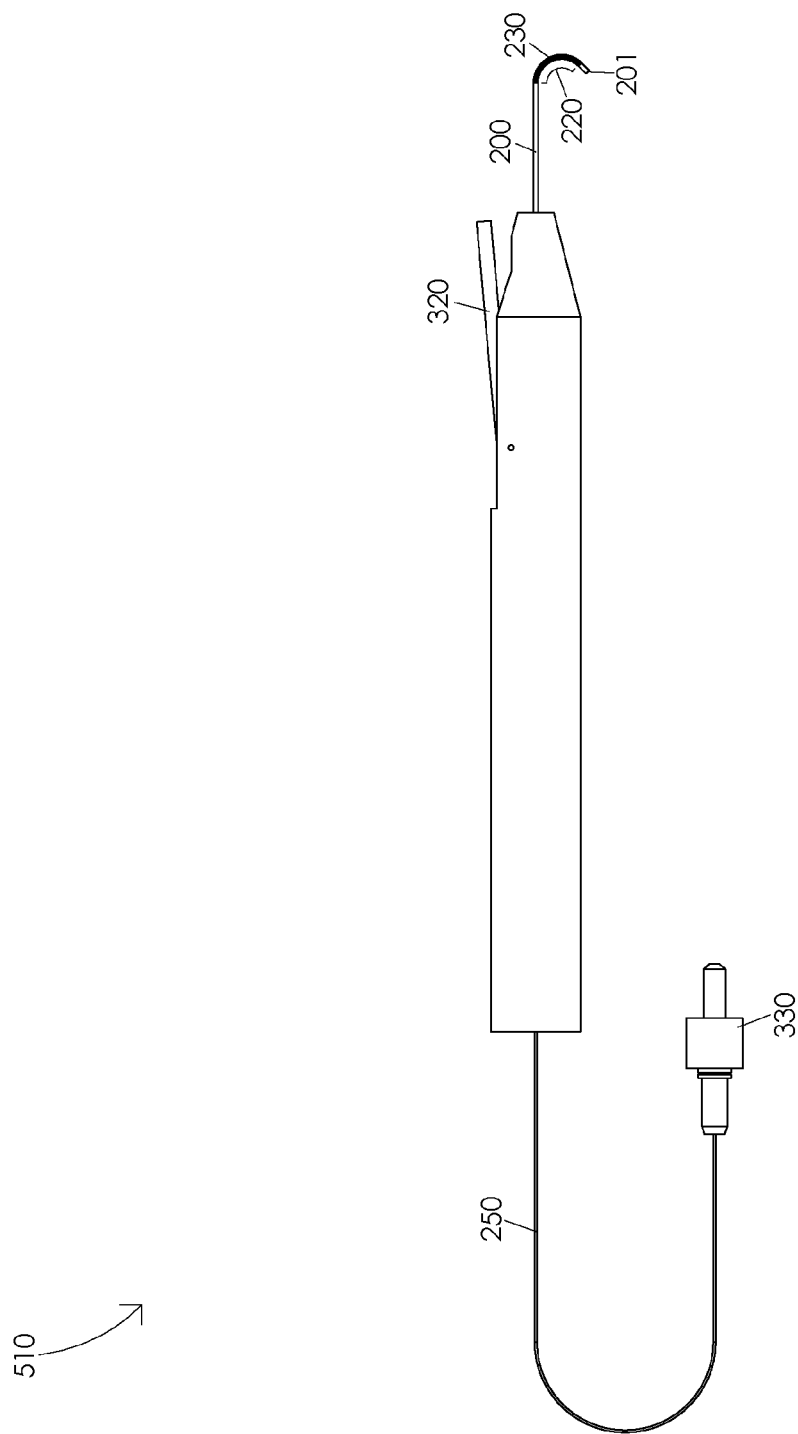

FIG. 5B illustrates an optic fiber in a first partially straightened position 510. Illustratively, an actuation of actuation lever 320, e.g., in a counter-clockwise direction about pivot pin 310, may be configured to gradually straighten optic fiber 250. For example, an actuation of actuation lever 320, e.g., due to a reduction of a force applied to actuation lever 320, may be configured to gradually straighten optic fiber 250. In one or more embodiments, a reduction of a force applied to actuation lever 320 may be configured to gradually straighten optic fiber 250 from a fully curved optic fiber 500 to an optic fiber in a first partially straightened position 510. Illustratively, a reduction of a force applied to actuation lever 320 may be configured to gradually extend optic fiber 250 relative to housing tube 200. In one or more embodiments, a gradual extension of optic fiber 250 relative to housing tube 200 may be configured to cause optic fiber 250 to reduce a compressive force applied to an inner portion of housing tube 200. Illustratively, a reduction of a compressive force applied to an inner portion of housing tube 200 may be configured to decompress a first housing tube portion 220 of housing tube 200. In one or more embodiments, a reduction of a compressive force applied to an inner portion of housing tube 200 may be configured to gradually straighten housing tube 200. Illustratively, a gradual straightening of housing tube 200 may be configured to gradually straighten optic fiber 250, e.g., from a fully curved optic fiber 500 to an optic fiber in a first partially straightened position 510. In one or more embodiments, a line tangent to optic fiber distal end 251 may intersect a line tangent to housing tube proximal end 202 at a first partially straightened angle, e.g., when optic fiber 250 comprises an optic fiber in a first partially straightened position 510. Illustratively, the first partially straightened angle may comprise any angle less than 180 degrees. For example, the first partially straightened angle may comprise a 135 degree angle.

Figure 5C:
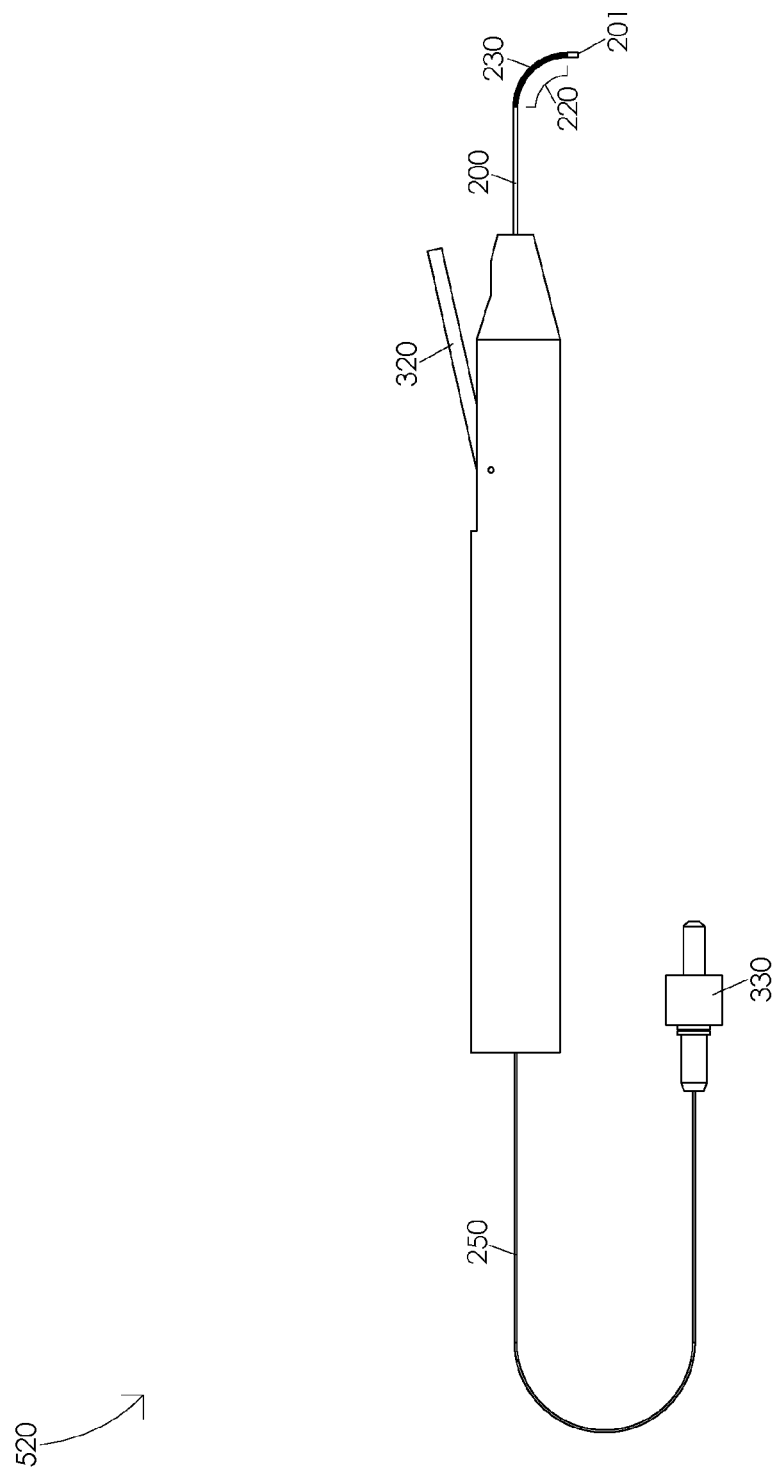

FIG. 5C illustrates an optic fiber in a second partially straightened position 520. Illustratively, an actuation of actuation lever 320, e.g., in a counter-clockwise direction about pivot pin 310, may be configured to gradually straighten optic fiber 250. For example, an actuation of actuation lever 320, e.g., due to a reduction of a force applied to actuation lever 320, may be configured to gradually straighten optic fiber 250. In one or more embodiments, a reduction of a force applied to actuation lever 320 may be configured to gradually straighten optic fiber 250 from an optic fiber in a first partially straightened position 510 to an optic fiber in a second partially straightened position 520. Illustratively, a reduction of a force applied to actuation lever 320 may be configured to gradually extend optic fiber 250 relative to housing tube 200. In one or more embodiments, a gradual extension of optic fiber 250 relative to housing tube 200 may be configured to cause optic fiber 250 to reduce a compressive force applied to an inner portion of housing tube 200. Illustratively, a reduction of a compressive force applied to an inner portion of housing tube 200 may be configured to decompress a first housing tube portion 220 of housing tube 200. In one or more embodiments, a reduction of a compressive force applied to an inner portion of housing tube 200 may be configured to gradually straighten housing tube 200. Illustratively, a gradual straightening of housing tube 200 may be configured to gradually straighten optic fiber 250, e.g., from an optic fiber in a first partially straightened position 510 to an optic fiber in a second partially straightened position 520. In one or more embodiments, a line tangent to optic fiber distal end 251 may intersect a line tangent to housing tube proximal end 202 at a second partially straightened angle, e.g., when optic fiber 250 comprises an optic fiber in a second partially straightened position 520. Illustratively, the second partially straightened angle may comprise any angle less than the first partially straightened angle. For example, the second partially straightened angle may comprise a 90 degree angle.

Figure 5D:
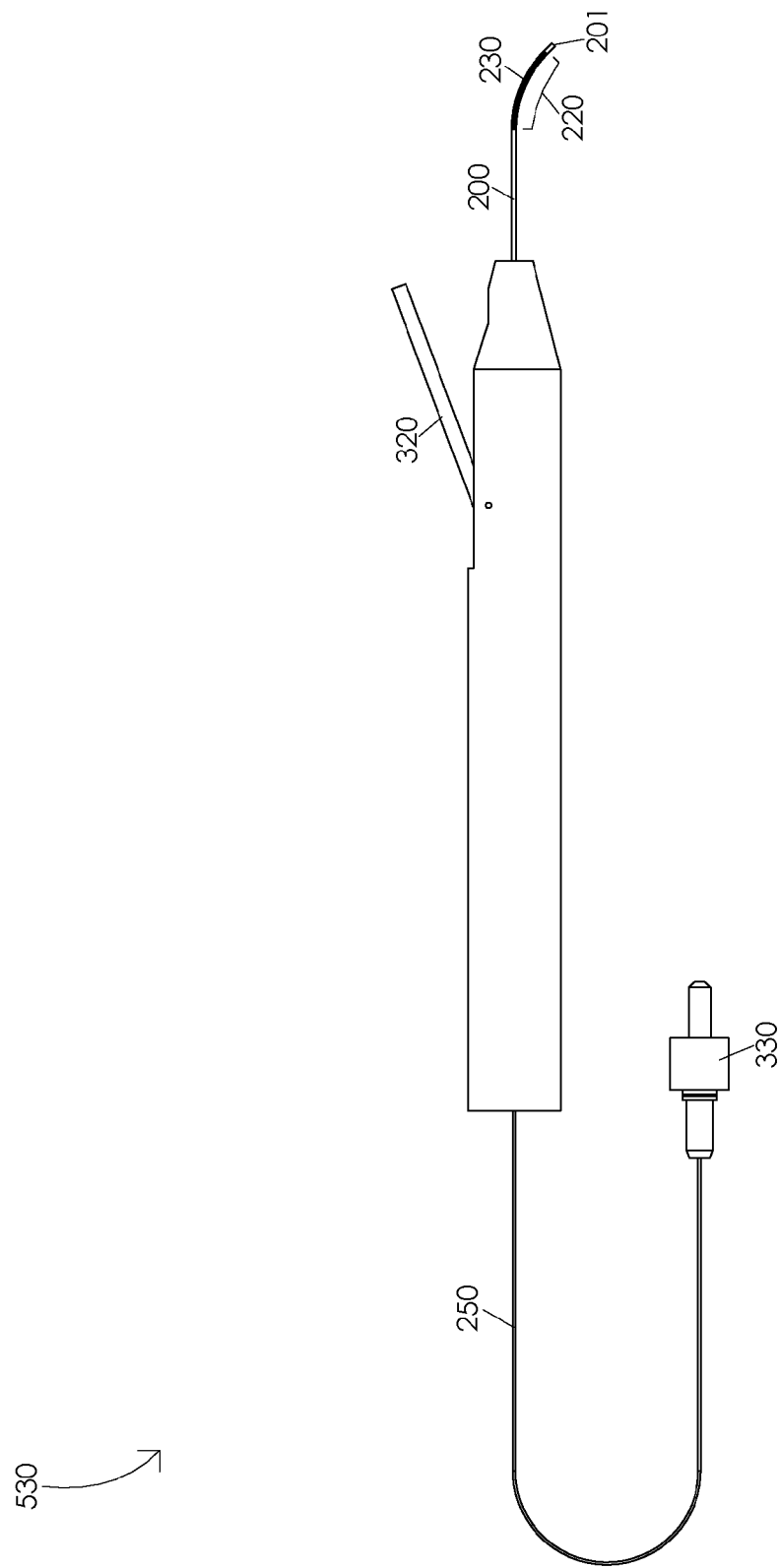

FIG. 5D illustrates an optic fiber in a third partially straightened position 530. Illustratively, an actuation of actuation lever 320, e.g., in a counter-clockwise direction about pivot pin 310, may be configured to gradually straighten optic fiber 250. For example, an actuation of actuation lever 320, e.g., due to a reduction of a force applied to actuation lever 320, may be configured to gradually straighten optic fiber 250. In one or more embodiments, a reduction of a force applied to actuation lever 320 may be configured to gradually straighten optic fiber 250 from an optic fiber in a second partially straightened position 520 to an optic fiber in a third partially straightened position 530. Illustratively, a reduction of a force applied to actuation lever 320 may be configured to gradually extend optic fiber 250 relative to housing tube 200. In one or more embodiments, a gradual extension of optic fiber 250 relative to housing tube 200 may be configured to cause optic fiber 250 to reduce a compressive force applied to an inner portion of housing tube 200. Illustratively, a reduction of a compressive force applied to an inner portion of housing tube 200 may be configured to decompress a first housing tube portion 220 of housing tube 200. In one or more embodiments, a reduction of a compressive force applied to an inner portion of housing tube 200 may be configured to gradually straighten housing tube 200. Illustratively, a gradual straightening of housing tube 200 may be configured to gradually straighten optic fiber 250, e.g., from an optic fiber in a second partially straightened position 520 to an optic fiber in a third partially straightened position 530. In one or more embodiments, a line tangent to optic fiber distal end 251 may intersect a line tangent to housing tube proximal end 202 at a third partially straightened angle, e.g., when optic fiber 250 comprises an optic fiber in a third partially straightened position 530. Illustratively, the third partially straightened angle may comprise any angle less than the second partially straightened angle. For example, the third partially straightened angle may comprise a 45 degree angle.

Figure 5E:
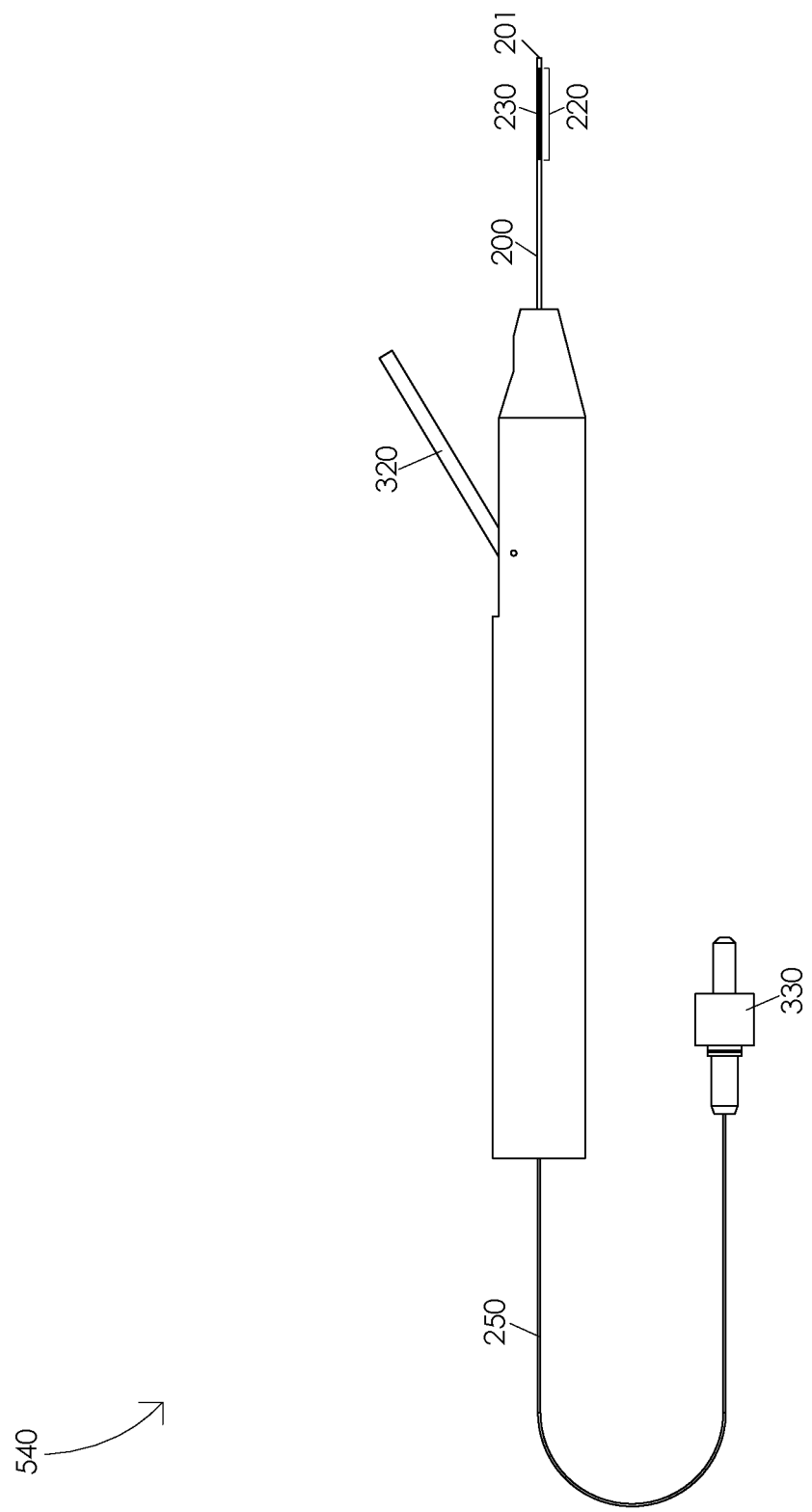

FIG. 5E illustrates an optic fiber in a fully straightened position 540. Illustratively, an actuation of actuation lever 320, e.g., in a counter-clockwise direction about pivot pin 310, may be configured to gradually straighten optic fiber 250. For example, an actuation of actuation lever 320, e.g., due to a reduction of a force applied to actuation lever 320, may be configured to gradually straighten optic fiber 250. In one or more embodiments, a reduction of a force applied to actuation lever 320 may be configured to gradually straighten optic fiber 250 from an optic fiber in a third partially straightened position 530 to an optic fiber in a fully straightened position 540. Illustratively, a reduction of a force applied to actuation lever 320 may be configured to gradually extend optic fiber 250 relative to housing tube 200. In one or more embodiments, a gradual extension of optic fiber 250 relative to housing tube 200 may be configured to cause optic fiber 250 to reduce a compressive force applied to an inner portion of housing tube 200. Illustratively, a reduction of a compressive force applied to an inner portion of housing tube 200 may be configured to decompress a first housing tube portion 220 of housing tube 200. In one or more embodiments, a reduction of a compressive force applied to an inner portion of housing tube 200 may be configured to gradually straighten housing tube 200. Illustratively, a gradual straightening of housing tube 200 may be configured to gradually straighten optic fiber 250, e.g., from an optic fiber in a third partially straightened position 530 to an optic fiber in a fully straightened position 540. In one or more embodiments, a line tangent to optic fiber distal end 251 may be parallel to a line tangent to housing tube proximal end 202, e.g., when optic fiber 250 comprises an optic fiber in a fully straightened position 540.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 100 to orient housing tube 200 in an orientation configured to cause a curvature of housing tube 200 within the particular transverse plane of the inner eye and varying an amount of actuation of actuation lever 320. Illustratively, a surgeon may aim optic fiber distal end 251 at any target within a particular sagittal plane of the inner eye by, e.g., rotating handle 100 to orient housing tube 200 in an orientation configured to cause a curvature of housing tube 200 within the particular sagittal plane of the inner eye and varying an amount of actuation of actuation lever 320. In one or more embodiments, a surgeon may aim optic fiber distal end 251 at any target within a particular frontal plane of the inner eye by, e.g., varying an amount of actuation of actuation lever 320 to orient a line tangent to optic fiber distal end 251 wherein the line tangent to optic fiber distal end 251 is within the particular frontal plane of the inner eye and rotating handle 100. Illustratively, a surgeon may aim optic fiber distal end 251 at any target located outside of the particular transverse plane, the particular sagittal plane, and the particular frontal plane of the inner eye, e.g., by varying a rotational orientation of handle 100 and varying an amount of actuation of actuation lever 320. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

FIGS. 6A and 6B are schematic diagrams illustrating a handle 600. FIG. 6A illustrates a top view of handle 600. Illustratively, handle 600 may comprise a handle distal end 601 and a handle proximal end 602. In one or more embodiments, handle 600 may comprise a handle base 610, an actuation channel 620 having an actuation channel distal end 621 and an actuation channel proximal end 622, and a pivot pin housing 630. FIG. 6B illustrates a cross-sectional view of handle 600. Illustratively, handle 600 may comprise an inner bore 640, an inner bore distal chamber 650, and an optic fiber guide 660. Handle 600 may be manufactured from any suitable material, e.g., polymers, metals, metal alloys, etc., or from any combination of suitable materials.

Figure 7C:
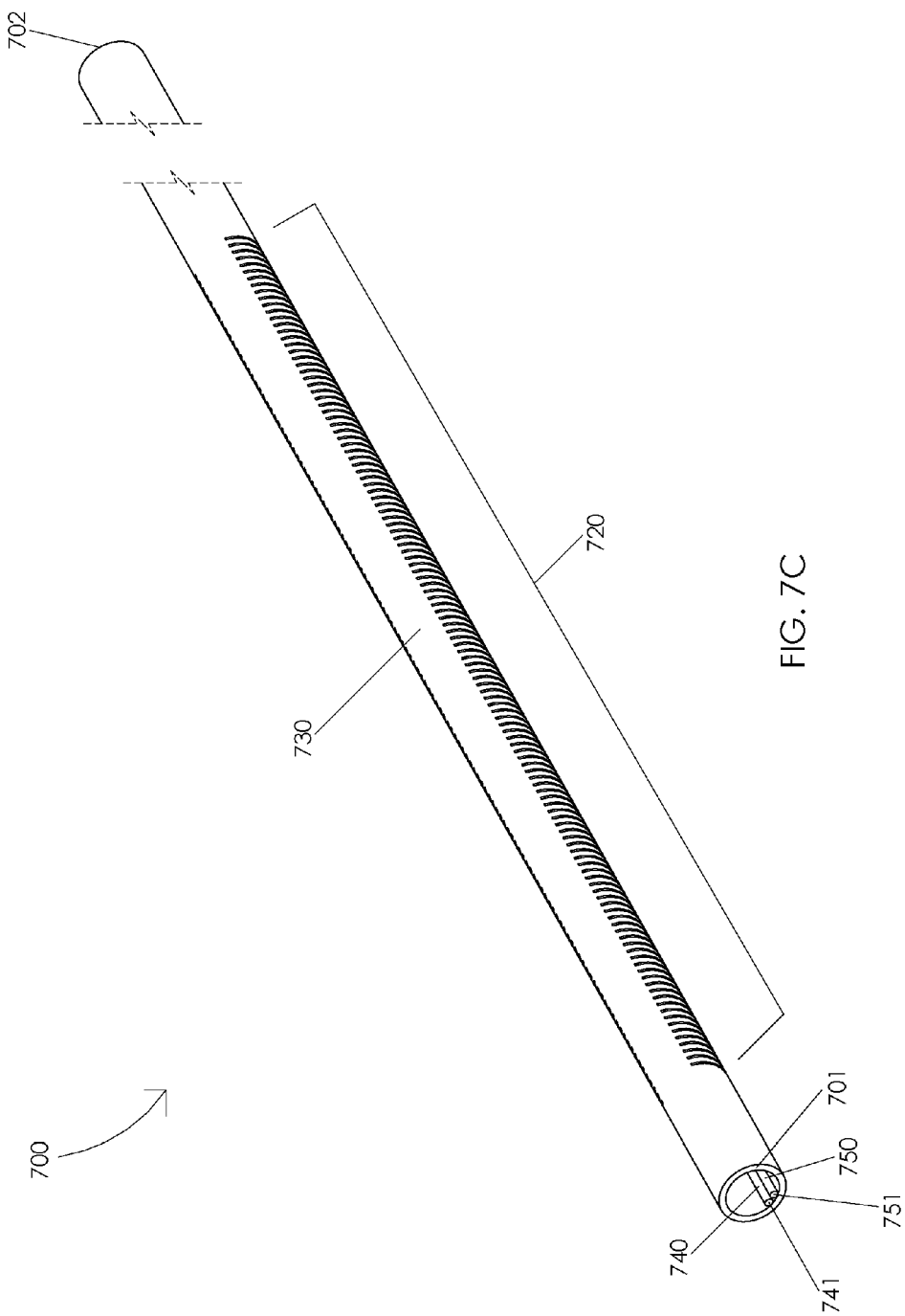

FIGS. 7A, 7B, and 7C are schematic diagrams illustrating a housing tube 700. In one or more embodiments, housing tube 700 may comprise a housing tube distal end 701 and a housing tube proximal end 702. Housing tube 700 may be manufactured from any suitable material, e.g., polymers, metals, metal alloys, etc., or from any combination of suitable materials. FIG. 7A illustrates a housing tube 700 oriented to illustrate a first housing tube portion 720. Illustratively, first housing tube portion 720 may have a first stiffness. FIG. 7B illustrates a housing tube 700 oriented to illustrate a second housing tube portion 730. Illustratively, second housing tube portion 730 may have a second stiffness. In one or more embodiments, the second stiffness may be greater than the first stiffness. Illustratively, first housing tube portion 720 may comprise a first material hays ing a first stiffness. In one or more embodiments, second housing tube portion 730 may comprise a second material having a second stiffness. Illustratively, the second stiffness may be greater than the first stiffness.

In one or more embodiments, first housing tube portion 720 may comprise one or more apertures configured to produce a first stiffness of first housing tube portion 720. Illustratively, second housing tube portion 730 may comprise a solid portion of housing tube 700 having a second stiffness. In one or more embodiments, the second stiffness may be greater than the first stiffness. Illustratively, first housing tube portion 720 may comprise one or more apertures configured to produce a first stiffness of first housing tube portion 720. In one or more embodiments, second housing tube portion 730 may comprise one or more apertures configured to produce a second stiffness of second housing tube portion 730. Illustratively, the second stiffness may be greater than the first stiffness.

In one or more embodiments, first housing tube portion 720 may comprise a plurality of slits configured to separate one or more solid portions of housing tube 700. Illustratively, a plurality of slits may be cut, e.g., laser cut, into first housing tube portion 720. In one or more embodiments, first housing tube portion 720 may comprise a plurality of slits configured to minimize a force of friction between housing tube 700 and a cannula, e.g., as housing tube 700 is inserted into the cannula or as housing tube 700 is extracted from the cannula. For example, each slit of the plurality of slits may comprise one or more arches configured to minimize a force of friction between housing tube 700 and a cannula.

FIG. 7C illustrates an angled view of housing tube 700. Illustratively, an optic fiber 750 may be disposed within housing tube 700. In one or more embodiments, optic fiber 750 may be disposed within housing tube 700 wherein an optic fiber distal end 751 is adjacent to housing tube distal end 701. Illustratively, optic fiber 750 may be disposed within housing tube 700 wherein a portion of optic fiber 750 may be adjacent to a portion of first housing tube portion 720. In one or more embodiments, a portion of optic fiber 750 may be fixed to an inner portion of housing tube 700, e.g., by a biocompatible adhesive or any other suitable means.

Illustratively, a wire 740 may be disposed within housing tube 700. In one or more embodiments, wire 740 may be disposed within housing tube 700 wherein a wire distal end 741 may be adjacent to housing tube distal end 701. Illustratively, wire 740 may be disposed within housing tube 700 wherein a portion of wire 740 may be adjacent to a portion of first housing tube portion 720. In one or more embodiments, a portion of wire 740 may be fixed to an inner portion of housing tube 700, e.g., by a biocompatible adhesive or any other suitable fixation means.

Figure 8:
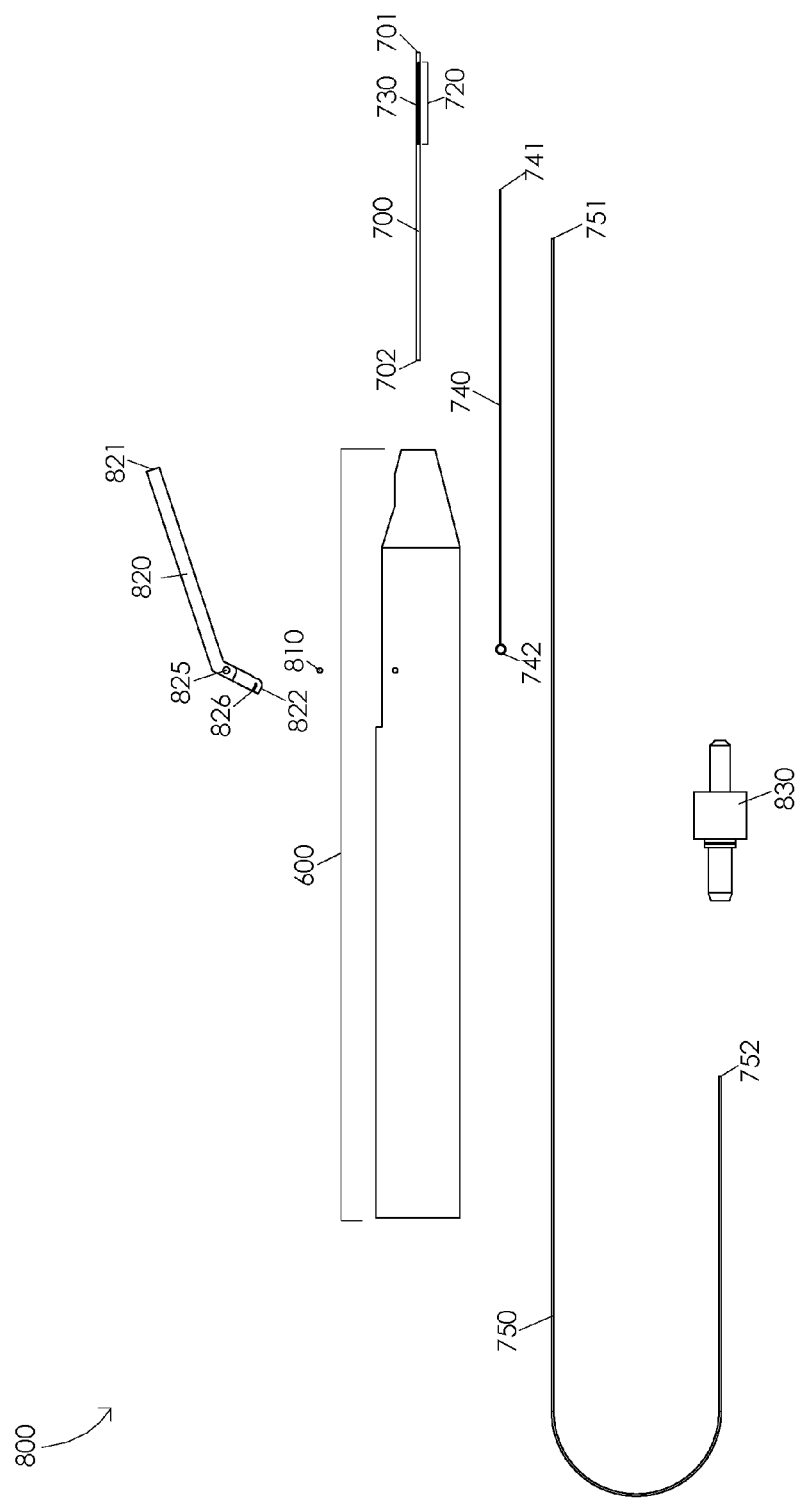
FIG. 8 is a schematic diagram illustrating an exploded view of a steerable laser probe assembly.

FIG. 8 is a schematic diagram illustrating an exploded view of a steerable laser probe assembly 800. In one or more embodiments, a steerable laser probe assembly 800 may comprise a handle 600, a housing tube 700 having a housing tube distal end 701 and a housing tube proximal end 702, a wire 740 having a wire distal end 741 and a wire proximal loop 742, an optic fiber 750 having an optic fiber distal end 751 and an optic fiber proximal end 752, a pivot pin 810, an actuation lever 820 having an actuation lever distal end 821 and an actuation lever proximal end 822, and a light source interface 830. Illustratively, light source interface 830 may be configured to interface with optic fiber proximal end 752. In one or more embodiments, light source interface 830 may comprise a standard light source connector, e.g., an SMA connector.

Illustratively, actuation lever 820 may comprise a pivot pin guide 825. In one or more embodiments, pivot pin 810 may be disposed within pivot pin housing 630 and pivot pin guide 825. Illustratively, pivot pin 810 may be configured to fix a portion of actuation lever 820 to a portion of handle 600. In one or more embodiments, pivot pin 810 may be fixed in a position within pivot pin housing 630. For example, pivot pin 810 may be fixed in a position within pivot pin housing 630, e.g., by an adhesive or any other suitable fixation means.

Illustratively, housing tube 700 may be fixed to handle 600, e.g., housing tube proximal end 702 may be fixed to handle distal end 601. In one or more embodiments, housing tube 700 may be fixed to handle 600, e.g., by an adhesive or any other suitable fixation means. Illustratively, actuation lever 820 may comprise a wire proximal loop housing 826. In one or more embodiments, wire proximal loop 742 may be disposed within wire proximal loop housing 826. Illustratively, wire proximal loop 742 may be fixed within wire proximal loop housing 826, e.g., by an adhesive or any suitable fixation means. In one or more embodiments, a portion of actuation lever 820 may be disposed within wire proximal loop 742, e.g., wire proximal loop 742 may be looped around a portion of actuation lever 820. Illustratively, wire 740 may be disposed within actuation channel 620, inner bore distal chamber 650, optic fiber guide 660, and housing tube 700. In one or more embodiments, wire 740 may be disposed within housing tube 700 wherein wire distal end 741 may be adjacent to housing tube distal end 701. Illustratively, wire 740 may be disposed within housing tube 700 wherein a portion of wire 740 may be adjacent to a portion of first housing tube portion 720. In one or more embodiments, a portion of wire 740 may be fixed to an inner portion of housing tube 700, e.g., by a biocompatible adhesive or by any other suitable fixation means.

Illustratively, optic fiber 750 may be disposed within inner bore 640, actuation channel 620, inner bore distal chamber 650, optic fiber guide 660, and housing tube 700. In one or more embodiments, optic fiber 750 may be disposed within housing tube 700 wherein optic fiber distal end 751 may be adjacent to housing tube distal end 701. Illustratively, a portion of optic fiber 750 may be fixed to an inner portion of housing tube 700, e.g., by a biocompatible adhesive or by any other suitable fixation means.

In one or more embodiments, an application of a force to actuation lever 820 may be configured to actuate actuation lever 820, e.g., within actuation channel 620. Illustratively, an application of a force to actuation lever 820 may be configured to rotate actuation lever 820 about pivot pin 810. In one or more embodiments, an application of a force to actuation lever 820 may be configured to rotate actuation lever distal end 821 and actuation lever proximal end 822 about pivot pin 810, e.g., in a clockwise direction. Illustratively, an application of a force to actuation lever 820 may be configured to actuate actuation lever distal end 821 away from handle proximal end 602 and configured to actuate actuation lever proximal end 822 towards handle proximal end 602. For example, an application of a force to actuation lever 820 may be configured to retract actuation lever proximal end 822 relative to handle base 610.

Illustratively, an actuation of actuation lever proximal end 822 towards handle proximal end 602, e.g., due to an application of a force to actuation lever 820, may be configured to retract wire 740 relative to housing tube 700. In one or more embodiments, a retraction of wire 740 relative to housing tube 700 may be configured to cause wire 740 to apply a compressive force to an inner portion of housing tube 700. Illustratively, an application of a compressive force to an inner portion of housing tube 700 may be configured to gradually compress a portion of housing tube 700, e.g., a first housing tube portion 720 of housing tube 700. In one or more embodiments, a gradual compression of a portion of housing tube 700 may be configured to cause housing tube 700 to gradually curve. Illustratively, a gradual curving of housing tube 700 may be configured to gradually curve optic fiber 750.

In one or more embodiments, a reduction of a force applied to actuation lever 820 may be configured to actuate actuation lever 820, e.g., within actuation channel 620. Illustratively, a reduction of a force applied to actuation lever 820 may be configured to rotate actuation lever 820 about pivot pin 810. In one or more embodiments, a reduction of a force applied to actuation lever 820 may be configured to rotate actuation lever distal end 821 and actuation lever proximal end 822 about pivot pin 810, e.g., in a counter-clockwise direction. Illustratively, a reduction of a force applied to actuation lever 820 may be configured to actuate actuation lever distal end 821 towards handle proximal end 602 and configured to actuate actuation lever proximal end 822 away from handle proximal end 602. For example, a reduction of a force applied to actuation lever 820 may be configured to extend actuation lever proximal end 822 relative to handle base 610.

In one or more embodiments, an actuation of actuation lever proximal end 822 away from handle proximal end 602, e.g., due to a reduction of a force applied to actuation lever 820, may be configured to extend wire 740 relative to housing tube 700. Illustratively, an extension of wire 740 relative to housing tube 700 may be configured to cause wire 740 to reduce a compressive force applied to an inner portion of housing tube 700. In one or more embodiments, a reduction of a compressive force applied to an inner portion of housing tube 700 may be configured to gradually decompress a portion of housing tube 700, e.g., a first housing tube portion 720 of housing tube 700. Illustratively, a gradual decompression of a portion of housing tube 700 may be configured to cause housing tube 700 to gradually straighten. In one or more embodiments, a gradual straightening of housing tube 700 may be configured to gradually straighten optic fiber 750.

Figure 9A:
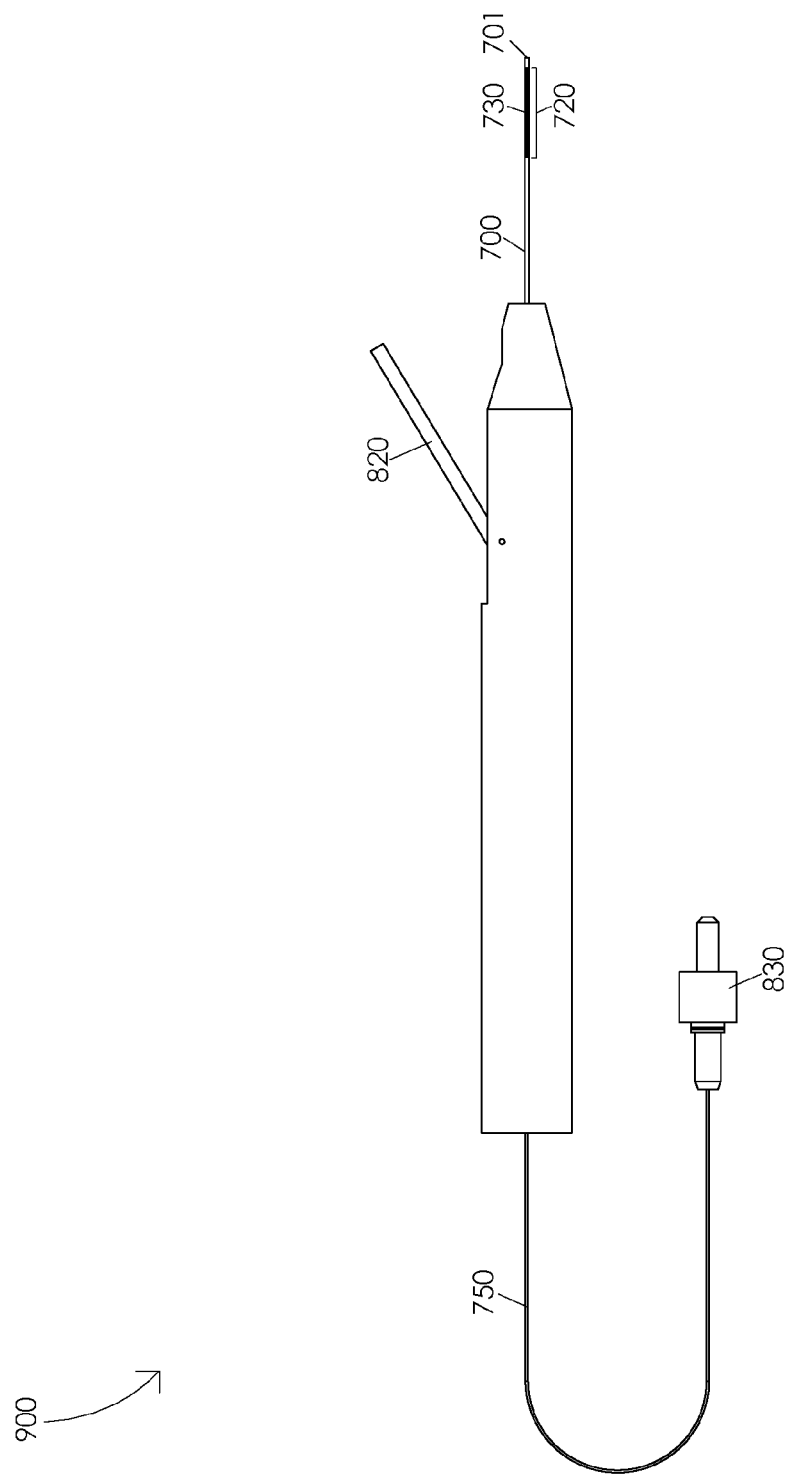
FIGS. 9A, 9B, 9C, 9D, and 9E illustrate a gradual curving of an optic fiber.

FIGS. 9A, 9B, 9C, 9D, and 9E illustrate a gradual curving of an optic fiber 750. FIG. 9A illustrates a straight optic fiber 900. In one or more embodiments, optic fiber 750 may comprise a straight optic fiber 900, e.g., when actuation lever proximal end 822 is fully extended relative to handle base 610. Illustratively, optic fiber 750 may comprise a straight optic fiber 900, e.g., when first housing tube portion 720 is fully decompressed. In one or more embodiments, a line tangent to optic fiber distal end 751 may be parallel to a line tangent to housing tube proximal end 702, e.g., when optic fiber 750 comprises a straight optic fiber 900.

Figure 9B:
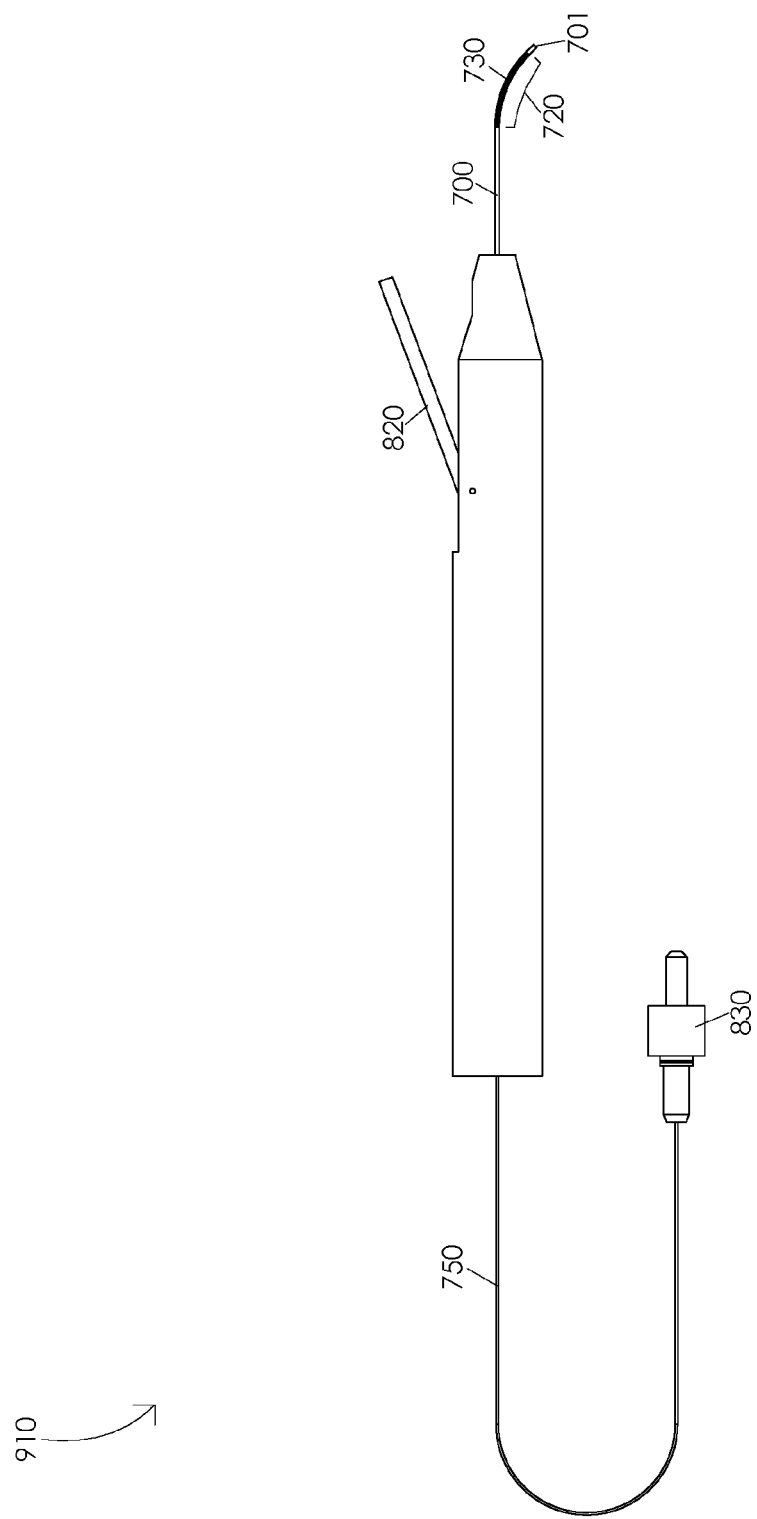

FIG. 9B illustrates an optic fiber in a first curved position 910. Illustratively, an actuation of actuation lever 820, e.g., in a clockwise direction about pivot pin 810, may be configured to gradually curve optic fiber 750. For example, an actuation of actuation lever 820, e.g., due to an application of a force to actuation lever 820, may be configured to gradually curve optic fiber 750. In one or more embodiments, an application of a force to actuation lever 820 may be configured to gradually curve optic fiber 750 from a straight optic fiber 900 to an optic fiber in a first curved position 910. Illustratively, an application of a force to actuation lever 820 may be configured to gradually retract wire 740 relative to housing tube 700. In one or more embodiments, a gradual retraction of wire 740 relative to housing tube 700 may be configured to cause wire 740 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750, e.g., from a straight optic fiber 900 to an optic fiber in a first curved position 910. In one or more embodiments, a line tangent to optic fiber distal end 751 may intersect a line tangent to housing tube proximal end 702 at a first angle, e.g., when optic fiber 750 comprises an optic fiber in a first curved position 910. Illustratively, the first angle may comprise any angle greater than zero degrees. For example, the first angle may comprise a 45 degree angle.

Figure 9C:
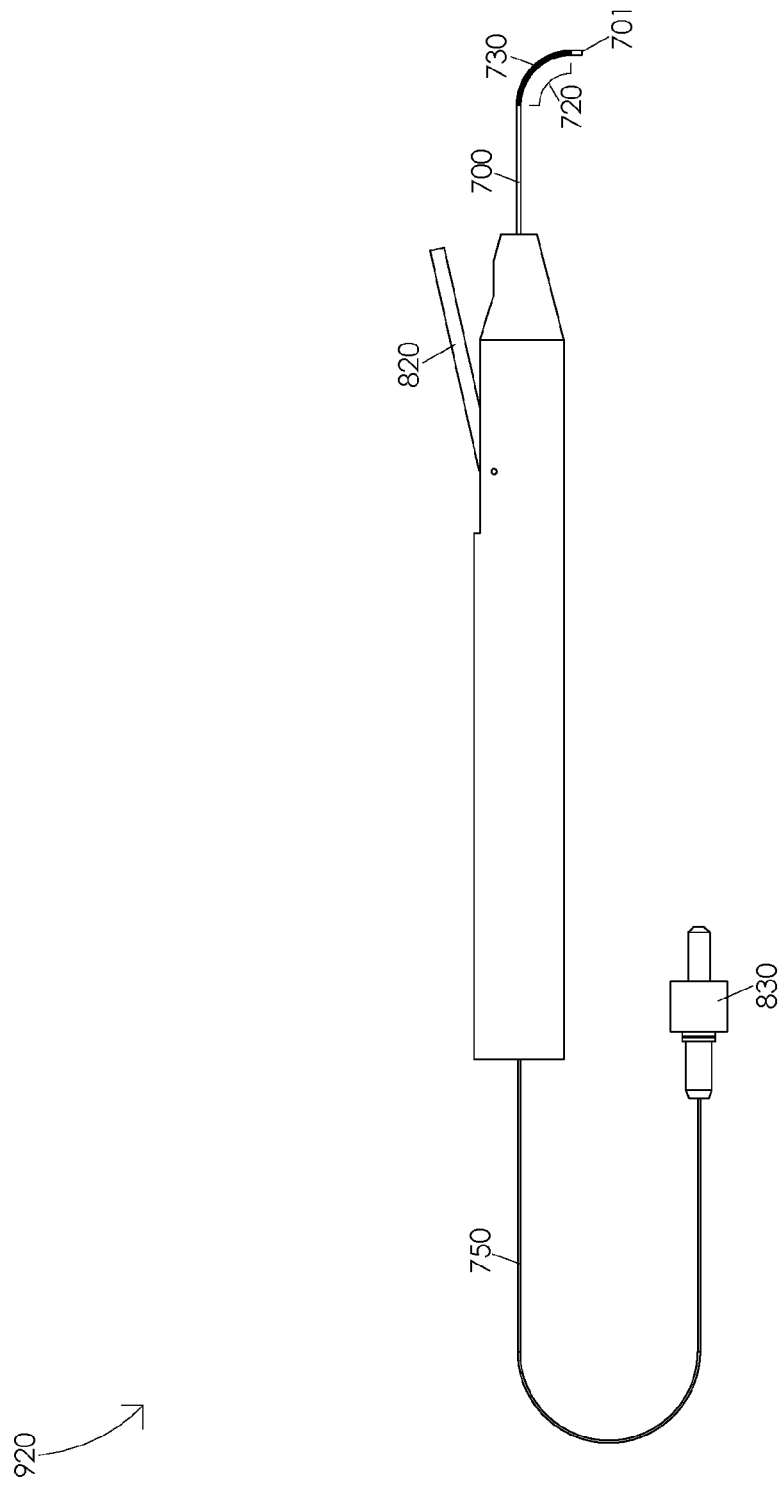

FIG. 9C illustrates an optic fiber in a second curved position 920. Illustratively, an actuation of actuation lever 820, e.g., in a clockwise direction about pivot pin 810, may be configured to gradually curve optic fiber 750. For example, an actuation of actuation lever 820, e.g., due to an application of a force to actuation lever 820, may be configured to gradually curve optic fiber 750. In one or more embodiments, an application of a force to actuation lever 820 may be configured to gradually curve optic fiber 750 from an optic fiber in a first curved position 910 to an optic fiber in a second curved position 920. Illustratively, an application of a force to actuation lever 820 may be configured to gradually retract wire 740 relative to housing tube 700. In one or more embodiments, a gradual retraction of wire 740 relative to housing tube 700 may be configured to cause wire 740 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750, e.g., from an optic fiber in a first curved position 910 to an optic fiber in a second curved position 920. In one or more embodiments, a line tangent to optic fiber distal end 751 may intersect a line tangent to housing tube proximal end 702 at a second angle, e.g., when optic fiber 750 comprises an optic fiber in a second curved position 920. Illustratively, the second angle may comprise any angle greater than the first angle. For example, the second angle may comprise a 90 degree angle.

Figure 9D:
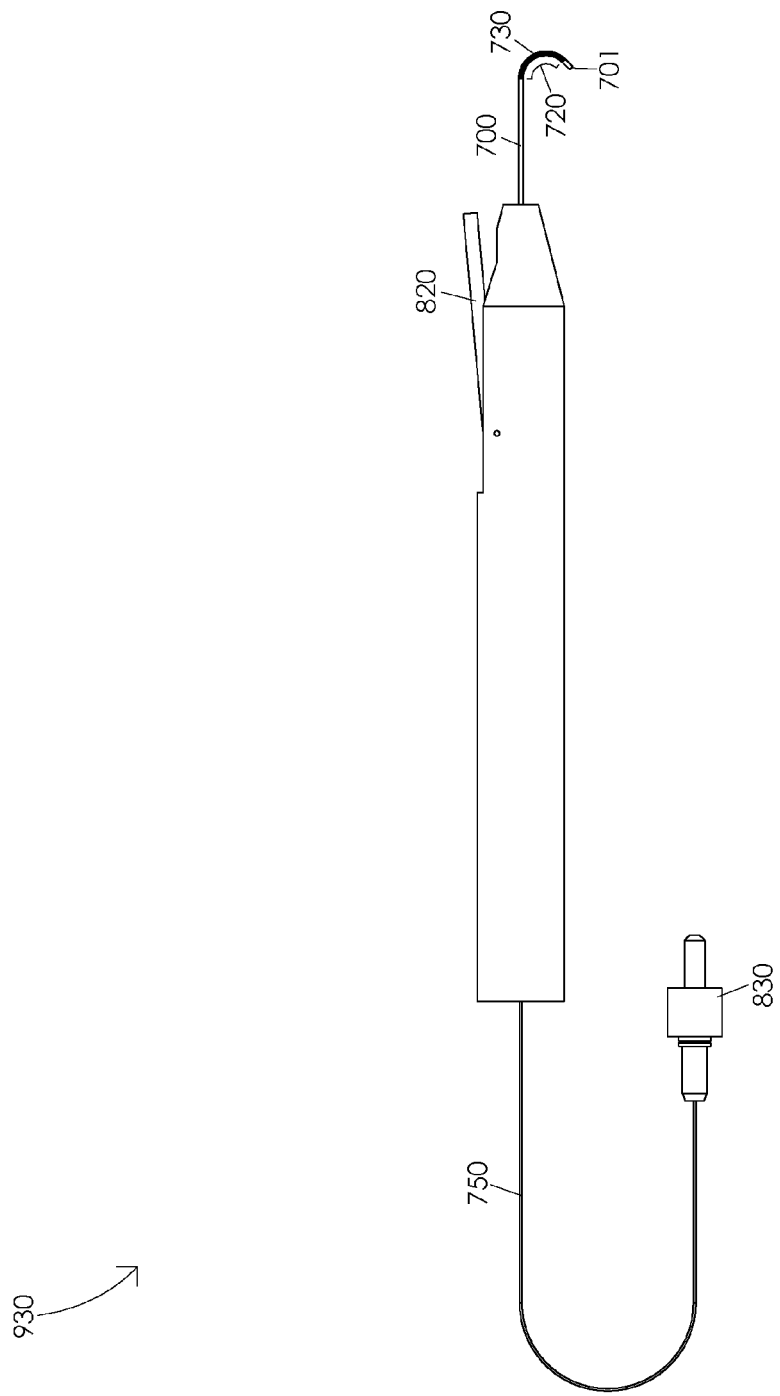

FIG. 9D illustrates an optic fiber in a third curved position 930. Illustratively, an actuation of actuation lever 820, e.g., in a clockwise direction about pivot pin 810, may be configured to gradually curve optic fiber 750. For example, an actuation of actuation lever 820, e.g., due to an application of a force to actuation lever 820, may be configured to gradually curve optic fiber 750. In one or more embodiments, an application of a force to actuation lever 820 may be configured to gradually curve optic fiber 750 from an optic fiber in a second curved position 920 to an optic fiber in a third curved position 930. Illustratively, an application of a force to actuation lever 820 may be configured to gradually retract wire 740 relative to housing tube 700. In one or more embodiments, a gradual retraction of wire 740 relative to housing tube 700 may be configured to cause wire 740 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750, e.g., from an optic fiber in a second curved position 920 to an optic fiber in a third curved position 930. In one or more embodiments, a line tangent to optic fiber distal end 751 may intersect a line tangent to housing tube proximal end 702 at a third angle, e.g., when optic fiber 750 comprises an optic fiber in a third curved position 930. Illustratively, the third angle may comprise any angle greater than the second angle. For example, the third angle may comprise a 135 degree angle.

Figure 9E:
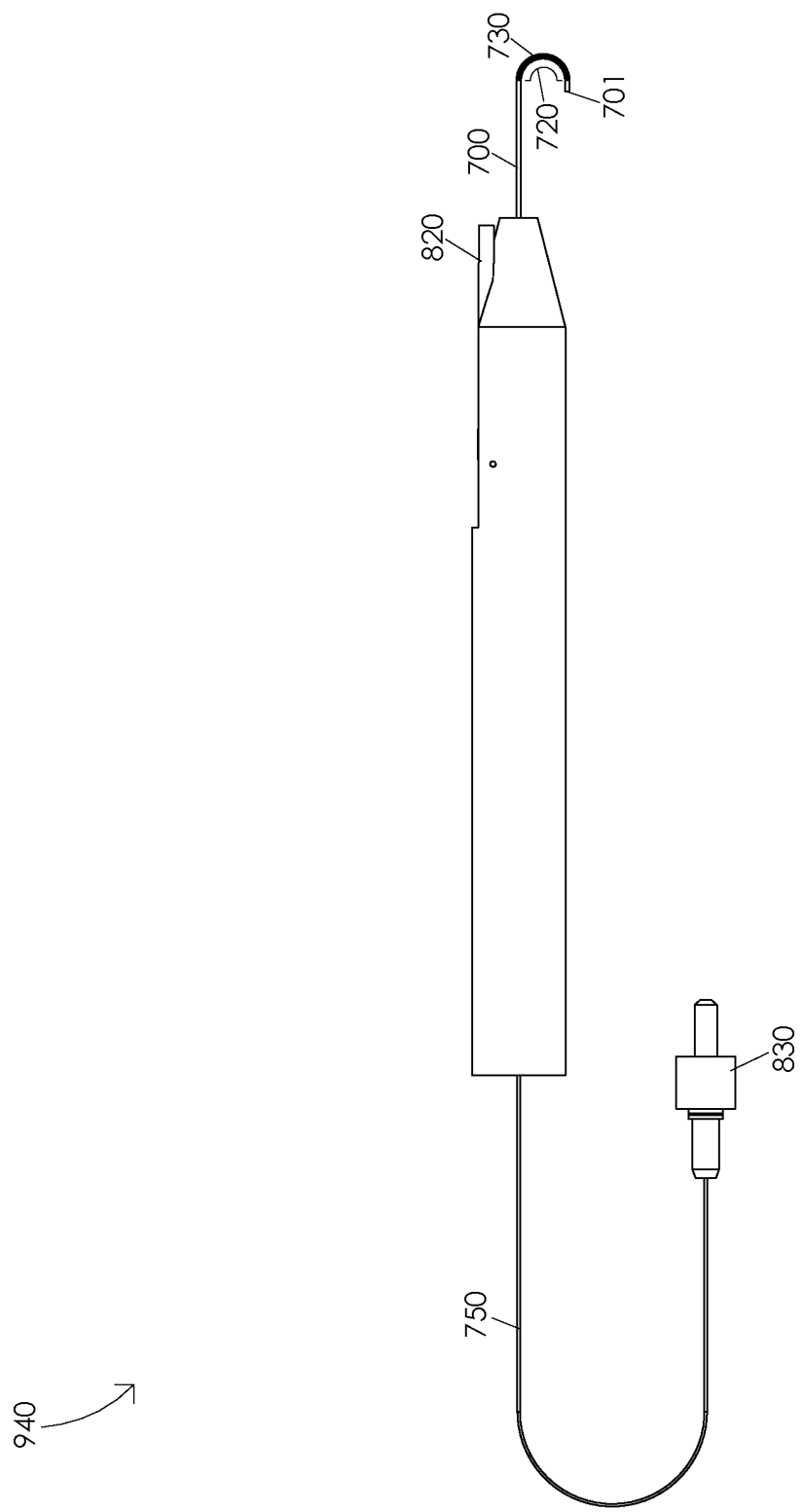

FIG. 9E illustrates an optic fiber in a fourth curved position 940. Illustratively, an actuation of actuation lever 820, e.g., in a clockwise direction about pivot pin 810, may be configured to gradually curve optic fiber 750. For example, an actuation of actuation lever 820, e.g., due to an application of a force to actuation lever 820, may be configured to gradually curve optic fiber 750. In one or more embodiments, an application of a force to actuation lever 820 may be configured to gradually curve optic fiber 750 from an optic fiber in a third curved position 930 to an optic fiber in a forth curved position 940. Illustratively, an application of a force to actuation lever 820 may be configured to gradually retract wire 740 relative to housing tube 700. In one or more embodiments, a gradual retraction of wire 740 relative to housing tube 700 may be configured to cause wire 740 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750, e.g., from an optic fiber in a third curved position 930 to an optic fiber in a fourth curved position 940. For example, a line tangent to optic fiber distal end 751 may be parallel to a line tangent to housing tube proximal end 702, e.g., when optic fiber 750 comprises an optic fiber in a fourth curved position 940.

In one or more embodiments, one or more properties of a steerable laser probe may be adjusted to attain one or more desired steerable laser probe features. For example, a stiffness of first housing tube portion 720 or a stiffness of second housing tube portion 730 may be adjusted to vary an amount of actuation of actuation lever 820 configured to curve housing tube 700 to a particular curved position. Illustratively, a material comprising first housing tube portion 720 or a material comprising second housing tube portion 730 may be adjusted to vary an amount of actuation of actuation lever 820 configured to curve housing tube 700 to a particular curved position.

In one or more embodiments, a number of apertures in housing tube 700 may be adjusted to vary an amount of actuation of actuation lever 820 configured to curve housing tube 700 to a particular curved position. Illustratively, a location of one or more apertures in housing tube 700 may be adjusted to vary an amount of actuation of actuation lever 820 configured to curve housing tube 700 to a particular curved position. In one or more embodiments, a geometry of one or more apertures in housing tube 700 may be adjusted to vary an amount of actuation of actuation lever 820 configured to curve housing tube 700 to a particular curved position. Illustratively, a geometry of one or more apertures in housing tube 700 may be uniform, e.g., each aperture of the one or more apertures may have a same geometry. In one or more embodiments, a geometry of one or more apertures in housing tube 700 may be non-uniform, e.g., a first aperture in housing tube 700 may have a first geometry and a second aperture in housing tube 700 may have a second geometry.

Illustratively, a geometry or shape of actuation lever 820 may be adjusted to vary an amount actuation of actuation lever 820 configured to curve housing tube 700 to a particular curved position. In one or more embodiments, one or more locations within housing tube 700 wherein wire 740 may be fixed to an inner portion of housing tube 700 may be adjusted to vary an amount of actuation of actuation lever 820 configured to curve housing tube 700 to a particular curved position. Illustratively, a portion of wire 740 may be fixed to an outer portion of housing tube 700. In one or more embodiments, a portion of wire 740 may be looped around a portion of housing tube 700. For example, wire proximal loop 742 may be adjusted to comprise a straight portion of wire 740. Illustratively, a portion of housing tube 700 may comprise an access window, e.g., configured to allow access to an inner portion of housing tube 700. In one or more embodiments, a portion of housing tube 700 may comprise an access window, e.g., configured to allow access to a portion of optic fiber 750 or a portion of wire 740. Illustratively, at least a portion of optic fiber 750 may be enclosed in an optic fiber sleeve configured to, e.g., protect optic fiber 750, vary a stiffness of optic fiber 750, vary an optical property of optic fiber 750, etc.

In one or more embodiments, a stiffness of first housing tube portion 720 or a stiffness of second housing tube portion 730 may be adjusted to vary a bend radius of housing tube 700. Illustratively, a stiffness of first housing tube portion 720 or a stiffness of second housing tube portion 730 may be adjusted to vary a radius of curvature of housing tube 700, e.g., when housing tube 700 is in a particular curved position. In one or more embodiments, a number of apertures in housing tube 700 may be adjusted to vary a bend radius of housing tube 700. Illustratively, a number of apertures in housing tube 700 may be adjusted to vary a radius of curvature of housing tube 700, e.g., when housing tube 700 is in a particular curved position. In one or more embodiments, a location or a geometry of one or more apertures in housing tube 700 may be adjusted to vary a bend radius of housing tube 700. Illustratively, a location or a geometry of one or more apertures in housing tube 700 may be adjusted to vary a radius of curvature of housing tube 700, e.g., when housing tube 700 is in a particular curved position.

Figure 10A:
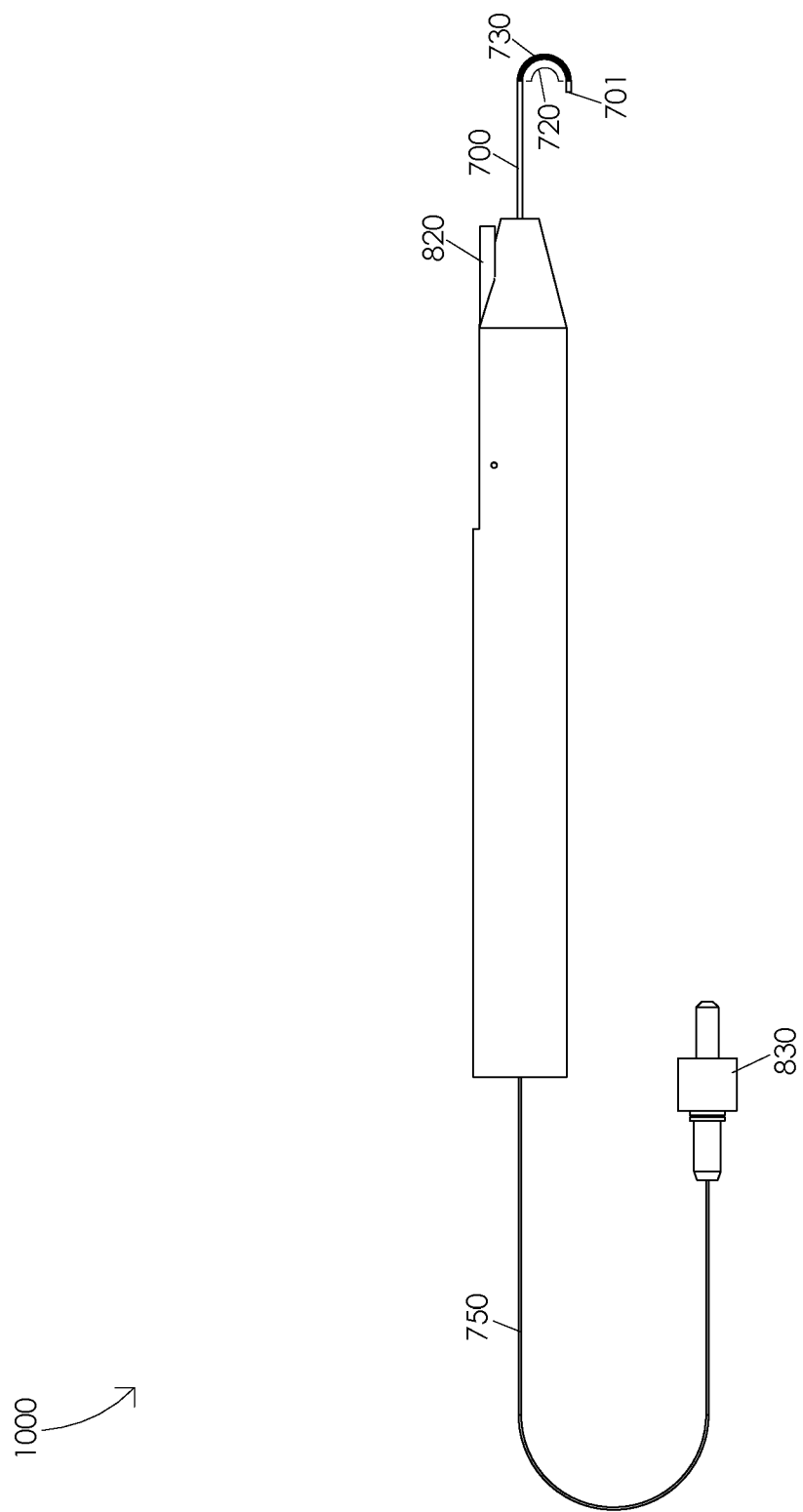
FIGS. 10A, 10B, 10C, 10D, and 10E illustrate a gradual straightening of an optic fiber.

FIGS. 10A, 10B, 10C, 10D, and 10E illustrate a gradual straightening of an optic fiber 750. FIG. 10A illustrates a fully curved optic fiber 1000. In one or more embodiments, optic fiber 750 may comprise a fully curved optic fiber 1000, e.g., when actuation lever proximal end 822 is fully retracted relative to handle base 610. Illustratively, optic fiber 750 may comprise a fully curved optic fiber 1000, e.g., when first housing tube portion 720 is fully compressed. In one or more embodiments, a line tangent to optic fiber distal end 751 may be parallel to a line tangent to housing tube proximal end 702, e.g., when optic fiber 750 comprises a fully curved optic fiber 1000.

Figure 10B:
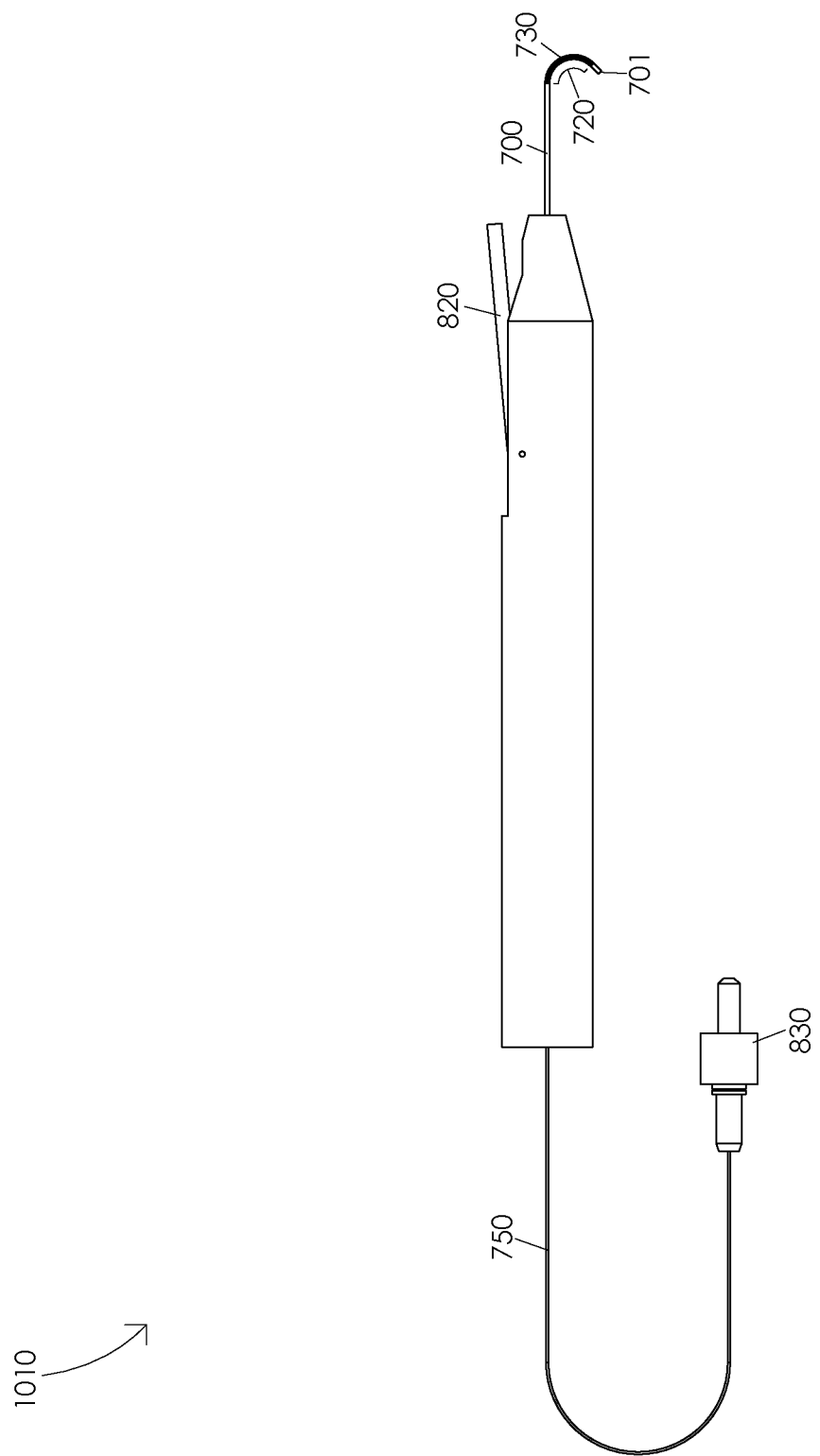

FIG. 10B illustrates an optic fiber in a first partially straightened position 1010. Illustratively, an actuation of actuation lever 820, e.g., in a counter-clockwise direction about pivot pin 810, may be configured to gradually straighten optic fiber 750. For example, an actuation of actuation lever 820, e.g., due to a reduction of a force applied to actuation lever 820, may be configured to gradually straighten optic fiber 750. In one or more embodiments, a reduction of a force applied to actuation lever 820 may be configured to gradually straighten optic fiber 750 from a fully curved optic fiber 1000 to an optic fiber in a first partially straightened position 1010. Illustratively, a reduction of a force applied to actuation lever 820 may be configured to gradually extend wire 740 relative to housing tube 700. In one or more embodiments, a gradual extension of wire 740 relative to housing tube 700 may be configured to cause wire 740 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750, e.g., from a fully curved optic fiber 1000 to an optic fiber in a first partially straightened position 1010. In one or more embodiments, a line tangent to optic fiber distal end 751 may intersect a line tangent to housing tube proximal end 702 at a first partially straightened angle, e.g., when optic fiber 750 comprises an optic fiber in a first partially straightened position 1010. Illustratively, the first partially straightened angle may comprise any angle less than 180 degrees. For example, the first partially straightened angle may comprise a 135 degree angle.

Figure 10C:
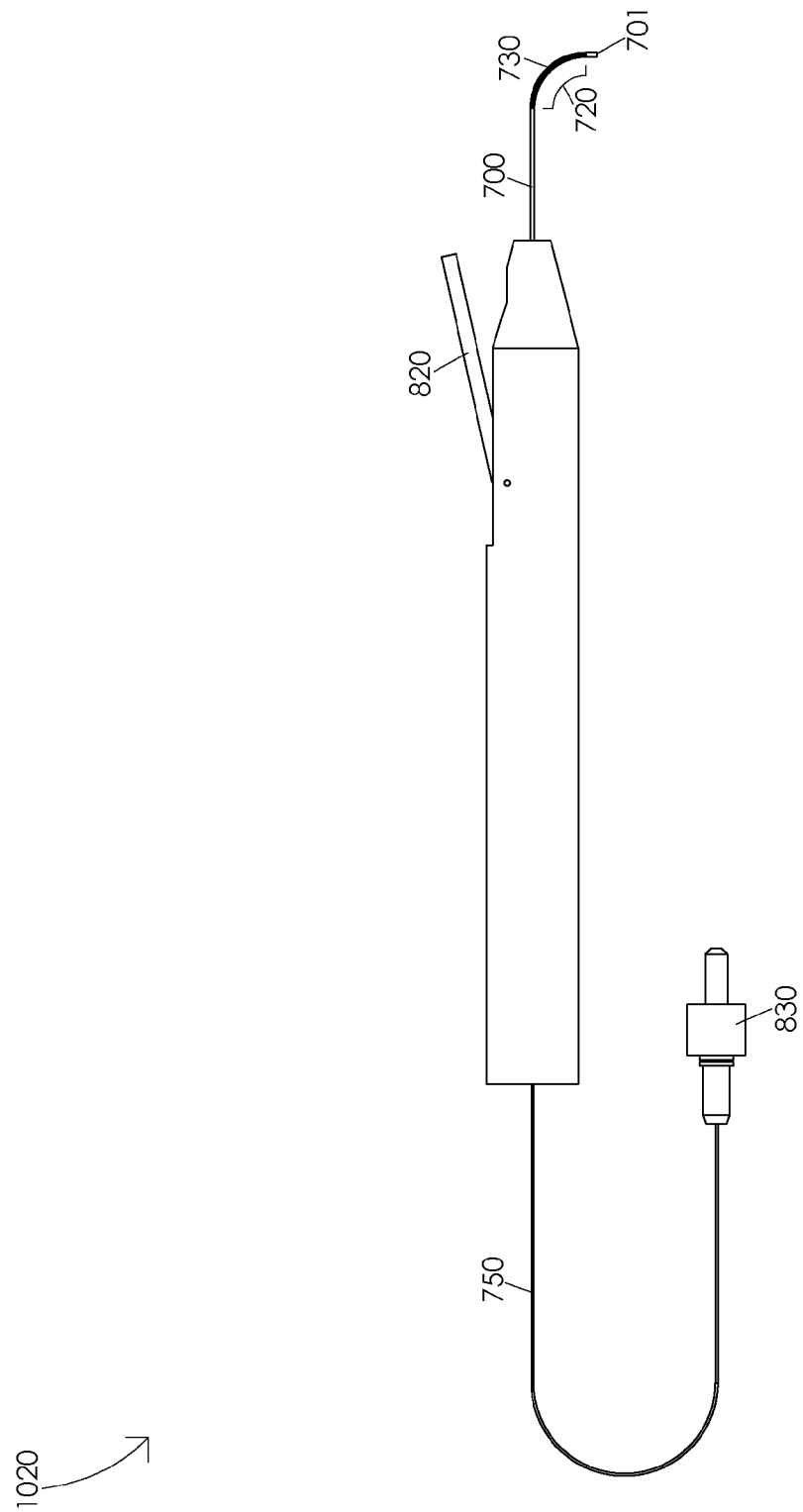

FIG. 10C illustrates an optic fiber in a second partially straightened position 1020. Illustratively, an actuation of actuation lever 820, e.g., in a counter-clockwise direction about pivot pin 810, may be configured to gradually straighten optic fiber 750. For example, an actuation of actuation lever 820, e.g., due to a reduction of a force applied to actuation lever 820, may be configured to gradually straighten optic fiber 750. In one or more embodiments, a reduction of a force applied to actuation lever 820 may be configured to gradually straighten optic fiber 750 from an optic fiber in a first partially straightened position 1010 to an optic fiber in a second partially straightened position 1020. Illustratively, a reduction of a force applied to actuation lever 820 may be configured to gradually extend wire 740 relative to housing tube 700. In one or more embodiments, a gradual extension of wire 740 relative to housing tube 700 may be configured to cause wire 740 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750, e.g., from an optic fiber in a first partially straightened position 1010 to an optic fiber in a second partially straightened position 1020. In one or more embodiments, a line tangent to optic fiber distal end 751 may intersect a line tangent to housing tube proximal end 702 at a second partially straightened angle, e.g., when optic fiber 750 comprises an optic fiber in a second partially straightened position 1020. Illustratively, the second partially straightened angle may comprise any angle less than the first partially straightened angle. For example, the second partially straightened angle may comprise a 90 degree angle.

Figure 10D:
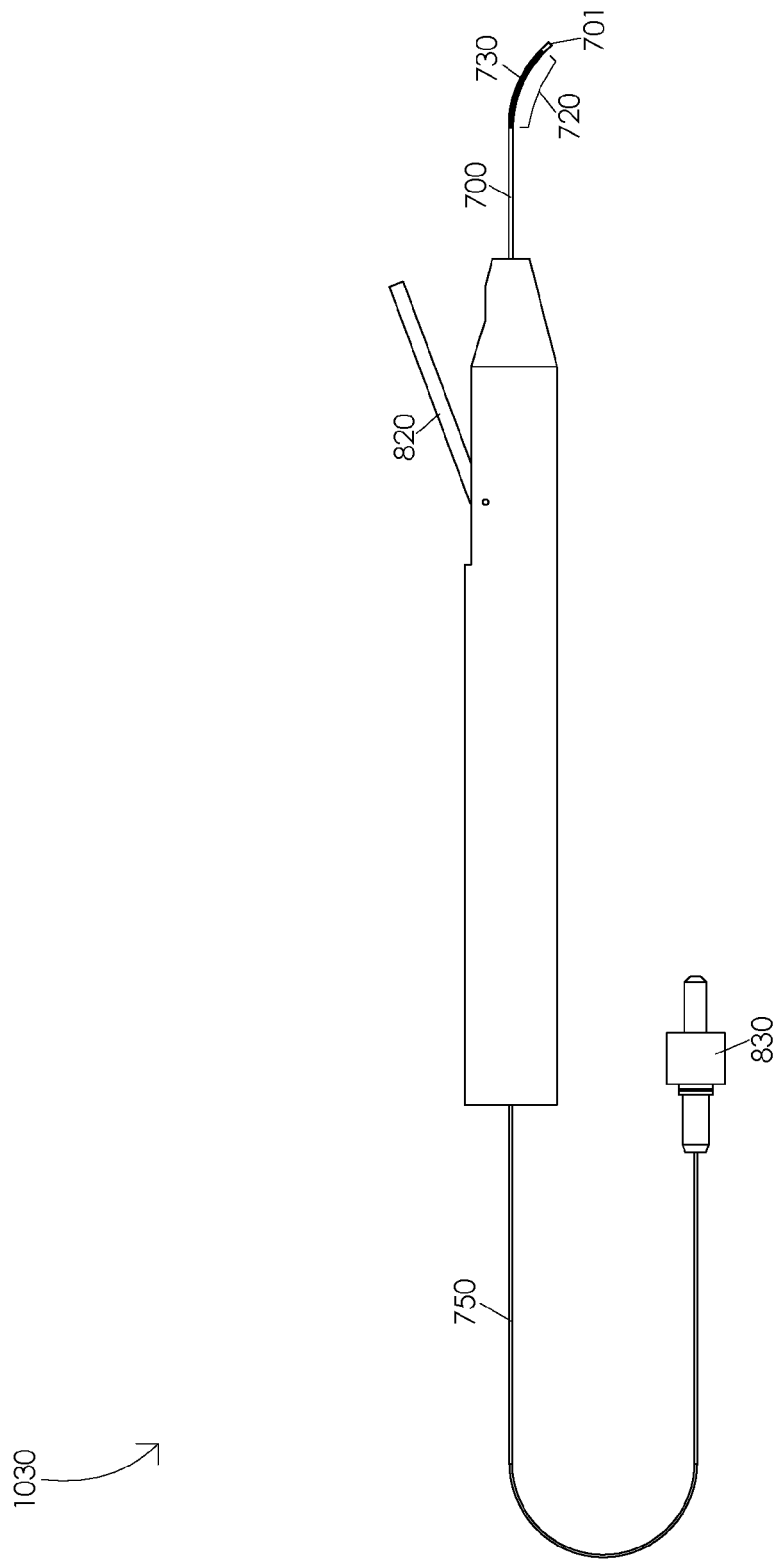

FIG. 10D illustrates an optic fiber in a third partially straightened position 1030. Illustratively, an actuation of actuation lever 820, e.g., in a counter-clockwise direction about pivot pin 810, may be configured to gradually straighten optic fiber 750. For example, an actuation of actuation lever 820, e.g., due to a reduction of a force applied to actuation lever 820, may be configured to gradually straighten optic fiber 750. In one or more embodiments, a reduction of a force applied to actuation lever 820 may be configured to gradually straighten optic fiber 750 from an optic fiber in a second partially straightened position 1020 to an optic fiber in a third partially straightened position 1030. Illustratively, a reduction of a force applied to actuation lever 820 may be configured to gradually extend wire 740 relative to housing tube 700. In one or more embodiments, a gradual extension of wire 740 relative to housing tube 700 may be configured to cause wire 740 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750, e.g., from an optic fiber in a second partially straightened position 1020 to an optic fiber in a third partially straightened position 1030. In one or more embodiments, a line tangent to optic fiber distal end 751 may intersect a line tangent to housing tube proximal end 702 at a third partially straightened angle, e.g., when optic fiber 750 comprises an optic fiber in a third partially straightened position 1030. Illustratively, the third partially straightened angle may comprise any angle less than the second partially straightened angle. For example, the third partially straightened angle may comprise a 45 degree angle.

Figure 10E:
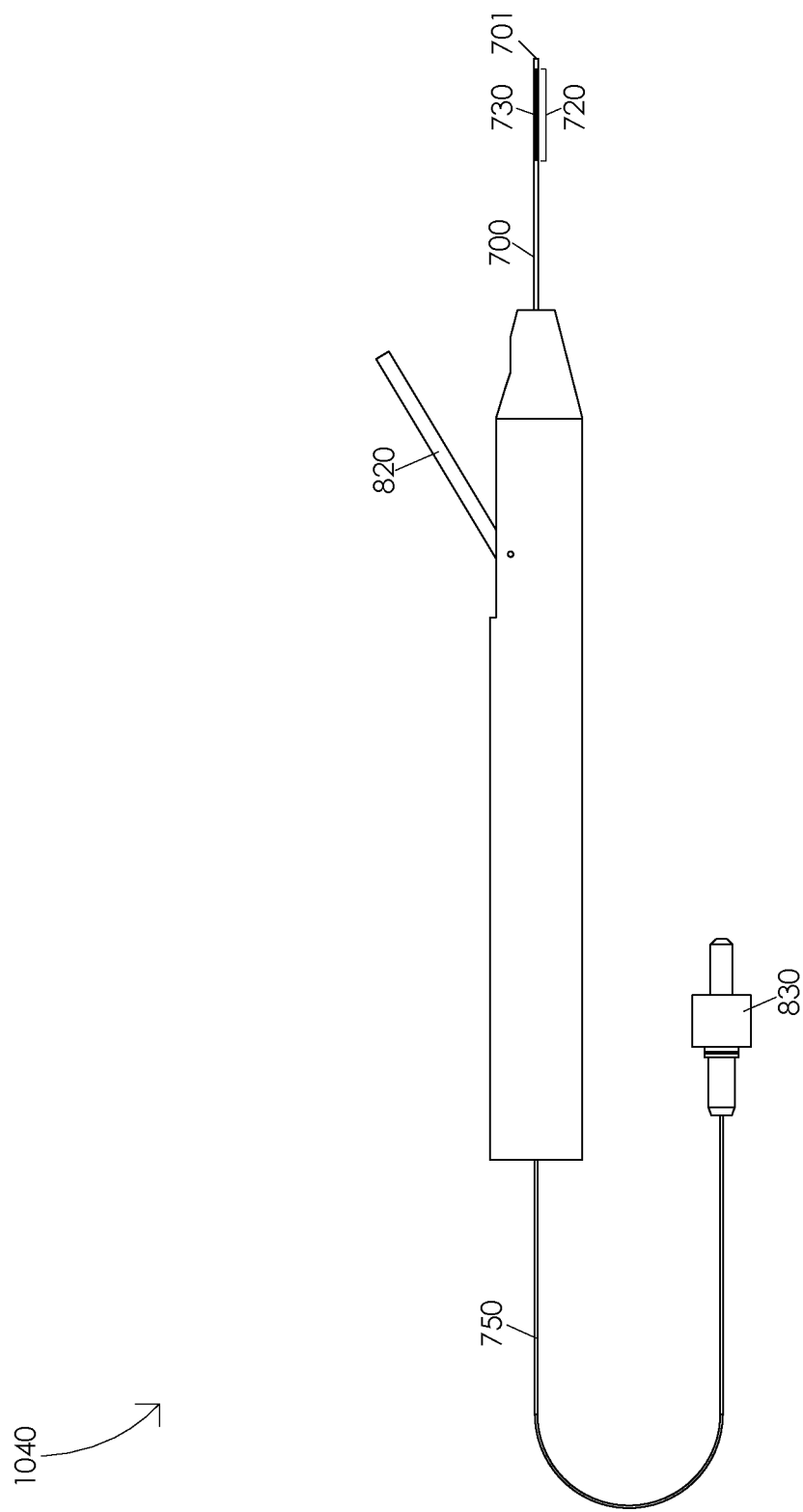

FIG. 10E illustrates an optic fiber in a fully straightened position 1040. Illustratively, an actuation of actuation lever 820, e.g., in a counter-clockwise direction about pivot pin 810, may be configured to gradually straighten optic fiber 750. For example, an actuation of actuation lever 820, e.g., due to a reduction of a force applied to actuation lever 820, may be configured to gradually straighten optic fiber 750. In one or more embodiments, a reduction of a force applied to actuation lever 820 may be configured to gradually straighten optic fiber 750 from an optic fiber in a third partially straightened position 1030 to an optic fiber in a fully straightened position 1040. Illustratively, a reduction of a force applied to actuation lever 820 may be configured to gradually extend wire 740 relative to housing tube 700. In one or more embodiments, a gradual extension of wire 740 relative to housing tube 700 may be configured to cause wire 740 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750, e.g., from an optic fiber in a third partially straightened position 1030 to an optic fiber in a fully straightened position 1040. In one or more embodiments, a line tangent to optic fiber distal end 751 may be parallel to a line tangent to housing tube proximal end 702, e.g., when optic fiber 750 comprises an optic fiber in a fully straightened position 1040.

Illustratively, a surgeon may aim optic fiber distal end 751 at any of a plurality of targets within an eye, e.g., to perform a photocoagulation procedure. In one or more embodiments, a surgeon may aim optic fiber distal end 751 at any target within a particular transverse plane of the inner eye by, e.g., rotating handle 600 to orient housing tube 700 in an orientation configured to cause a curvature of housing tube 700 within the particular transverse plane of the inner eye and varying an amount of actuation of actuation lever 820. Illustratively, a surgeon may aim optic fiber distal end 751 at any target within a particular sagittal plane of the inner eye by, e.g., rotating handle 600 to orient housing tube 700 in an orientation configured to cause a curvature of housing tube 700 within the particular sagittal plane of the inner eye and varying an amount of actuation of actuation lever 820. In one or more embodiments, a surgeon may aim optic fiber distal end 751 at any target within a particular frontal plane of the inner eye by, e.g., varying an amount of actuation of actuation lever 820 to orient a line tangent to optic fiber distal end 751 wherein the line tangent to optic fiber distal end 751 is within the particular frontal plane of the inner eye and rotating handle 600. Illustratively, a surgeon may aim optic fiber distal end 751 at any target located outside of the particular transverse plane, the particular sagittal plane, and the particular frontal plane of the inner eye, e.g., by varying a rotational orientation of handle 600 and varying an amount of actuation of actuation lever 820. In one or more embodiments, a surgeon may aim optic fiber distal end 751 at any target of a plurality of targets within an eye, e.g., without increasing a length of a portion of a steerable laser probe within the eye. Illustratively, a surgeon may aim optic fiber distal end 751 at any target of a plurality of targets within an eye, e.g., without decreasing a length of a portion of a steerable laser probe within the eye.

FIGS. 11A and 11B are schematic diagrams illustrating a handle 1100. FIG. 11A illustrates a top view of handle 1100. Illustratively, handle 1100 may comprise a handle distal end 1101 and a handle proximal end 1102. In one or more embodiments, handle 1100 may comprise a handle base 1110, an actuation channel 1120 having an actuation channel distal end 1121 and an actuation channel proximal end 1122, and a pivot pin housing 1130. FIG. 11B illustrates a cross-sectional view of handle 1100. Illustratively, handle 1100 may comprise a pulley mechanism housing 1135, an inner bore 1140, an inner bore distal chamber 1150, and an optic fiber guide 1160. Handle 1100 may be manufactured from any suitable material, e.g., polymers, metals, metal alloys, etc., or from any combination of suitable materials.

Figure 12:
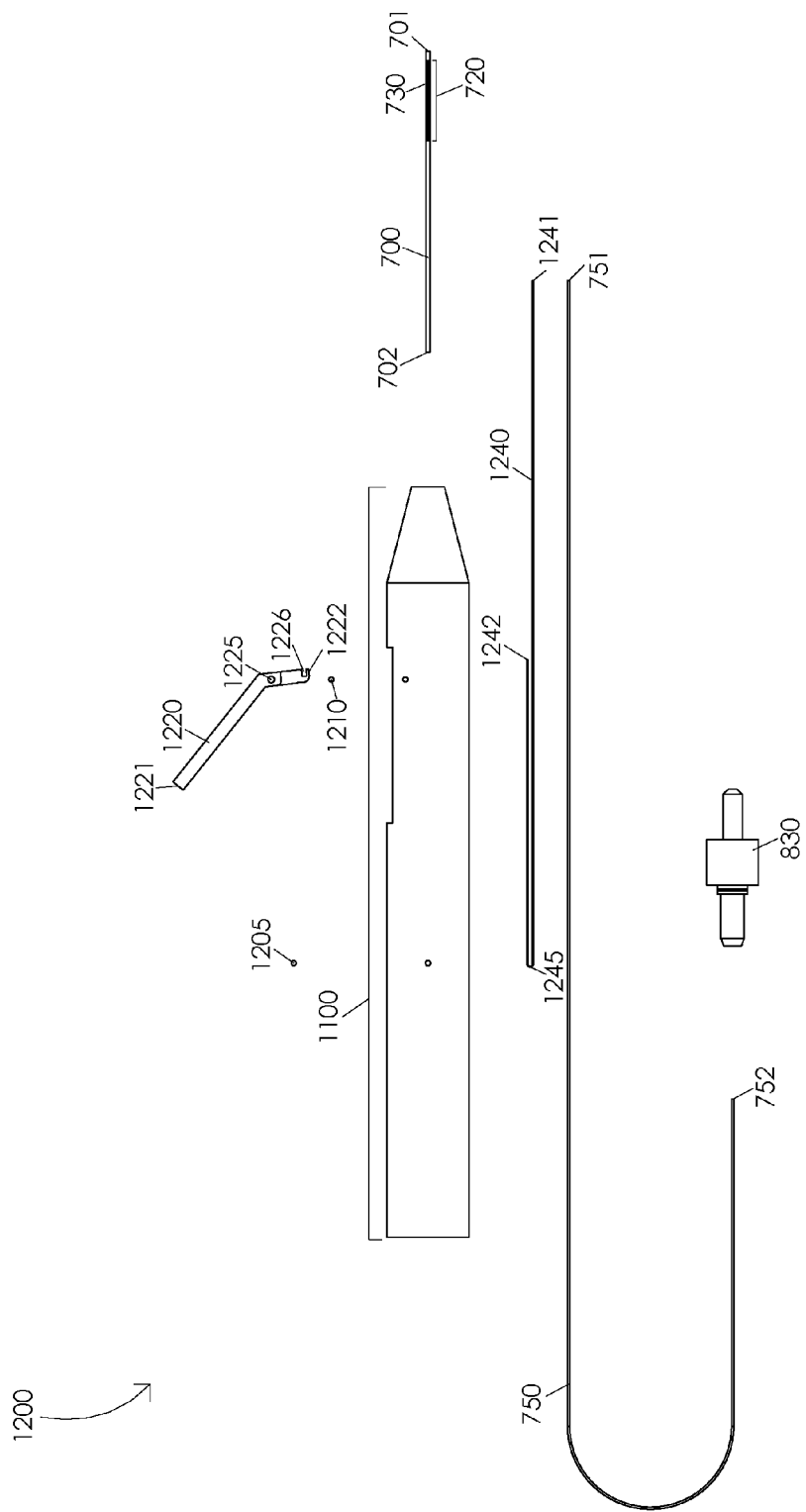
FIG. 12 is a schematic diagram illustrating an exploded view of a steerable laser probe assembly.

FIG. 12 is a schematic diagram illustrating an exploded view of a steerable laser probe assembly 1200. In one or more embodiments, a steerable laser probe assembly 1200 may comprise a handle 1100, a housing tube 700 having a housing tube distal end 701 and a housing tube proximal end 702, an optic fiber 750 having an optic fiber distal end 751 and an optic fiber proximal end 752, a pulley mechanism 1205, a pivot pin 1210, an actuation lever 1220 having an actuation lever distal end 1221 and an actuation lever proximal end 1222, a draw wire 1240 having a draw wire distal end 1241 and a draw wire proximal end 1242, and a light source interface 830. Illustratively, light source interface 830 may be configured to interface with optic fiber proximal end 752. In one or more embodiments, light source interface 830 may comprise a standard light source connector, e.g., an SMA connector.

Illustratively, actuation lever 1220 may comprise a pivot pin guide 1225. In one or more embodiments, pivot pin 1210 may be disposed within pivot pin housing 1130 and pivot pin guide 1225. Illustratively, pivot pin 1210 may be configured to fix a portion of actuation lever 1220 to a portion of handle 1100. In one or more embodiments, pivot pin 1210 may be fixed in a position within pivot pin housing 1130. For example, pivot pin 1210 may be fixed in a position within pivot pin housing 1130, e.g., by an adhesive or any other suitable fixation means.

Illustratively, housing tube 700 may be fixed to handle 1100, e.g., housing tube proximal end 702 may be fixed to handle distal end 1101. In one or more embodiments, housing tube 700 may be fixed to handle 1100, e.g., by an adhesive or any suitable fixation means. Illustratively, housing tube 700 may comprise a first housing tube portion 720 having a first stiffness and a second housing tube portion 730 having a second stiffness. In one or more embodiments, the second stiffness may be greater than the first stiffness.

Illustratively, pulley mechanism 1205 may be disposed within pulley mechanism housing 1135. In one or more embodiments, pulley mechanism 1205 may be configured to change a direction of an applied force, e.g., a force applied to draw wire 1240. For example, pulley mechanism 1205 may comprise any suitable mechanism configured to change a direction of an applied force. Illustratively, pulley mechanism 1205 may be configured to change a point of application of an applied force, e.g., by changing a direction of an applied force. For example, pulley mechanism 1205 may be configured to change a direction and a point of application of an applied force, e.g., a force applied to draw wire 1240. In one or more embodiments, pulley mechanism 1205 may comprise a rod configured to change a direction of an applied force, e.g., a force applied to draw wire 1240. For example, pulley mechanism 1205 may comprise a rod configured to change a point of application of an applied force, e.g., a force applied to draw wire 1240. Illustratively, pulley mechanism 1205 may comprise one or more channels configured to, e.g., interface with a portion of draw wire 1240. In one or more embodiments, a portion of pulley mechanism 1205 may be coated with a lubricant, e.g., Teflon, configured to minimize a force of friction between pulley mechanism 1205 and draw wire 1240. Illustratively, pulley mechanism 1205 may be configured to rotate, e.g., to change a direction of an applied force, or a portion of pulley mechanism 1205, e.g., a wheel, may be configured to rotate, e.g., to change a direction of an applied force. For example, pulley mechanism 1205 or a portion of pulley mechanism 1205 may be configured to change a point of application of an applied force, e.g., a force applied to draw wire 1240. In one or more embodiments, pulley mechanism 1205 may be configured to remain in static equilibrium, e.g., not to rotate, to change a direction of an applied force, e.g., a force applied to draw wire 1240. For example, a change in a direction of an applied force may be configured to change one or more points of application of the applied force. Illustratively, a portion of pulley mechanism 1205 may be configured to house a portion of optic fiber 750.

In one or more embodiments, draw wire proximal end 1242 may be fixed to actuation lever proximal end 1222. Illustratively, draw wire proximal end 1242 may be fixed to actuation lever proximal end 1222, e.g., by an adhesive or any other suitable fixation means. Illustratively, actuation lever 1220 may comprise a draw wire proximal end housing 1226. In one or more embodiments, draw wire proximal end 1242 may be fixed within draw wire proximal end housing 1226, e.g., by an adhesive or any suitable fixation means.

Illustratively, a portion of draw wire 1240 may comprise a draw wire loop 1245. In one or more embodiments, pulley mechanism 1205 may be disposed within draw wire loop 1245. For example, draw wire loop 1245 may be looped around pulley mechanism 1205. Illustratively, draw wire 1240 may be disposed within inner bore 1140, actuation channel 1120, inner bore distal chamber 1150, optic fiber guide 1160, and housing tube 700. In one or more embodiments, draw wire 1240 may be disposed within housing tube 700 wherein draw wire distal end 1241 may be adjacent to housing tube distal end 701. Illustratively, draw wire 1240 may be disposed within housing tube 700 wherein a portion of draw wire 1240 may be adjacent to a portion of first housing tube portion 720. In one or more embodiments, a portion of draw wire 1240 may be fixed to an inner portion of housing tube 700, e.g., by a biocompatible adhesive or by any other suitable fixation means.

Illustratively, optic fiber 750 may be disposed within inner bore 1140, actuation channel 1120, inner bore distal chamber 1150, optic fiber guide 1160, and housing tube 700. In one or more embodiments, optic fiber 750 may be disposed within housing tube 700 wherein optic fiber distal end 751 may be adjacent to housing tube distal end 701. Illustratively, a portion of optic fiber 750 may be fixed to an inner portion of housing tube 700, e.g., by a biocompatible adhesive or by any other suitable fixation means.

In one or more embodiments, an application of a force to actuation lever 1220 may be configured to actuate actuation lever 1220, e.g., within actuation channel 1120. Illustratively, an application of a force to actuation lever 1220 may be configured to rotate actuation lever 1220 about pivot pin 1210. In one or more embodiments, an application of a force to actuation lever 1220 may be configured to rotate actuation lever distal end 1221 and actuation lever proximal end 1222 about pivot pin 1210, e.g., in a counter-clockwise direction. Illustratively, an application of a force to actuation lever 1220 may be configured to actuate actuation lever distal end 1221 towards handle proximal end 1102 and configured to actuate actuation lever proximal end 1222 away from handle proximal end 1102. For example, an application of a force to actuation lever 1220 may be configured to extend actuation lever proximal end 1222 relative to handle base 1110. In one or more embodiments, an application of a force to actuation lever 1220 may be configured to extend draw wire proximal end 1242 relative to handle proximal end 1102.

Illustratively, an actuation of actuation lever proximal end 1222 away from handle proximal end 1102, e.g., due to an application of a force to actuation lever 1220, may be configured to extend draw wire proximal end 1242 relative to handle proximal end 1102. For example, an actuation of actuation lever proximal end 1222 away from handle proximal end 1102 may be configured to pull draw wire proximal end 1242 away from handle proximal end 1102. In one or more embodiments, pulley mechanism 1205 may be configured to change a direction and a point of application of a force configured to extend draw wire proximal end 1242 relative to handle proximal end 1102. Illustratively, pulley mechanism may 1205 be configured to change a direction and a point of application of a force from a force configured to extend draw wire proximal end 1242 relative to handle proximal end 1102 to a force configured to retract draw wire distal end 1241 relative to handle proximal end 1102. In one or more embodiments, an actuation of actuation lever proximal end 1222 away from handle proximal end 1102 may be configured to retract draw wire distal end 1241 towards handle proximal end 1102. Illustratively, an extension of actuation lever proximal end 1222 and draw wire proximal end 1242 relative to handle proximal end 1102 may be configured to retract draw wire 1240, e.g., to retract draw wire distal end 1241, relative to housing tube 700.

In one or more embodiments, a retraction of draw wire 1240 relative to housing tube 700 may be configured to cause draw wire 1240 to apply a compressive force to an inner portion of housing tube 700. Illustratively, an application of a compressive force to an inner portion of housing tube 700 may be configured to gradually compress a portion of housing tube 700, e.g., a first housing tube portion 720 of housing tube 700. In one or more embodiments, a gradual compression of a portion of housing tube 700 may be configured to cause housing tube 700 to gradually curve. Illustratively, a gradual curving of housing tube 700 may be configured to gradually curve optic fiber 750.

In one or more embodiments, a reduction of a force applied to actuation lever 1220 may be configured to actuate actuation lever 1220, e.g., within actuation channel 1120. Illustratively, a reduction of a force applied to actuation lever 1220 may be configured to rotate actuation lever 1220 about pivot pin 1210. In one or more embodiments, a reduction of a force applied to actuation lever 1220 may be configured to rotate actuation lever distal end 1221 and actuation lever proximal end 1222 about pivot pin 1210, e.g., in a clockwise direction. Illustratively, a reduction of a force applied to actuation lever 1220 may be configured to actuate actuation lever distal end 1221 away from handle proximal end 1102 and configured to actuate actuation lever proximal end 1222 towards proximal end 1102. For example, a reduction of a force applied to actuation lever 1220 may be configured to retract actuation lever proximal end 1222 relative to handle base 1110. In one or more embodiments, a reduction of a force applied to actuation lever 1220 may be configured to retract draw wire proximal end 1242 relative to handle proximal end 1102.

Illustratively, an actuation of actuation lever proximal end 1222 towards handle proximal end 1102, e.g., due to a reduction of a force applied to actuation lever 1220, may be configured to retract draw wire proximal end 1242 relative to handle proximal end 1102. In one or more embodiments, pulley mechanism 1205 may be configured to change a direction and a point of application of a force configured to retract draw wire proximal end 1242 relative to handle proximal end 1102. Illustratively, pulley mechanism 1205 be configured to change a direction and a point of application of a force from a force configured to retract draw wire proximal end 1242 relative to handle proximal end 1102 to a force configured to extend draw wire distal end 1241 relative to handle proximal end 1102. In one or more embodiments, an actuation of actuation lever proximal end 1222 towards handle proximal end 1102 may be configured to extend draw wire distal end 1241 away from handle proximal end 1102. Illustratively, a retraction of actuation lever proximal end 1222 and draw wire proximal end 1242 relative to handle proximal end 1102 may be configured to extend draw wire 1240, e.g., to extend draw wire distal end 1241, relative to housing tube 700.

In one or more embodiments, an extension of draw wire 1240 relative to housing tube 700 may be configured to cause draw wire 1240 to reduce a compressive force applied to an inner portion of housing tube 700. Illustratively, a reduction of a compressive force applied to an inner portion of housing tube 700 may be configured to gradually decompress a portion of housing tube 700, e.g., a first housing tube portion 720 of housing tube 700. In one or more embodiments, a gradual decompression of a portion of housing tube 700 may be configured to cause housing tube 700 to gradually straighten. Illustratively, a gradual straightening of housing tube 700 may be configured to gradually straighten optic fiber 750.

Figure 13A:
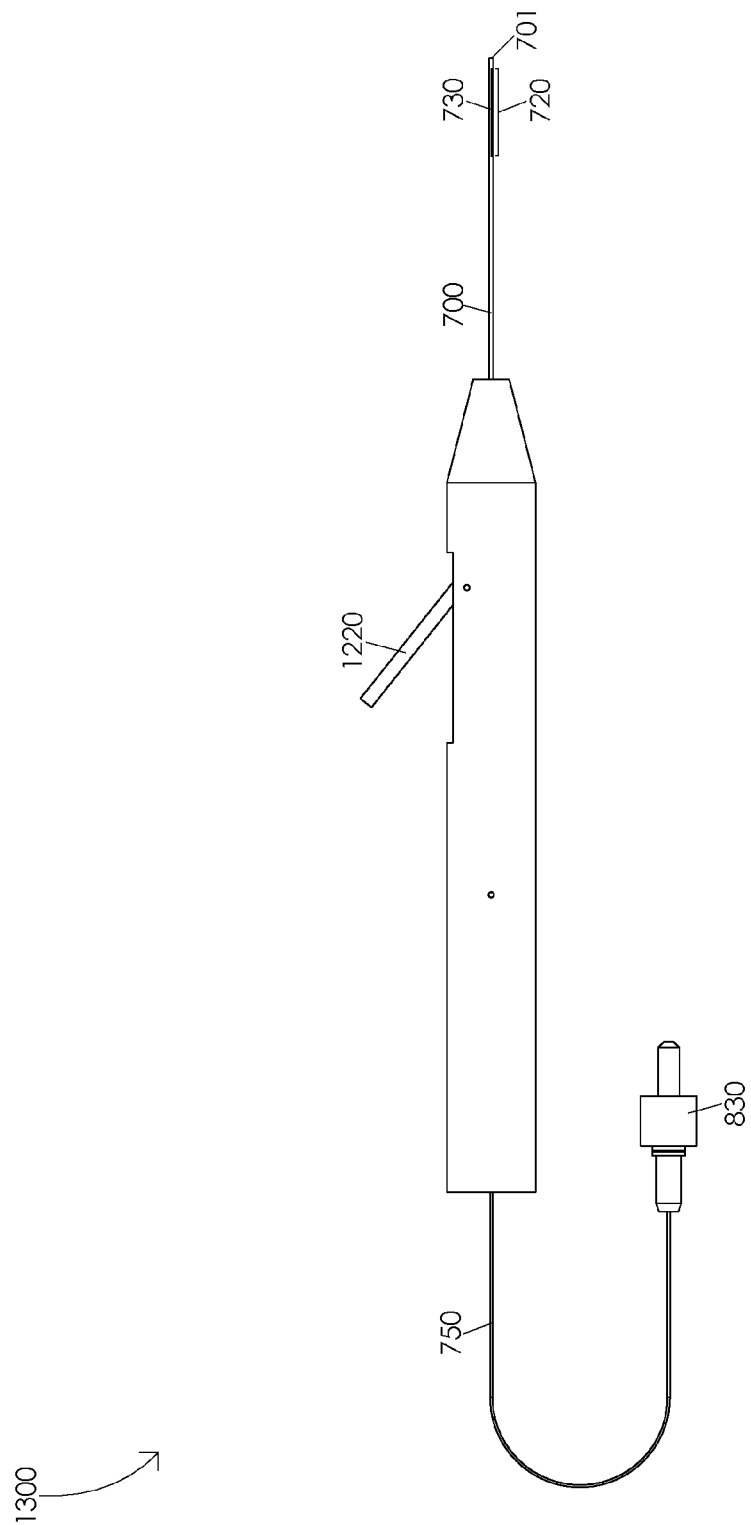
FIGS. 13A, 13B, 13C, 13D, and 13E illustrate a gradual curving of an optic fiber.

FIGS. 13A, 13B, 13C, 13D, and 13E illustrate a gradual curving of an optic fiber 750. FIG. 13A illustrates a straight optic fiber 1300. In one or more embodiments, optic fiber 750 may comprise a straight optic fiber 1300, e.g., when actuation lever proximal end 1222 is fully retracted relative to handle base 1110. Illustratively, optic fiber 750 may comprise a straight optic fiber 1300, e.g., when first housing tube portion 720 is fully decompressed. In one or more embodiments, a line tangent to optic fiber distal end 751 may be parallel to a line tangent to housing tube proximal end 702, e.g., when optic fiber 750 comprises a straight optic fiber 1300.

Figure 13B:
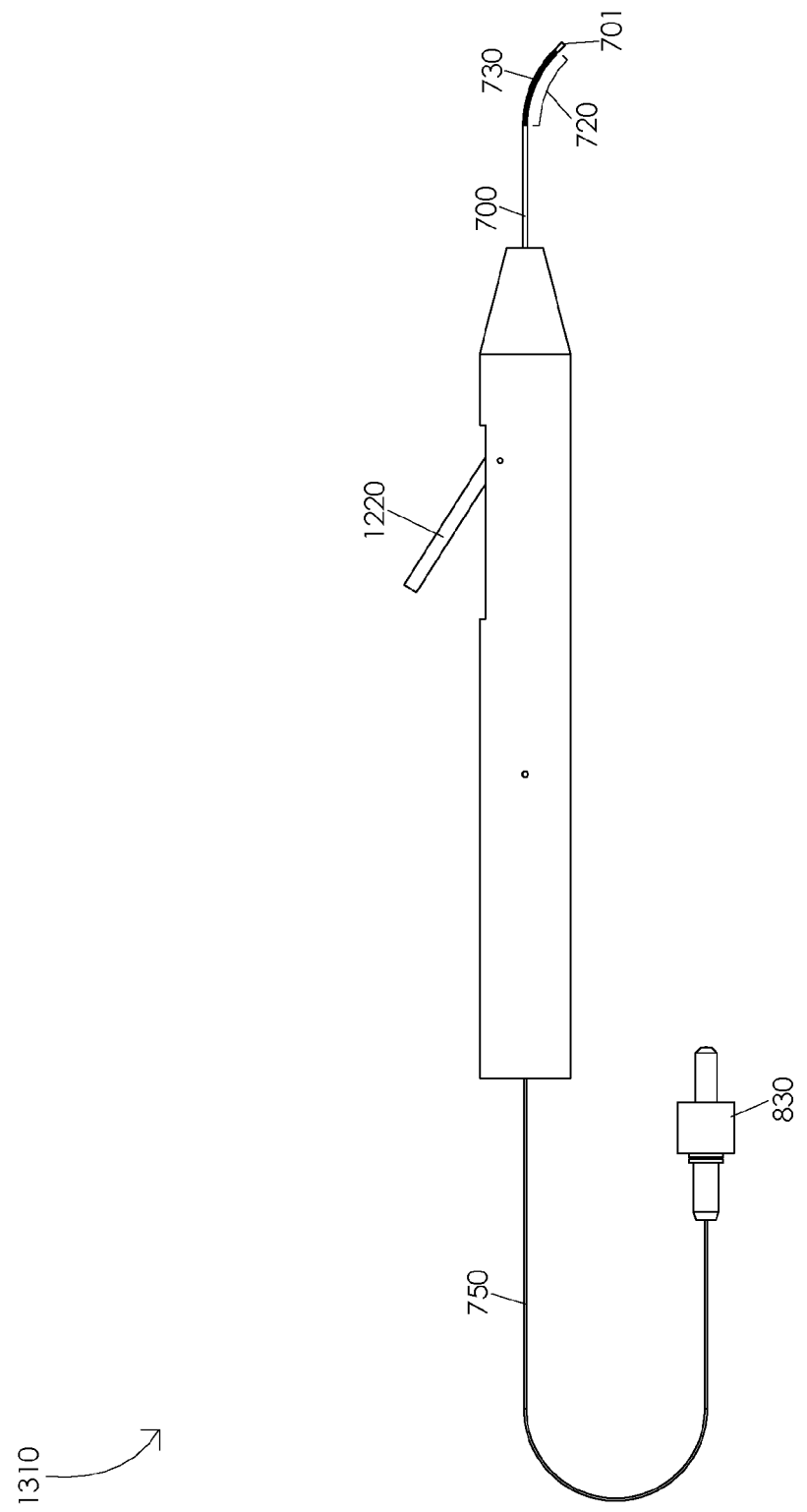

FIG. 13B illustrates an optic fiber in a first curved position 1310. Illustratively, an actuation of actuation lever 1220, e.g., in a counter-clockwise direction about pivot pin 1210, may be configured to gradually curve optic fiber 750. For example, an actuation of actuation lever 1220, e.g., due to an application of a force to actuation lever 1220, may be configured to gradually curve optic fiber 750. In one or more embodiments, an application of a force to actuation lever 1220 may be configured to gradually curve optic fiber 750 from a straight optic fiber 1300 to an optic fiber in a first curved position 1310. Illustratively, an application of a force to actuation lever 1220 may be configured to gradually retract draw wire 1240 relative to housing tube 700. In one or more embodiments, a gradual retraction of draw wire 1240 relative to housing tube 700 may be configured to cause draw wire 1240 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750, e.g., from a straight optic fiber 1300 to an optic fiber in a first curved position 1310. In one or more embodiments, a line tangent to optic fiber distal end 751 may intersect a line tangent to housing tube proximal end 702 at a first angle, e.g., when optic fiber 750 comprises an optic fiber in a first curved position 1310. Illustratively, the first angle may comprise any angle greater than zero degrees. For example, the first angle may comprise a 45 degree angle.

Figure 13C:
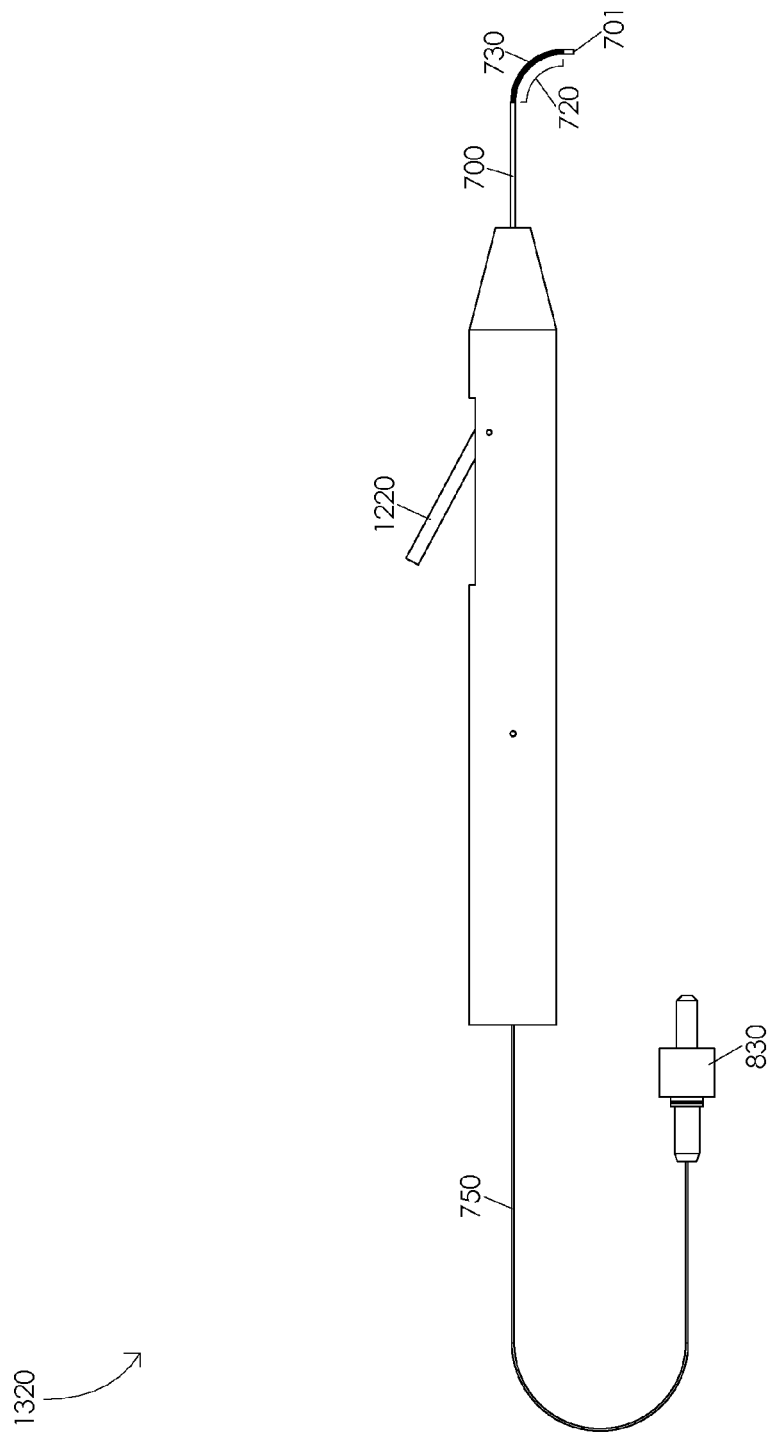

FIG. 13C illustrates an optic fiber in a second curved position 1320. Illustratively, an actuation of actuation lever 1220, e.g., in a counter-clockwise direction about pivot pin 1210, may be configured to gradually curve optic fiber 750. For example, an actuation of actuation lever 1220, e.g., due to an application of a force to actuation lever 1220, may be configured to gradually curve optic fiber 750. In one or more embodiments, an application of a force to actuation lever 1220 may be configured to gradually curve optic fiber 750 from an optic fiber in a first curved position 1310 to an optic fiber in a second curved position 1320. Illustratively, an application of a force to actuation lever 1220 may be configured to gradually retract draw wire 1240 relative to housing tube 700. In one or more embodiments, a gradual retraction of draw wire 1240 relative to housing tube 700 may be configured to cause draw wire 1240 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750, e.g., from an optic fiber in a first curved position 1310 to an optic fiber in a second curved position 1320. In one or more embodiments, a line tangent to optic fiber distal end 751 may intersect a line tangent to housing tube proximal end 702 at a second angle, e.g., when optic fiber 750 comprises an optic fiber in a second curved position 1320. Illustratively, the second angle may comprise any angle greater than the first angle. For example, the second angle may comprise a 90 degree angle.

Figure 13D:
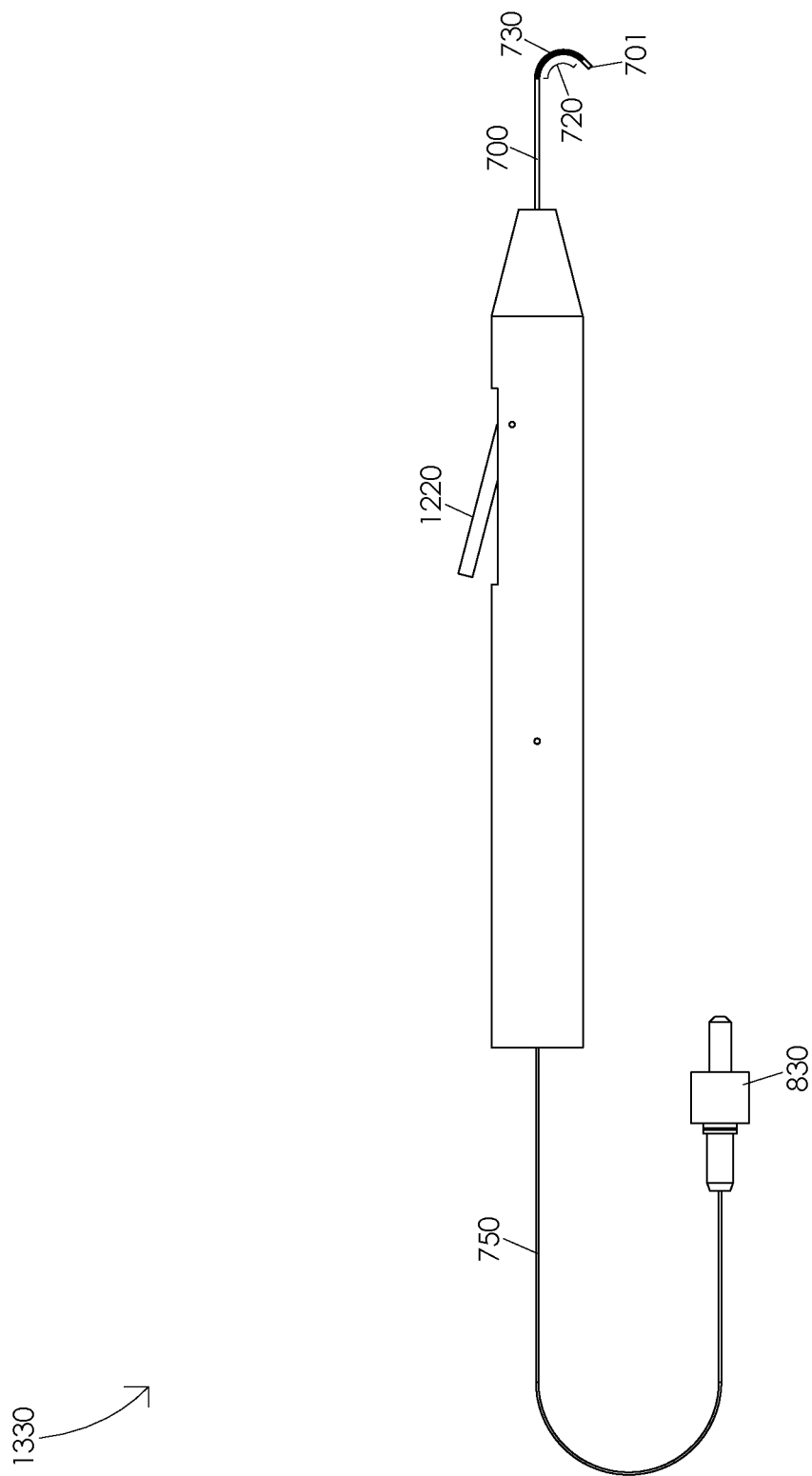

FIG. 13D illustrates an optic fiber in a third curved position 1330. Illustratively, an actuation of actuation lever 1220, e.g., in a counter-clockwise direction about pivot pin 1210, may be configured to gradually curve optic fiber 750. For example, an actuation of actuation lever 1220, e.g., due to an application of a force to actuation lever 1220, may be configured to gradually curve optic fiber 750. In one or more embodiments, an application of a force to actuation lever 1220 may be configured to gradually curve optic fiber 750 from an optic fiber in a second curved position 1320 to an optic fiber in a third curved position 1330. Illustratively, an application of a force to actuation lever 1220 may be configured to gradually retract draw wire 1240 relative to housing tube 700. In one or more embodiments, a gradual retraction of draw wire 1240 relative to housing tube 700 may be configured to cause draw wire 1240 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750, e.g., from an optic fiber in a second curved position 1320 to an optic fiber in a third curved position 1330. In one or more embodiments, a line tangent to optic fiber distal end 751 may intersect a line tangent to housing tube proximal end 702 at a third angle, e.g., when optic fiber 750 comprises an optic fiber in a third curved position 1330. Illustratively, the third angle may comprise any angle greater than the second angle. For example, the third angle may comprise a 135 degree angle.

Figure 13E:
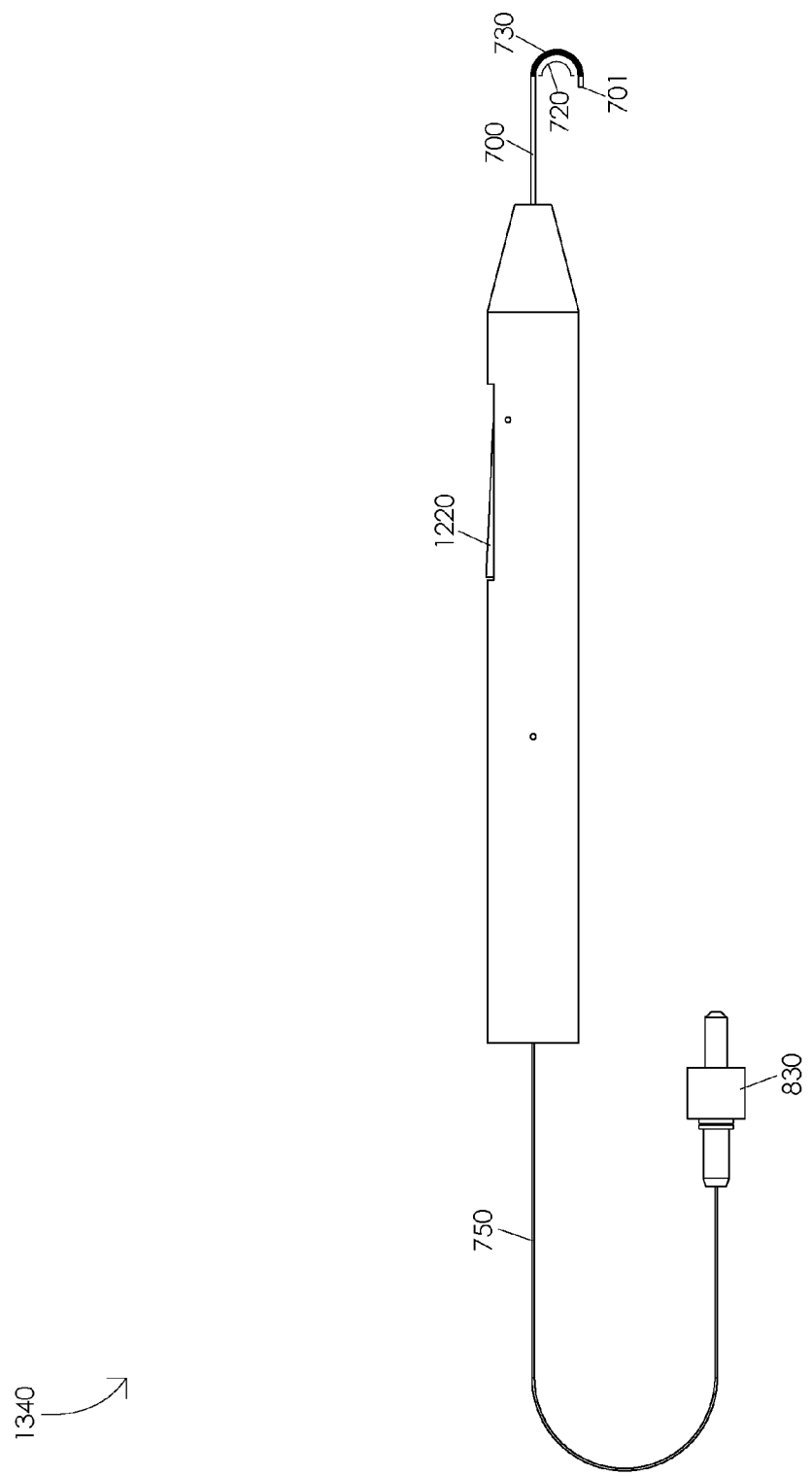

FIG. 13E illustrates an optic fiber in a fourth curved position 1340. Illustratively, an actuation of actuation lever 1220, e.g., in a counter-clockwise direction about pivot pin 1210, may be configured to gradually curve optic fiber 750. For example, an actuation of actuation lever 1220, e.g., due to an application of a force to actuation lever 1220, may be configured to gradually curve optic fiber 750. In one or more embodiments, an application of a force to actuation lever 1220 may be configured to gradually curve optic fiber 750 from an optic fiber in a third curved position 1330 to an optic fiber in a forth curved position 1340. Illustratively, an application of a force to actuation lever 1220 may be configured to gradually retract draw wire 1240 relative to housing tube 700. In one or more embodiments, a gradual retraction of draw wire 1240 relative to housing tube 700 may be configured to cause draw wire 1240 to apply a compressive force to an inner portion of housing tube 700. Illustratively, an application of a compressive force to an inner portion of housing tube 700 may be configured to compress a first housing tube portion 720 of housing tube 700. In one or more embodiments, an application of a compressive force to an inner portion of housing tube 700 may be configured to gradually curve housing tube 700. Illustratively, a gradual curving of housing tube 700 may be configured to gradually curve optic fiber 750, e.g., from an optic fiber in a third curved position 1330 to an optic fiber in a fourth curved position 1340. For example, a line tangent to optic fiber distal end 751 may be parallel to a line tangent to housing tube proximal end 702, e.g., when optic fiber 750 comprises an optic fiber in a fourth curved position 1340.

In one or more embodiments, one or more properties of a steerable laser probe may be adjusted to attain one or more desired steerable laser probe features. For example, a stiffness of first housing tube portion 720 or a stiffness of second housing tube portion 730 may be adjusted to vary an amount of actuation of actuation lever 1220 configured to curve housing tube 700 to a particular curved position. Illustratively, a material comprising first housing tube portion 720 or a material comprising second housing tube portion 730 may be adjusted to vary an amount of actuation of actuation lever 1220 configured to curve housing tube 700 to a particular curved position.

In one or more embodiments, a number of apertures in housing tube 700 may be adjusted to vary an amount of actuation of actuation lever 1220 configured to curve housing tube 700 to a particular curved position. Illustratively, a location of one or more apertures in housing tube 700 may be adjusted to vary an amount of actuation of actuation lever 1220 configured to curve housing tube 700 to a particular curved position. In one or more embodiments, a geometry of one or more apertures in housing tube 700 may be adjusted to vary an amount of actuation of actuation lever 1220 configured to curve housing tube 700 to a particular curved position. Illustratively, a geometry of one or more apertures in housing tube 700 may be uniform, e.g., each aperture of the one or more apertures may have a same geometry. In one or more embodiments, a geometry of one or more apertures in housing tube 700 may be non-uniform, e.g., a first aperture in housing tube 700 may have a first geometry and a second aperture in housing tube 700 may have a second geometry.

Illustratively, a geometry or shape of actuation lever 1220 may be adjusted to vary an amount actuation of actuation lever 1220 configured to curve housing tube 700 to a particular curved position. In one or more embodiments, one or more locations within housing tube 700 wherein draw wire 1240 may be fixed to an inner portion of housing tube 700 may be adjusted to vary an amount of actuation of actuation lever 1220 configured to curve housing tube 700 to a particular curved position. Illustratively, a portion of draw wire 1240 may be fixed to an outer portion of housing tube 700. In one or more embodiments, a portion of draw wire 1240 may be looped around a portion of housing tube 700. Illustratively, a portion of housing tube 700 may comprise an access window, e.g., configured to allow access to an inner portion of housing tube 700. In one or more embodiments, a portion of housing tube 700 may comprise an access window, e.g., configured to allow access to a portion of optic fiber 750 or a portion of draw wire 1240. Illustratively, at least a portion of optic fiber 750 may be enclosed in an optic fiber sleeve configured to, e.g., protect optic fiber 750, vary a stiffness of optic fiber 750, vary an optical property of optic fiber 750, etc.

In one or more embodiments, a stiffness of first housing tube portion 720 or a stiffness of second housing tube portion 730 may be adjusted to vary a bend radius of housing tube 700. Illustratively, a stiffness of first housing tube portion 720 or a stiffness of second housing tube portion 730 may be adjusted to vary a radius of curvature of housing tube 700, e.g., when housing tube 700 is in a particular curved position. In one or more embodiments, a number of apertures in housing tube 700 may be adjusted to vary a bend radius of housing tube 700. Illustratively, a number of apertures in housing tube 700 may be adjusted to vary a radius of curvature of housing tube 700, e.g., when housing tube 700 is in a particular curved position. In one or more embodiments, a location or a geometry of one or more apertures in housing tube 700 may be adjusted to vary a bend radius of housing tube 700. Illustratively, a location or a geometry of one or more apertures in housing tube 700 may be adjusted to vary a radius of curvature of housing tube 700, e.g., when housing tube 700 is in a particular curved position.

Figure 14A:
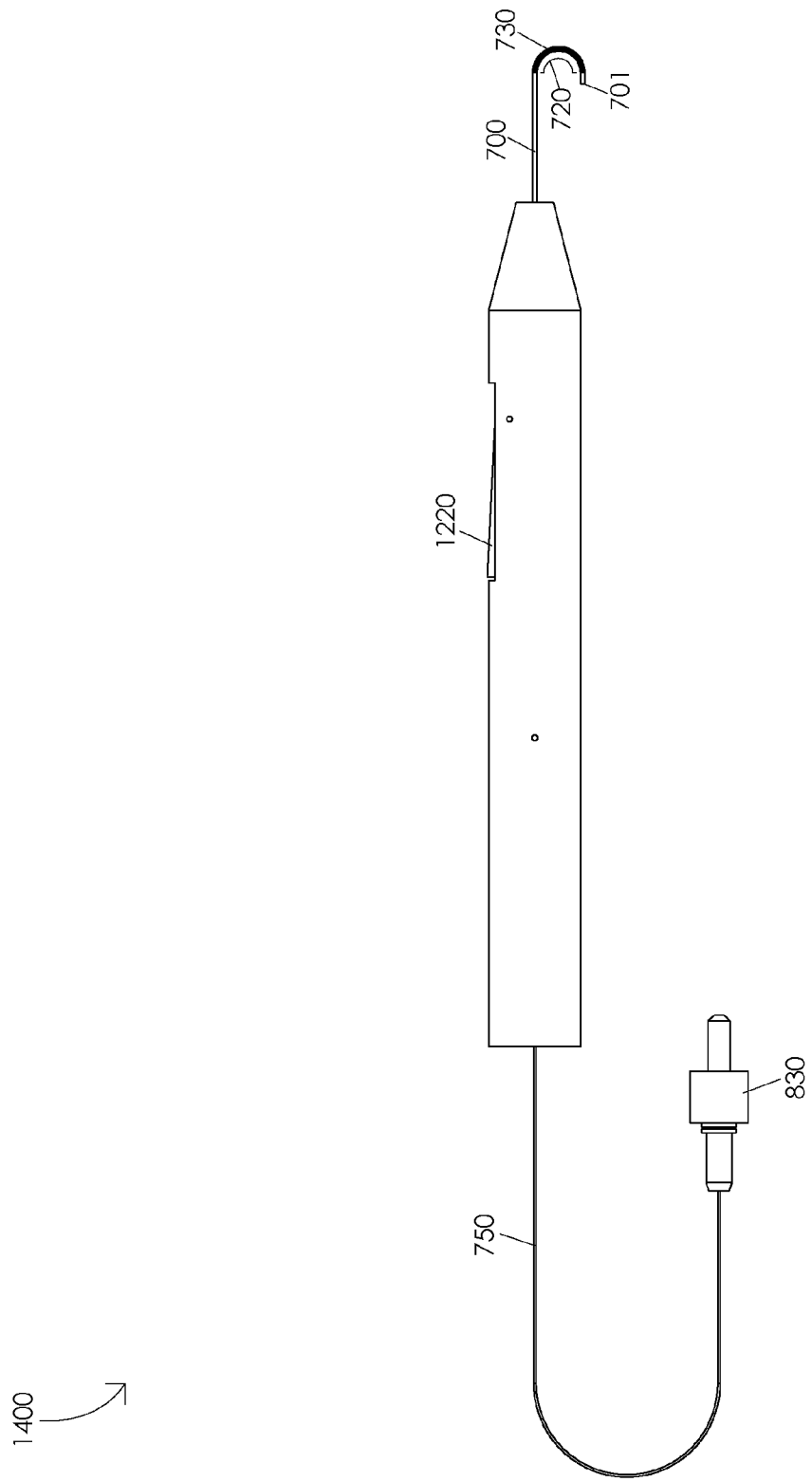
FIGS. 14A, 14B, 14C, 14D, and 14E illustrate a gradual straightening of an optic fiber.

FIGS. 14A, 14B, 14C, 14D, and 14E illustrate a gradual straightening of an optic fiber 750. FIG. 14A illustrates a fully curved optic fiber 1400. In one or more embodiments, optic fiber 750 may comprise a fully curved optic fiber 1400, e.g., when actuation lever proximal end 1222 is fully extended relative to handle base 1110. Illustratively, optic fiber 750 may comprise a fully curved optic fiber 1400, e.g., when first housing tube portion 720 is fully compressed. In one or more embodiments, a line tangent to optic fiber distal end 751 may be parallel to a line tangent to housing tube proximal end 702, e.g., when optic fiber 750 comprises a fully curved optic fiber 1400.

Figure 14B:
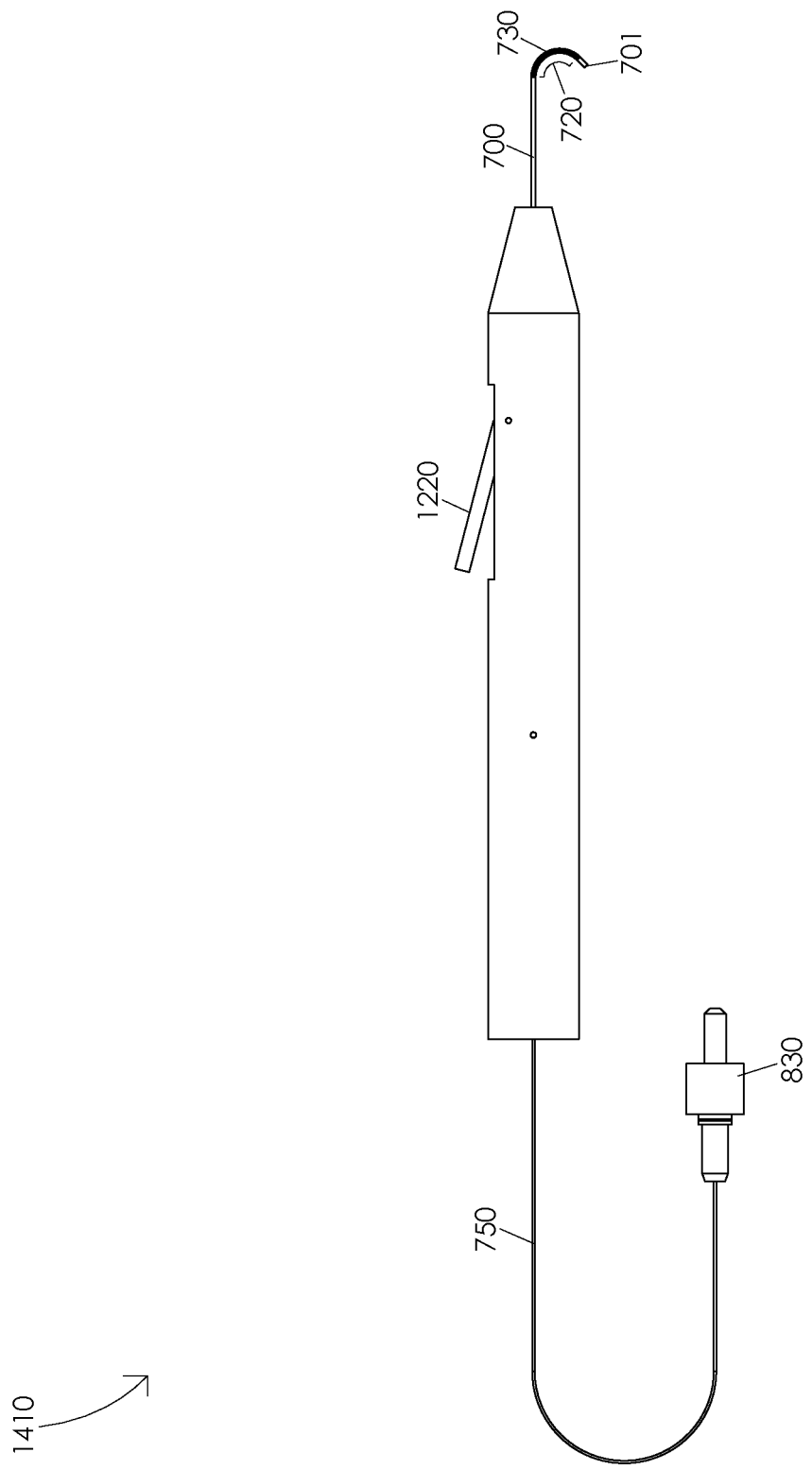

FIG. 14B illustrates an optic fiber in a first partially straightened position 1410. Illustratively, an actuation of actuation lever 1220, e.g., in a clockwise direction about pivot pin 1210, may be configured to gradually straighten optic fiber 750. For example, an actuation of actuation lever 1220, e.g., due to a reduction of a force applied to actuation lever 1220, may be configured to gradually straighten optic fiber 750. In one or more embodiments, a reduction of a force applied to actuation lever 1220 may be configured to gradually straighten optic fiber 750 from a fully curved optic fiber 1400 to an optic fiber in a first partially straightened position 1410. Illustratively, a reduction of a force applied to actuation lever 1220 may be configured to gradually extend draw wire 1240 relative to housing tube 700. In one or more embodiments, a gradual extension of draw wire 1240 relative to housing tube 700 may be configured to cause draw wire 1240 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750, e.g., from a fully curved optic fiber 1400 to an optic fiber in a first partially straightened position 1410. In one or more embodiments, a line tangent to optic fiber distal end 751 may intersect a line tangent to housing tube proximal end 702 at a first partially straightened angle, e.g., when optic fiber 750 comprises an optic fiber in a first partially straightened position 1410. Illustratively, the first partially straightened angle may comprise any angle less than 180 degrees. For example, the first partially straightened angle may comprise a 135 degree angle.

Figure 14C:
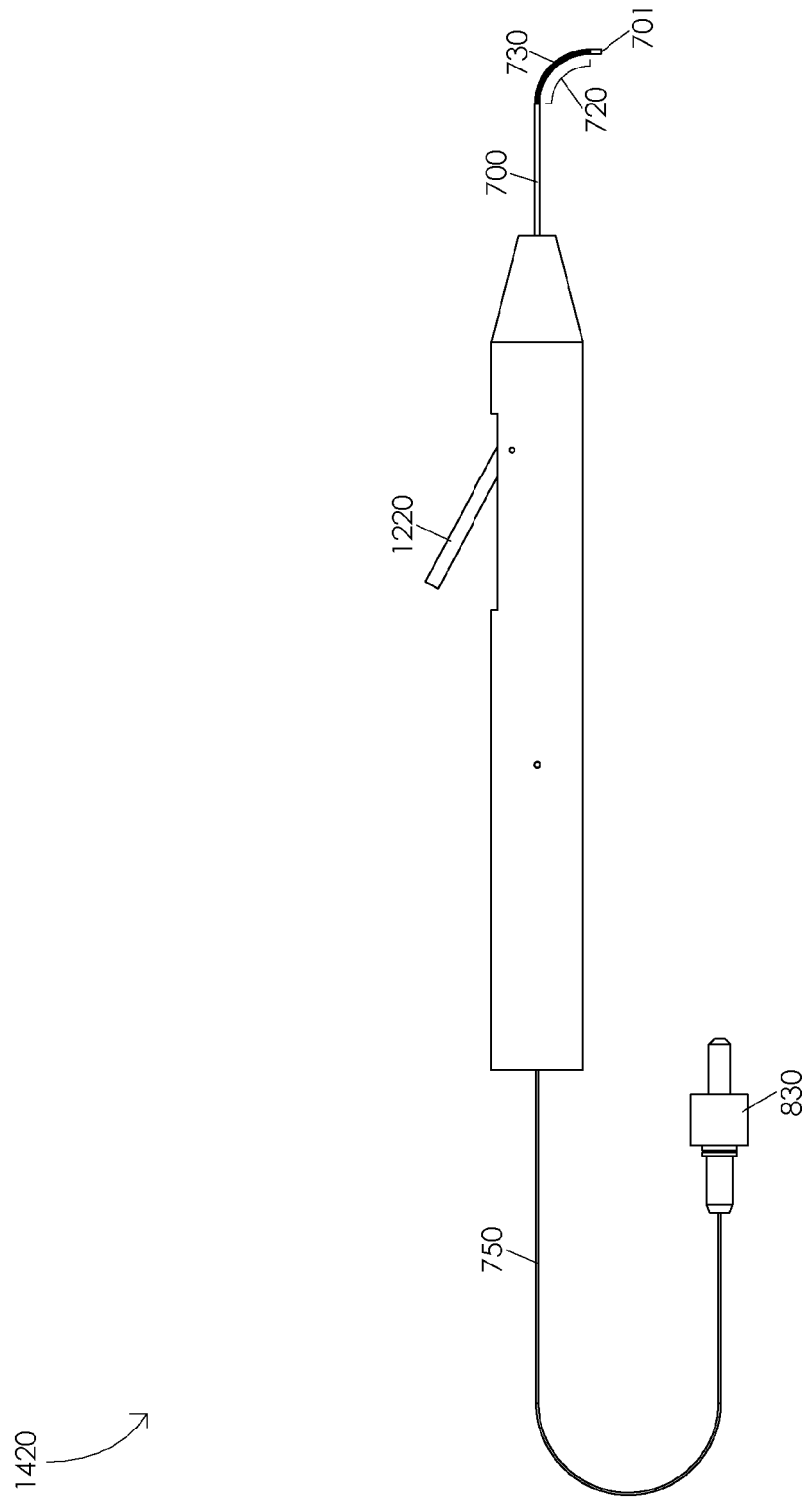

FIG. 14C illustrates an optic fiber in a second partially straightened position 1420. Illustratively, an actuation of actuation lever 1220, e.g., in a clockwise direction about pivot pin 1210, may be configured to gradually straighten optic fiber 750. For example, an actuation of actuation lever 1220, e.g., due to a reduction of a force applied to actuation lever 1220, may be configured to gradually straighten optic fiber 750. In one or more embodiments, a reduction of a force applied to actuation lever 1220 may be configured to gradually straighten optic fiber 750 from an optic fiber in a first partially straightened position 1410 to an optic fiber in a second partially straightened position 1420. Illustratively, a reduction of a force applied to actuation lever 1220 may be configured to gradually extend draw wire 1240 relative to housing tube 700. In one or more embodiments, a gradual extension of draw wire 1240 relative to housing tube 700 may be configured to cause draw wire 1240 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750, e.g., from an optic fiber in a first partially straightened position 1410 to an optic fiber in a second partially straightened position 1420. In one or more embodiments, a line tangent to optic fiber distal end 751 may intersect a line tangent to housing tube proximal end 702 at a second partially straightened angle, e.g., when optic fiber 750 comprises an optic fiber in a second partially straightened position 1420. Illustratively, the second partially straightened angle may comprise any angle less than the first partially straightened angle. For example, the second partially straightened angle may comprise a 90 degree angle.

Figure 14D:
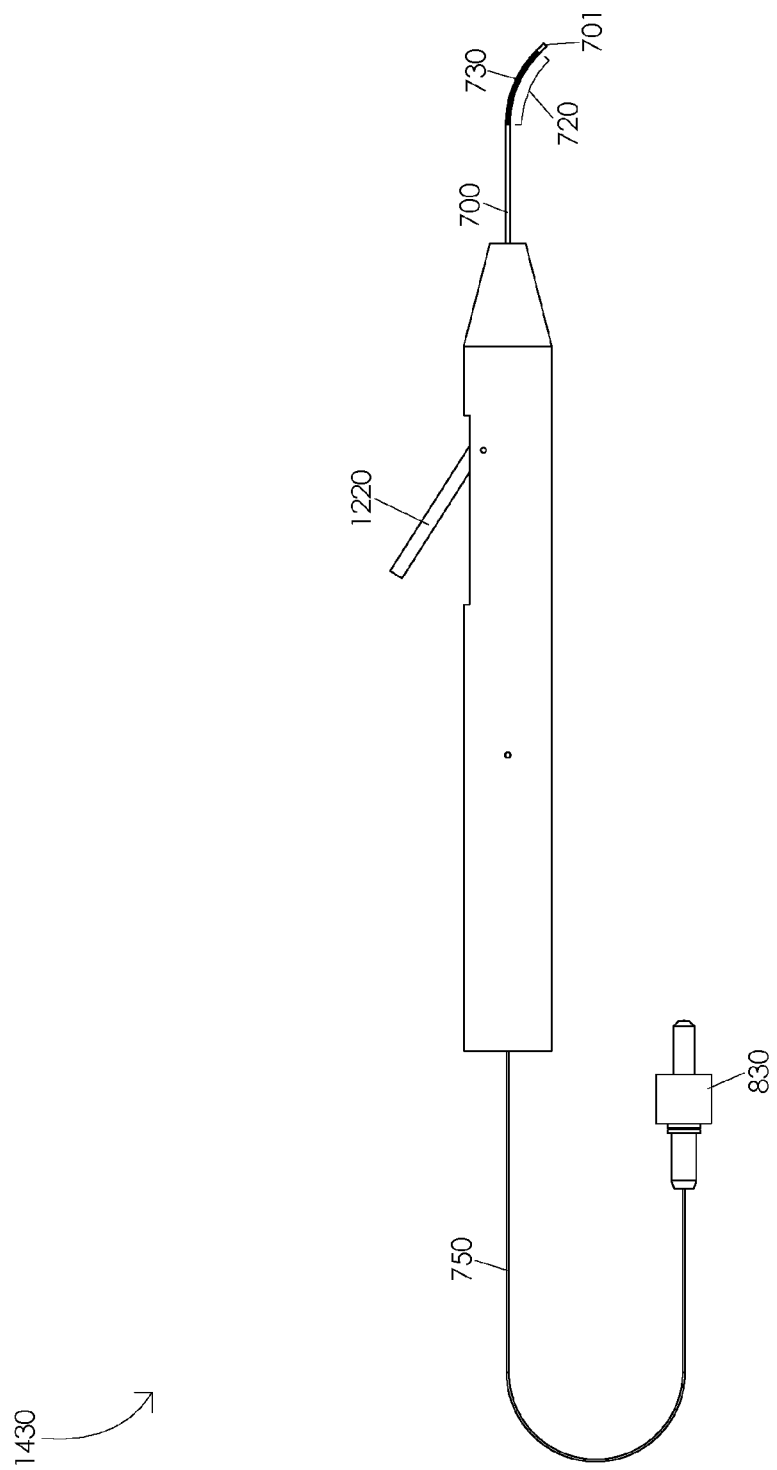

FIG. 14D illustrates an optic fiber in a third partially straightened position 1430. Illustratively, an actuation of actuation lever 1220, e.g., in a clockwise direction about pivot pin 1210, may be configured to gradually straighten optic fiber 750. For example, an actuation of actuation lever 1220, e.g., due to a reduction of a force applied to actuation lever 1220, may be configured to gradually straighten optic fiber 750. In one or more embodiments, a reduction of a force applied to actuation lever 1220 may be configured to gradually straighten optic fiber 750 from an optic fiber in a second partially straightened position 1420 to an optic fiber in a third partially straightened position 1430. Illustratively, a reduction of a force applied to actuation lever 1220 may be configured to gradually extend draw wire 1240 relative to housing tube 700. In one or more embodiments, a gradual extension of draw wire 1240 relative to housing tube 700 may be configured to cause draw wire 1240 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750, e.g., from an optic fiber in a second partially straightened position 1420 to an optic fiber in a third partially straightened position 1430. In one or more embodiments, a line tangent to optic fiber distal end 751 may intersect a line tangent to housing tube proximal end 702 at a third partially straightened angle, e.g., when optic fiber 750 comprises an optic fiber in a third partially straightened position 1430. Illustratively, the third partially straightened angle may comprise any angle less than the second partially straightened angle. For example, the third partially straightened angle may comprise a 45 degree angle.

Figure 14E:
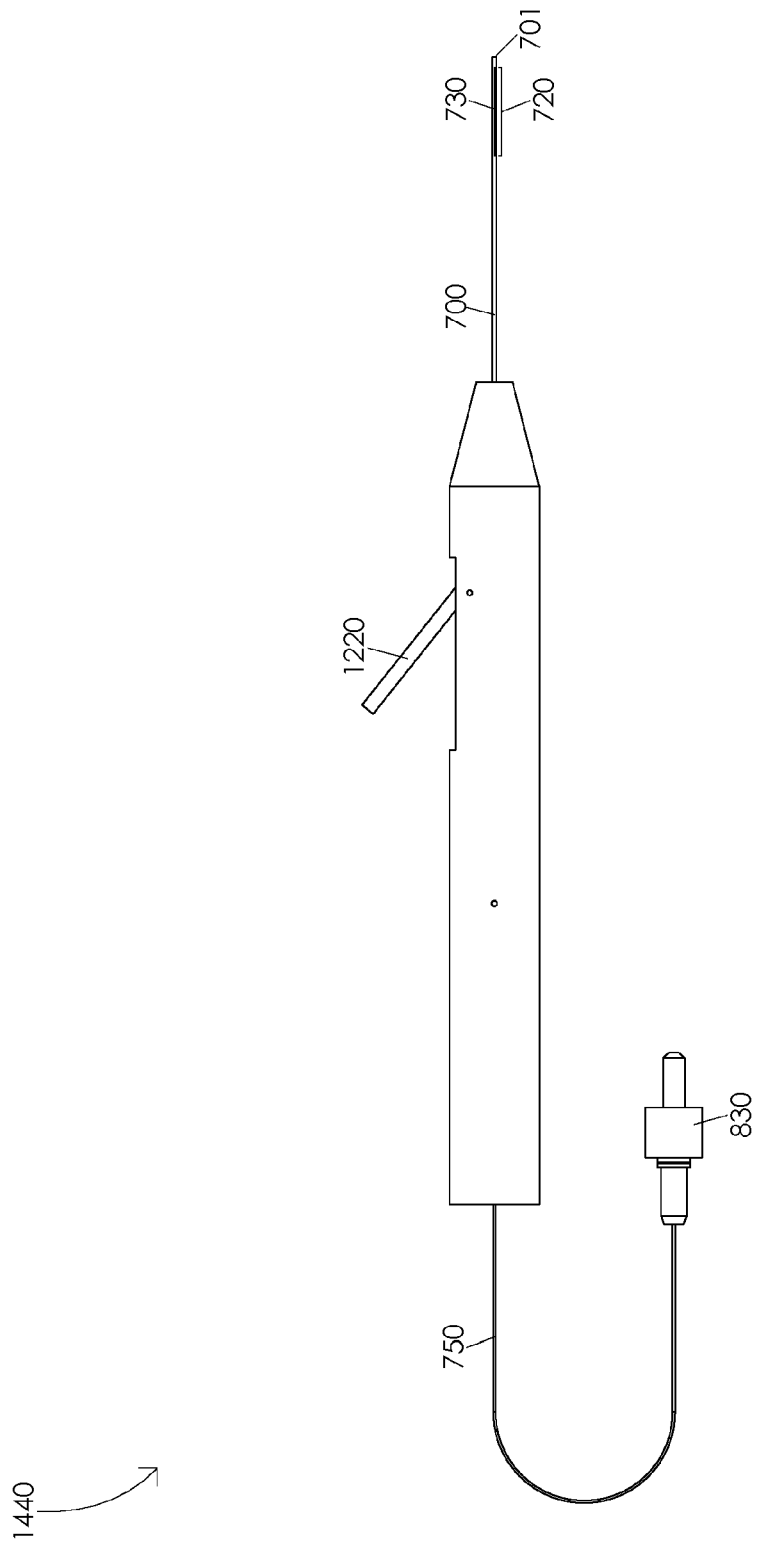

FIG. 14E illustrates an optic fiber in a fully straightened position 1440. Illustratively, an actuation of actuation lever 1220, e.g., in a clockwise direction about pivot pin 1210, may be configured to gradually straighten optic fiber 750.

For example, an actuation of actuation lever 1220, e.g., due to a reduction of a force applied to actuation lever 1220, may be configured to gradually straighten optic fiber 750. In one or more embodiments, a reduction of a force applied to actuation lever 1220 may be configured to gradually straighten optic fiber 750 from an optic fiber in a third partially straightened position 1430 to an optic fiber in a fully straightened position 1440. Illustratively, a reduction of a force applied to actuation lever 1220 may be configured to gradually extend draw wire 1240 relative to housing tube 700. In one or more embodiments, a gradual extension of draw wire 1240 relative to housing tube 700 may be configured to cause draw wire 1240 to reduce a compressive force applied to an inner portion of housing tube 700. Illustratively, a reduction of a compressive force applied to an inner portion of housing tube 700 may be configured to decompress a first housing tube portion 720 of housing tube 700. In one or more embodiments, a reduction of a compressive force applied to an inner portion of housing tube 700 may be configured to gradually straighten housing tube 700. Illustratively, a gradual straightening of housing tube 700 may be configured to gradually straighten optic fiber 750, e.g., from an optic fiber in a third partially straightened position 1430 to an optic fiber in a fully straightened position 1440. In one or more embodiments, a line tangent to optic fiber distal end 751 may be parallel to a line tangent to housing tube proximal end 702, e.g., when optic fiber 750 comprises an optic fiber in a fully straightened position 1440.

Illustratively, a surgeon may aim optic fiber distal end 751 at any of a plurality of targets within an eye, e.g., to perform a photocoagulation procedure. In one or more embodiments, a surgeon may aim optic fiber distal end 751 at any target within a particular transverse plane of the inner eye by, e.g., rotating handle 1100 to orient housing tube 700 in an orientation configured to cause a curvature of housing tube 700 within the particular transverse plane of the inner eye and varying an amount of actuation of actuation lever 1220. Illustratively, a surgeon may aim optic fiber distal end 751 at any target within a particular sagittal plane of the inner eye by, e.g., rotating handle 1100 to orient housing tube 700 in an orientation configured to cause a curvature of housing tube 700 within the particular sagittal plane of the inner eye and varying an amount of actuation of actuation lever 1220. In one or more embodiments, a surgeon may aim optic fiber distal end 751 at any target within a particular frontal plane of the inner eye by, e.g., varying an amount of actuation of actuation lever 1220 to orient a line tangent to optic fiber distal end 751 wherein the line tangent to optic fiber distal end 751 is within the particular frontal plane of the inner eye and rotating handle 1100. Illustratively, a surgeon may aim optic fiber distal end 751 at any target located outside of the particular transverse plane, the particular sagittal plane, and the particular frontal plane of the inner eye, e.g., by varying a rotational orientation of handle 1100 and varying an amount of actuation of actuation lever 1220. In one or more embodiments, a surgeon may aim optic fiber distal end 751 at any target of a plurality of targets within an eye, e.g., without increasing a length of a portion of a steerable laser probe within the eye. Illustratively, a surgeon may aim optic fiber distal end 751 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:
1. A laser probe comprising:
a handle having a handle distal end and a handle proximal end;
an actuation channel of the handle;
an optic fiber guide of the handle;
an actuation lever having an actuation lever distal end and an actuation lever proximal end wherein the actuation lever proximal end is disposed in the actuation channel and wherein the actuation lever distal end extends out from the actuation channel;
a pivot pin guide of the actuation lever;
a wire proximal loop housing of the actuation lever;
a pivot pin housing of the handle;
a pivot pin, the pivot pin disposed in the pivot pin housing and the pivot pin guide;
a single housing tube having a housing tube distal end and a housing tube proximal end, the housing tube fixed to a portion of the handle;
a wire having a wire distal end and a wire proximal end, the wire disposed in the housing tube wherein the wire distal end is adjacent to the housing tube distal end and wherein a portion of the wire is fixed to the housing tube;
a wire proximal loop of the wire, the wire proximal loop disposed in the wire proximal loop housing wherein the wire proximal loop is disposed around a portion of the actuation lever and wherein the wire proximal loop is fixed in the wire proximal loop housing; and
an optic fiber having an optic fiber distal end and an optic fiber proximal end, the optic fiber disposed in an inner bore of the handle, the optic fiber guide, the actuation channel, and the housing tube wherein the optic fiber distal end is adjacent to the housing tube distal end and wherein a portion of the optic fiber is fixed to an inner portion of the housing tube and wherein actuating the actuation lever distal end away from the handle proximal end is configured to rotate the actuation lever about the pivot pin in a first direction and retract the cable relative to the housing tube and curve the housing tube and the optic fiber.

2. The laser probe of claim 1 further comprising: a first housing tube portion of the housing tube having a first stiffness; and
a second housing tube portion of the housing tube having a second stiffness wherein the second stiffness is greater than the first stiffness.

3. The laser probe of claim 2 further comprising: a plurality of apertures of the first housing tube portion.

4. The laser probe of claim 3 wherein at least one aperture of the plurality of apertures is a slit.

5. The laser probe of claim 3 wherein at least two apertures of the plurality of apertures are configured to separate at least one solid portion of the housing tube.

6. The laser probe of claim 3 wherein at least one aperture of the plurality of apertures is laser cut into the first housing tube portion.

7. The laser probe of claim 3 further comprising:
an arch of at least one aperture of the plurality of apertures.

8. The laser probe of claim 1 wherein the housing tube is manufactured from a polymer.

9. The laser probe of claim 1 wherein the housing tube is manufactured from a metal.

10. The laser probe of claim 1 wherein the housing tube is manufactured from a metal alloy.

11. The laser probe of claim 1 further comprising:
a first housing tube portion of the housing tube manufactured from a first material; and
a second housing tube portion of the housing tube manufactured from a second material.

12. The laser probe of claim 11 wherein the first housing tube portion has a first stiffness and the second housing tube portion has a second stiffness and wherein the second stiffness is greater than the first stiffness.

13. The laser probe of claim 1 further comprising: a light source interface.

14. The laser probe of claim 13 wherein the light source interface is a standard light source connector.

15. The laser probe of claim 14 wherein the light source interface is an SMA connector.

16. The laser probe of claim 1 wherein the handle is manufactured from a metal.

17. The laser probe of claim 1 wherein a rotation of the actuation lever about the pivot pin in the first direction is configured to curve the housing tube and the optic fiber at least 45 degrees relative to the housing tube proximal end.

18. The laser probe of claim 1 wherein a rotation of the actuation lever about the pivot pin in the first direction is configured to curve the housing tube and the optic fiber at least 90 degrees relative to the housing tube proximal end.

19. The laser probe of claim 1 wherein a rotation of the actuation lever about the pivot pin in a second direction is configured to straighten the optic fiber.

20. The laser probe of claim 1 wherein a rotation of the actuation lever about the pivot pin in a second direction is configured to straighten the housing tube.

* * * * *